(12) United States Patent
Fox et al.

(10) Patent No.: US 12,318,484 B2
(45) Date of Patent: *Jun. 3, 2025

(54) PEGYLATED LIPOSOMES AND METHODS OF USE

(71) Applicants: ACCESS TO ADVANCED HEALTH INSTITUTE, Seattle, WA (US); University of Virginia Patent Foundation, Charlottesville, VA (US)

(72) Inventors: Christopher B. Fox, Sumner, WA (US); Susan S. Lin, Kirkland, WA (US); Darrick Carter, Seattle, WA (US); Neal Van Hoeven, Seattle, WA (US); Mayuresh M. Abhyankar, Charlottesville, VA (US); William A. Petri, Charlottesville, VA (US)

(73) Assignees: Access to Advanced Health Institute, Seattle, WA (US); University of Virginia Patent Foundation, Charlottesville, VA (US)

( * ) Notice: Subject to any disclaimer, the term of this patent is extended or adjusted under 35 U.S.C. 154(b) by 529 days.

This patent is subject to a terminal disclaimer.

(21) Appl. No.: 17/560,594

(22) Filed: Dec. 23, 2021

(65) Prior Publication Data

US 2022/0160632 A1     May 26, 2022

Related U.S. Application Data

(63) Continuation of application No. 16/098,619, filed as application No. PCT/US2017/032756 on May 15, 2017, now Pat. No. 11,266,602.

(Continued)

(51) Int. Cl.
*A61K 9/1271*     (2025.01)
*A61K 31/739*     (2006.01)
(Continued)

(52) U.S. Cl.
CPC .......... *A61K 9/1271* (2013.01); *A61K 31/739* (2013.01); *A61K 39/39* (2013.01);
(Continued)

(58) Field of Classification Search
CPC .... A61K 9/1271; A61K 31/739; A61K 39/39; A61K 2039/55555; A61K 2039/6087;
(Continued)

(56) References Cited

U.S. PATENT DOCUMENTS 8,609,114 B2    12/2013   Reed et al.
2012/0014866 A1    1/2012   Bull et al.
(Continued)

FOREIGN PATENT DOCUMENTS

JP      2015512950 A     4/2015
JP      2018-559785 A     7/2019
(Continued)

OTHER PUBLICATIONS

Office Action from related Canadian Patent Application No. 3,023,672, mailed Mar. 22, 2023, 5 pages.
(Continued)

*Primary Examiner* — Benjamin J Packard
*Assistant Examiner* — Lucy M Tien
(74) *Attorney, Agent, or Firm* — Benjamin Keim; Newport IP, LLC

(57) ABSTRACT

Provided herein are PEGylated liposomes, and methods of making and using thereof. The PEGylated liposomes comprise at least a cholesterol, a non-PEGylated neutral lipid, and a PEGylated lipid, wherein the average molecular weight of the PEG component in the PEGylated lipid is about 5000 Daltons or less. The PEGylated liposomes are stable and capable of delivery of an agent for the generation of an immune response, for example an agent for vaccine, therapeutic, or diagnostic uses. Compositions and methods (Continued)

related to making the PEGylated liposomes and using the PEGylated liposomes for stimulating an immune response are also provided.

18 Claims, 24 Drawing Sheets

Related U.S. Application Data

(60) Provisional application No. 62/337,328, filed on May 16, 2016.

(51) Int. Cl.
*A61K 39/00* (2006.01)
*A61K 39/39* (2006.01)

(52) U.S. Cl.
CPC .............. *A61K 2039/55555* (2013.01); *A61K 2039/6087* (2013.01)

(58) Field of Classification Search
CPC .... A61K 2039/543; A61K 2039/55511; A61K 2039/55566; A61K 2039/6018; A61K 39/002; A61K 9/0019; A61K 9/0043; A61K 39/12; A61K 47/02; A61K 9/107; A61K 31/7024; A61K 39/145; A61K 47/10; A61K 47/12; A61K 47/14; A61K 47/24; A61K 47/28; A61K 2039/57; A61P 31/16; A61P 33/04; C12N 2760/16134; C12N 2760/16171; Y02A 50/30
See application file for complete search history.

(56) References Cited

U.S. PATENT DOCUMENTS

| | | |
|---|---|---|
| 2012/0148663 A1 | 6/2012 | Nilssen et al. |
| 2014/0027182 A1 | 1/2014 | Wilson |
| 2014/0030212 A1 | 1/2014 | Vasconcellos et al. |
| 2014/0035641 A1 | 2/2014 | Pasquale et al. |
| 2014/0271821 A1 | 9/2014 | McGhee |
| 2014/0302120 A1 | 10/2014 | Carson et al. |
| 2014/0356416 A1 | 12/2014 | Kesari et al. |
| 2015/0064265 A1 | 3/2015 | Fahmy et al. |

FOREIGN PATENT DOCUMENTS

| | | | |
|---|---|---|---|
| WO | 2012031043 A1 | 3/2012 | |
| WO | 2015123496 A1 | 8/2015 | |
| WO | 2015136479 A1 | 9/2015 | |
| WO | 2017-200957 A1 | 11/2017 | |

OTHER PUBLICATIONS

Khantasup, et al., Target Small Interfering RNA-Immunoliposomes as a Promising Therapeutic Agent against Highly Pathogenic Avian Influenza A (H5N1) Virus Infection, Antimicrobial Agents and Chemotherapy, p. 2816-2824, May 2014, vol. 58, No. 5.

Office Action from related Chinese Patent Application No. 2017800302944 mailed Aug. 31, 2023, 16 pages (translation attached).
Office Action from related Japanese Patent Application No. 2022-143788, mailed Aug. 31, 2023, 9 pages (translation attached).
AU 2017268175—Examination Report, mailed Apr. 1, 2022, 5 pages.
KR 10-2018-7034749—Office Action, mailed Jan. 3, 2022, 24 pages. (with English translation).
Office action for related patent application in Canada CIPO, application No. 3,023,672, mailed Nov. 27, 2023, 3 pages.
Office action for related patent application in Israel PTO, application No. 263030, mailed Oct. 26, 2023, 4 pages.
Indian Application No. 202118057586—Exam Report, mailed Apr. 28, 2022, 7 pages. (with English translation).
CN 201780030294.4—Second Office Action, mailed Apr. 24, 2022, 13 pages, with English translation.
JP 2018-559785—Decision of Refusal, mailed May 9, 2022, 8 pages, with English translation.
KR 10-2018-7034749—Notice of Decision for Rejection, mailed Jul. 7, 2022, with English translation.
Dmitri Smirnov, et al., "Vaccine Adjuvant Activity of 3M-052: An Imidazoquinoline Designed for Local Activity without Systemic Cytokine Induction", May 2011, 10 pages.
AU 2017268175—Second Examination Report, mailed Aug. 24, 2022, 3 pages.
Application No. 10-2018-7034749—Notice of Allowance, mailed Oct. 14, 2022, 4 pages. (with English translation).
Application No. MX/a/2018/013640—First Office Action, mailed Oct. 19, 2022, 12 pages. (with English translation).
Application No. IL 263030—Second Office Action, mailed Oct. 20, 2022, 9 pages. (with English translation).
Application No. JP 2018-559785—Decision to Grant, mailed Nov. 17, 2022, 7 pages. (with English translation).
Application No. AU 2017268175—Notice of Acceptance, mailed Feb. 8, 2023, 3 pages. (with English translation).
Application No. CN 2017800302944—Third Office Action, mailed Feb. 11, 2023, 17 pages. (with English translation).
Application No. MX/a/2018/013640—Second Office Action, mailed Feb. 23, 2023, 8 pages. (with English translation).
Notice of Acceptance for Patent Application for related patent Australian Patent Application No. 2023200515 mailed Apr. 9, 2024, 3 pages.
Office Action from related patent Japan Patent Application No. 2022-143788 dated Jun. 18, 2024, 9 pages, translation attached.
Khantasup, K., et al., "Targeted small interfering RNA-immunoliposomes as a promising therapeutic agent against highly pathogenic Avian Influenza A (H5N1) virus infection.",Antimicrobial Agents and Chemotherapy, v 58, n 5, 2014, p. 2816-2824.
Smirnov, et al., "Vaccine adjuvant activity of 3M-052: An imidazoquinoline designed for local activity without systemic cytokine induction," Vaccine vol. 29, 2011m pp. 5434 to 5442.
Fox, et al., "A nanoliposome delivery system to synergistically trigger TLR4 and TLR7," Journal of Nanobiologytechnology, 2014, vol. 12:17, pp. 1-9.
Goff, et al., "Synthetic Toll-Like Receptor 4 (TLR4) and TLR7 Ligands as Influenza Virus Vaccing Adjuvants Induce Rapid, Sustained, and Broadly Protective Responses," 15 pages.
Related matter Japanese patent application No. 2022-143788, Decision of Refusal mailed Feb. 25, 2025, 8 pages (translation included.

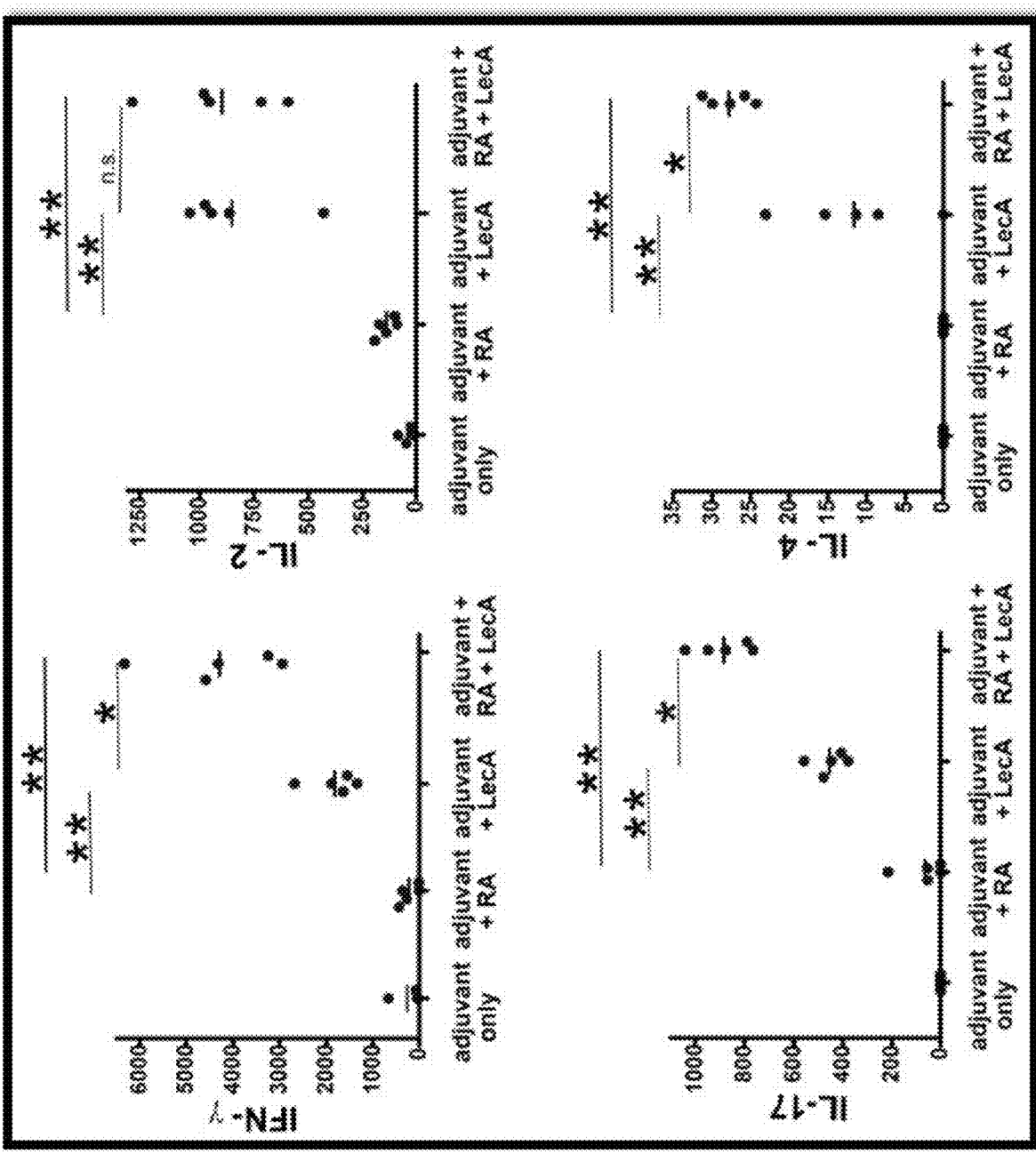

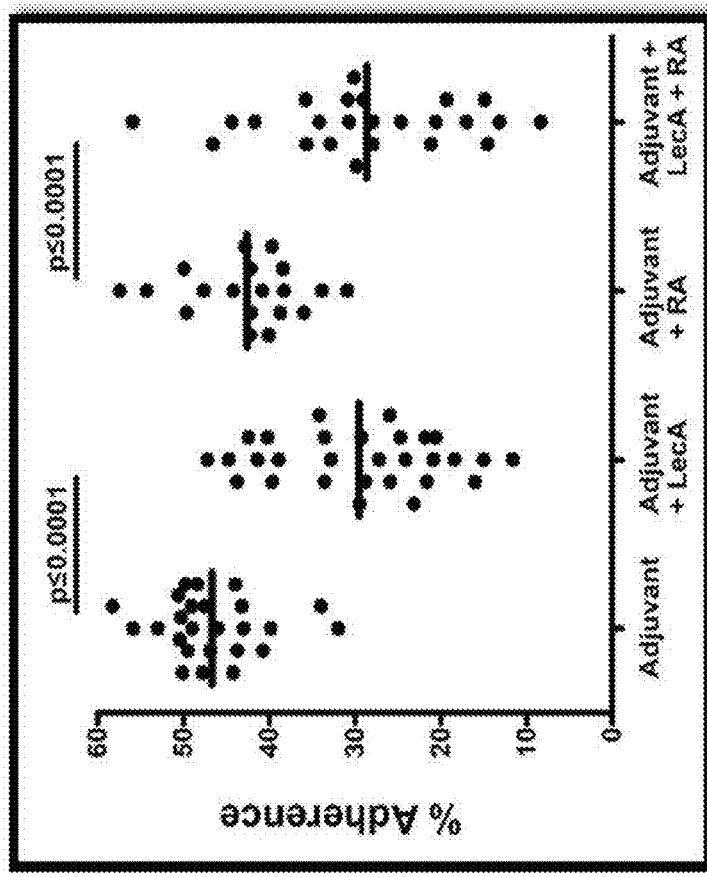
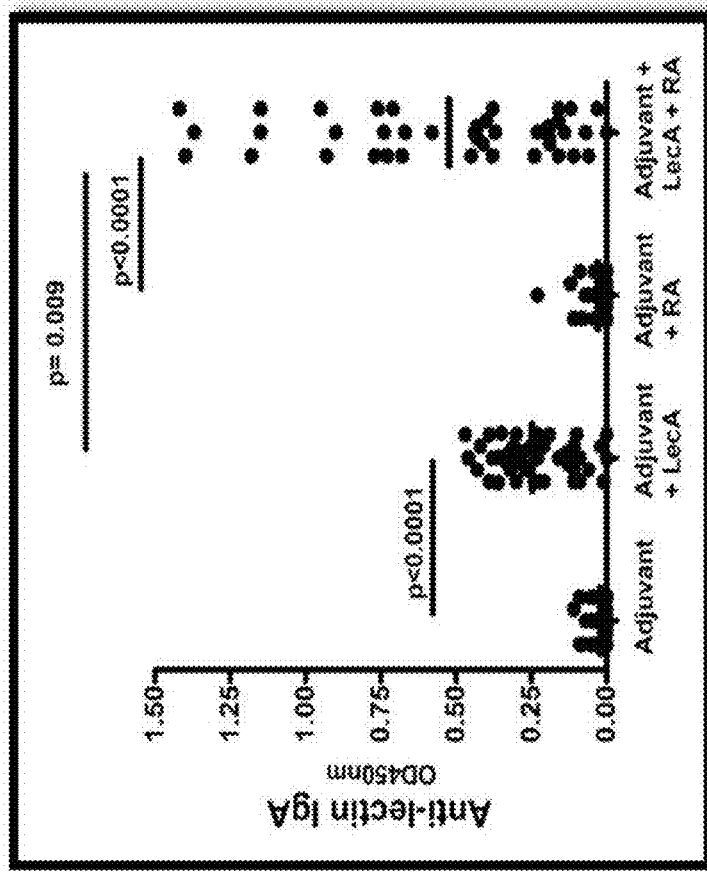
FIG. 4A
Fig. 4B

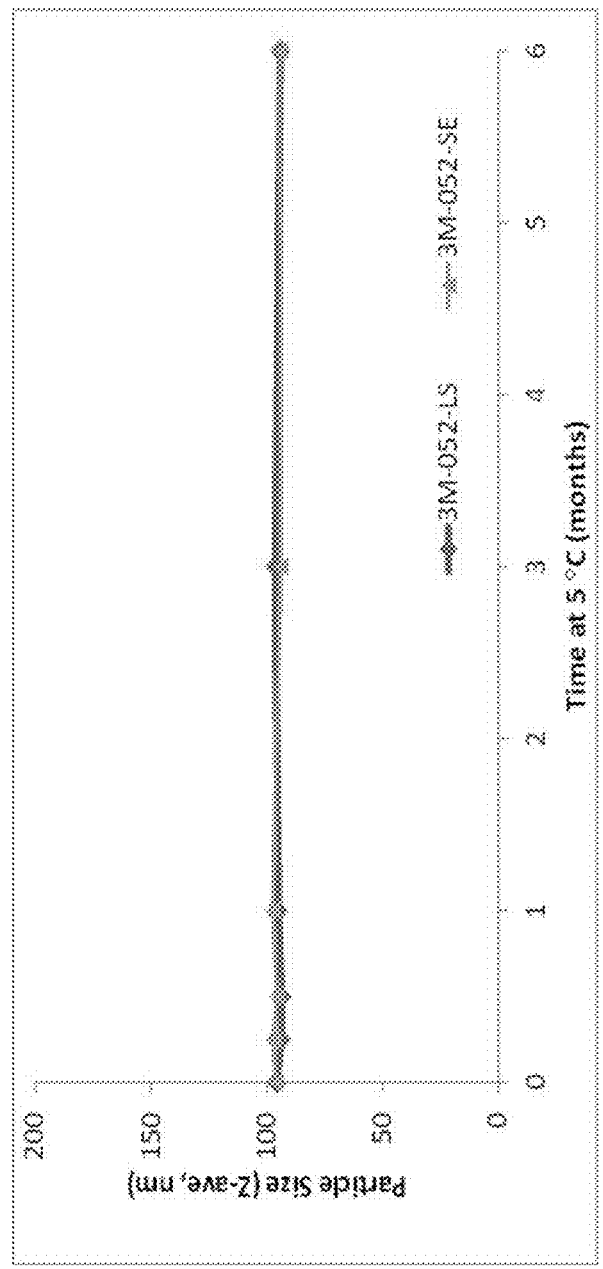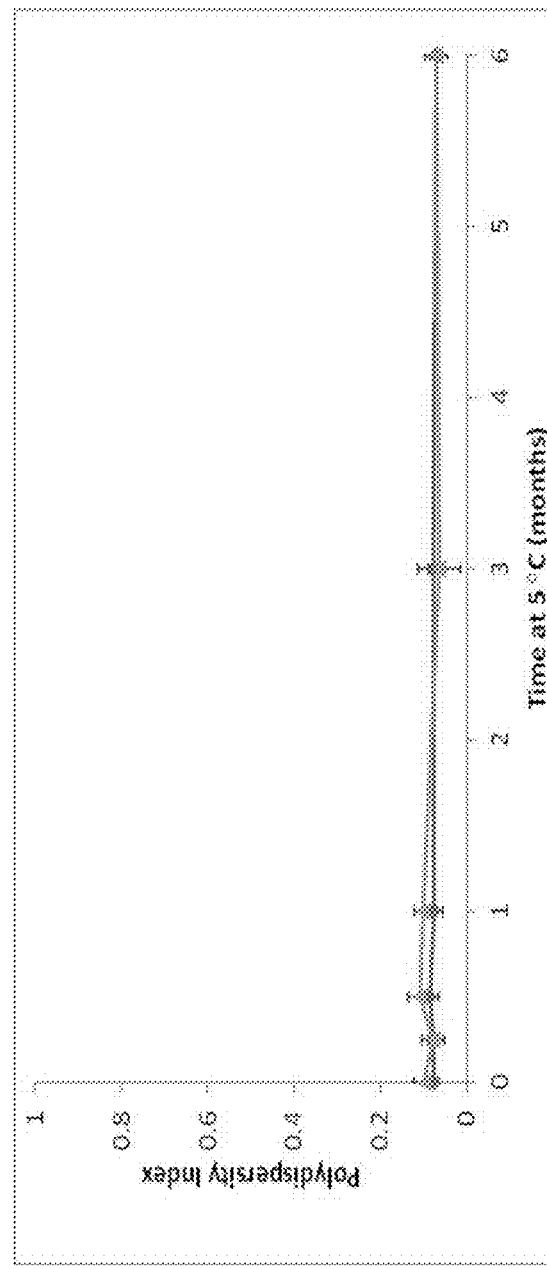

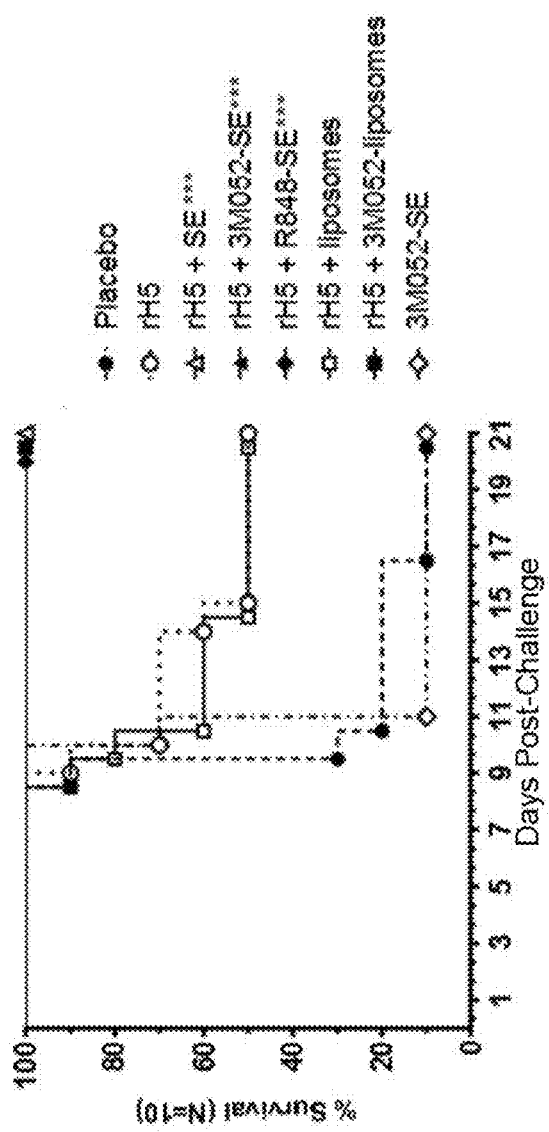
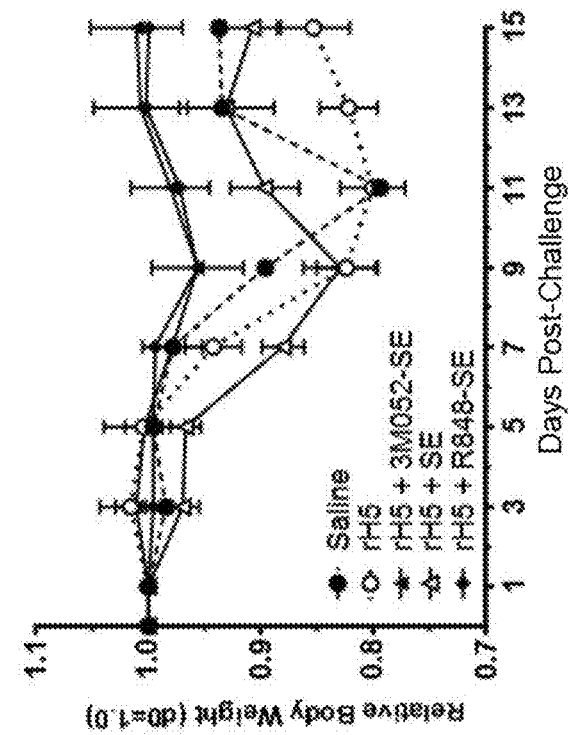
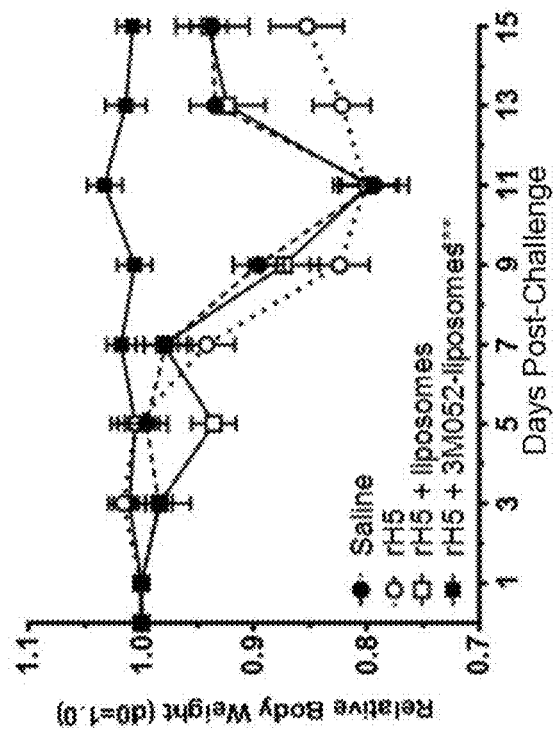
Fig. 11A
Fig. 11B
Fig. 11C

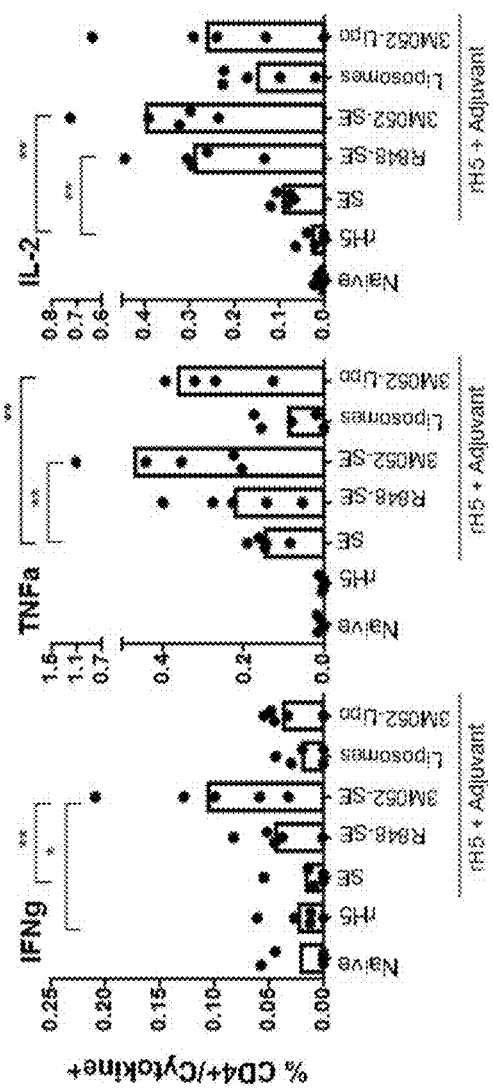
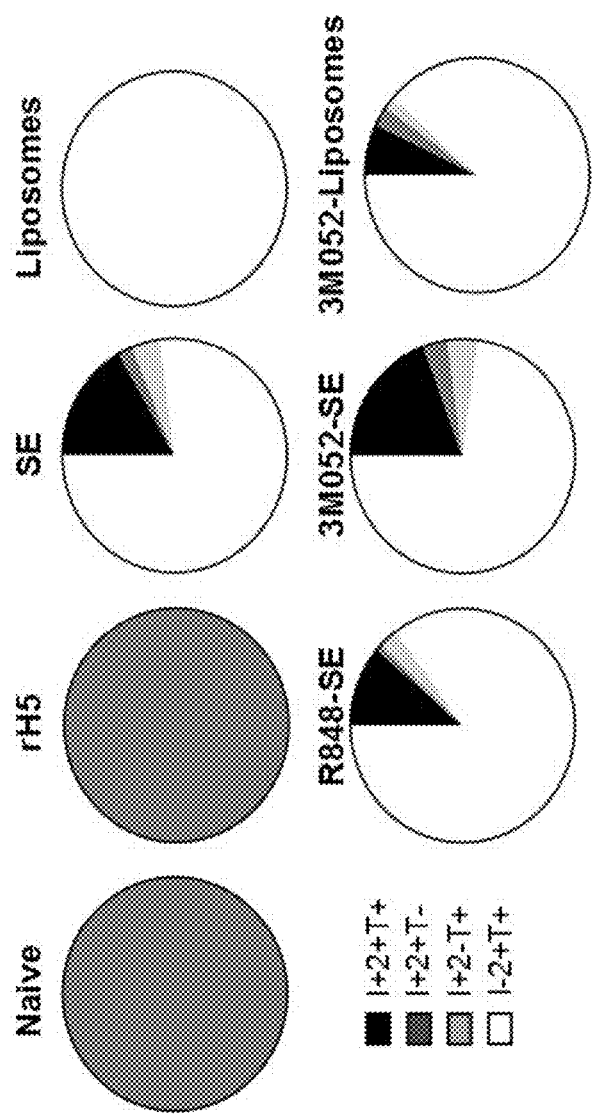
Fig. 12A, Fig. 12B, Fig. 12C, Fig. 12D

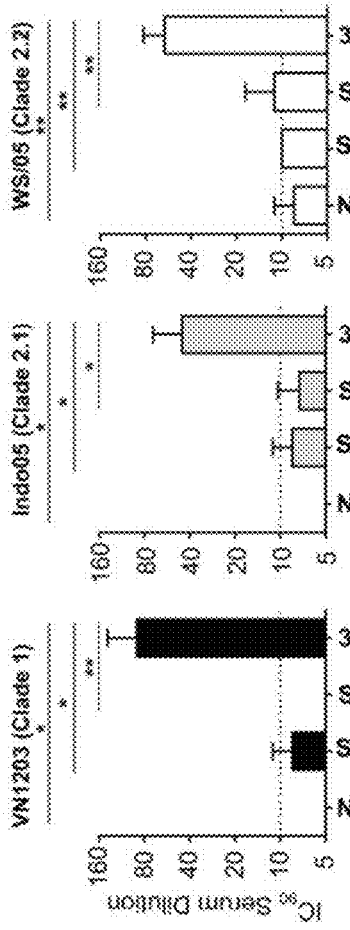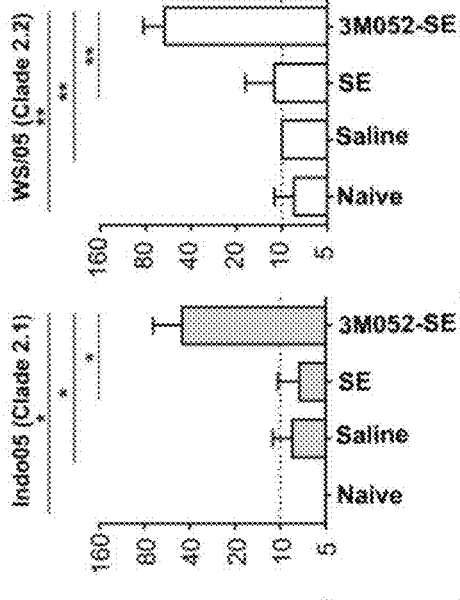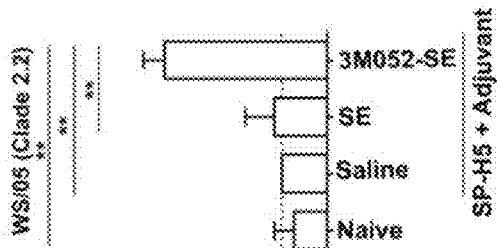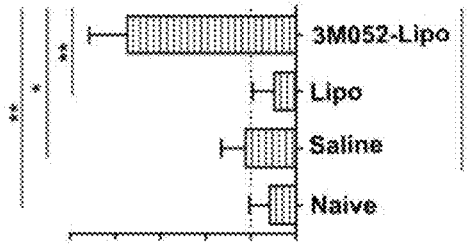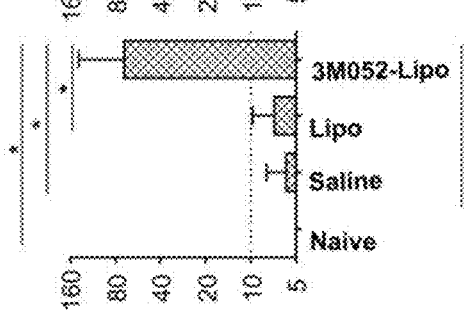

PEGYLATED LIPOSOMES AND METHODS OF USE

CROSS-REFERENCE TO RELATED APPLICATIONS

This non-provisional application is a continuation of U.S. application Ser. No. 16/098,619, filed on Nov. 2, 2018, which is a 371 of International Application No. PCT/US2017/032756 filed May 15, 2017, which claims the benefit of U.S. Provisional Application No. 62/337,328, filed May 16, 2016, each of which is hereby incorporated by reference in its entirety for any purpose.

STATEMENT REGARDING FEDERALLY SPONSORED RESEARCH OR DEVELOPMENT

This invention was made with government support under Contract No. HHSO100201000039C awarded by the Biomedical Advanced Research and Development Authority (BARDA) within the Office of the Assistant Secretary for Preparedness and Response (ASPR) in the U.S. Department of Health and Human Services and under Grant No. 5R21AI109118 and Contract No. HHSN272200800045C awarded by the National Institute of Allergy and Infectious Diseases, within the National Institutes of Health in the Department of Human and Health Services. The government has certain rights in the invention.

BACKGROUND OF THE INVENTION

Liposome-based delivery systems have been developed for biomolecules such as drugs and imaging agents. Such liposomes offer advantages such as a prolonged circulatory persistence leading to an improved presentation to the immune system, controlled release of the biomolecule, and the versatility to allow formulation of both hydrophobic and hydrophilic biomolecules. To prolong the circulatory half life of the liposomes requires that they be shielded from normal clearance mechanisms including interactions with serum proteins and phagocytes. Numerous approaches to improve the shielding of liposomes from the immune system have been developed including PEGylation of liposomes (liposomes containing a polyethylene glycol (PEG)). Liposomes containing PEG and other copolymers designed to shield the liposome from macrophages have been termed in the art as "stealth liposomes" In addition to shielding properties, PEGylation can impact the stability of the liposome preparation by restraining, however not excluding, the fusion of liposomes upon prolonged storage. To evade such fusions, the PEG corona should provide a sufficiently thick layer to sterically shield the liposomal surface.

PEG molecular weight has traditionally been considered to be an important determinant of effective surface shielding. PEGylated liposomes coated with lower molecular weight PEGs were ineffective at shielding. For example, when PEGylated liposomes with 750 Daltons PEG were compared to non-PEGylated liposomes, there was no difference (Mori et al., FEBS Lett, 1991). Prolonged blood circulation and reduced phagocytic uptake was only observed only when the PEG molecular weight was increased to greater than 5000 Daltons.

Liposomes have also been evaluated for delivery of subunit protein vaccines and adjuvants. Liposomes are attractive vaccine delivery vehicles due to the ability to tailor the liposome composition to achieve desired lipid concentration, charge, size, and distribution or targeting of antigen and adjuvant. Numerous liposome-based systems have been evaluated including anionic, cationic, and neutral liposomes, yet not all liposomes are created equal. Many cationic lipid liposome formulations are toxic. Many neutral liposomes are unstable ex vivo and either grow in size over time or fall apart immediately after manufacture. Anionic liposomes have charge limitations that affect their ability to deliver various antigens and fuse with cellular membranes. Other liposomes contain synthetic lipids or block copolymers which may exert effects on the immune system itself. Cholesterol-based liposome formulations are ideal in that cholesterol is a natural component of human cell membranes, and when combined with other co-lipids, such as DOTAP and DOPC, forms stable cationic nanoparticles of approximately 100-200 nm with desirable polydispersity indexes of around 0.3. Various strategies have been employed to improve liposomal formulations for use as vaccine formulations including PEGylation strategies. To date, no clear formulation has been developed that both overcomes the problems associated with the stability and toxicities of known liposomes, and can effectively improve the quality of immune response (reviewed in Carstens et al. Vaccine 29, 2011; Kaur et al. Journal of Controlled Release, 2012; Schwendener, Ther Adv Vaccines, 2014; Nag and Awasthi, Pharmaceutics, 2013; Vartak and Sucheck, Vaccines, 2016; Fan et al., Journal of Controlled Release, 2015; Schmidt et al., Pharmaceutics, 2016).

Thus, there is a need to develop PEGylated liposomes that are stable, manufacturable, compatible with lipid-based antigens and adjuvants, and small in size, for vaccines, therapeutics, and diagnostics. In the realm of vaccines, there is especially a need to provide such liposomes in conjunction with adjuvants that can enhance an immune response and vaccinations for influenza, enteric diseases (such as amebiasis), tuberculosis, HIV, cancer, and hepatitis, for example, could benefit from the development of such liposomes. Provided herein are compositions and methods related to the same.

All references cited herein, including patent applications and patent publications are herein incorporated by reference in their entirety, as if each individual reference is specifically and individually indicated to be incorporated by reference.

BRIEF SUMMARY OF THE INVENTION

The present invention provides PEGylated liposomes, formulations and compositions comprising the PEGylated liposomes, and methods of making and using the PEGylated liposomes. The PEGylated liposomes are useful for vaccines, therapeutics, and diagnostics.

The PEGylated liposomes comprise at least a cholesterol, a non-PEGylated neutral lipid, and a PEGylated lipid, wherein the average molecular weight of the PEG component in the PEGylated lipid is about 5000 Daltons or less. The PEGylated liposomes are stable and are capable of delivery of an agent for the generation of an immune response. The PEGylation of the liposomes, where the PEGylated lipid is about 5000 Daltons or less, allows for stability of the liposome and allow for delivery to immune cells, for the generation of an immune response. As provided herein, the size of the PEGylated liposomes present in the composition ranges from about 1 nm to about 450 nm, and the size remains stable at varying temperatures, and over time. The PEGylated liposomes are stable and display little to no aggregation, or reduced aggregation, and are amenable to a terminal sterilization step prior to vialing. The PEGylated liposomes provided herein may further comprise a TLR agonist and/or an agent, for example an agent for vaccine, therapeutic, or diagnostic uses. Compositions and methods related to making and using the PEGylated liposomes for stimulating an immune response are also provided.

In one aspect, provided herein is a liposome comprising: (a) a cholesterol; (b) a non-PEGylated neutral lipid; and (c) a PEGylated lipid, wherein the average molecular weight of the PEG in the PEGylated lipid is about 5000 Daltons or less. In some embodiments, the average molecular weight of the PEG in the PEGylated lipid ranges from about 750 Daltons to about 5000 Daltons. In some embodiments, the average molecular weight of the PEG in the PEGylated lipid is about 2000 Daltons or less. In some embodiments, the average molecular weight of the PEG in the PEGylated lipid is about 750 Daltons. In some embodiments, the lipid component of the PEGylated lipid comprises a neutral lipid. In some embodiments, the lipid component of the PEGylated lipid comprises a C14 alkyl chain, a C16 alkyl chain, or a C18 alkyl chain. In some embodiments, the lipid component of the PEGylated lipid is DSPE, DPPC, DOPC, DLPC, DMPC, DSPC, POPC, DPPE, or DMPE. In some embodiments, the lipid component of the PEGylated lipid is DSPE. In some embodiments, the lipid component of the PEGylated lipid is DPPE. In some embodiments, the non-PEGylated neutral lipid comprises a C14 alkyl chain, a C16 alkyl chain, or a C18 alkyl chain. In some embodiments, the non-PEGylated neutral lipid is DPPC, DOPC, DLPC, DMPC, DSPC, POPC, DPPE, or DMPE. In some embodiments, the non-PEGylated neutral lipid is DPPC. In some embodiments, the liposome is stable. In some embodiments, the liposome is stable for at least 1 month at a temperature of about 2° C. to about 8° C. In some embodiments, the liposome is stable for at least 1 month at a temperature of about 25° C. In some embodiments, the liposome is stable for at least 1 month at a temperature of about 37° C. In some embodiments, the polydispersity index of the liposome is maintained at about 0.3 or less. In some embodiments, the size of the liposome is less than or about 450 nm. In some embodiments, the size of the liposome is maintained at less than or about 450 nm. In some embodiments, the size of the liposome ranges from about 50 nm to about 300 nm. In some embodiments, the polydispersity index of the liposome is less than or about 0.3. In some embodiments, the molar percentage (mol %) of the PEGylated lipid in the liposome ranges from about 1 mol % to about 25 mol %. In some embodiments, the mol % of the PEGylated lipid in the liposome ranges from about 1 mol % to about 10 mol %. In some embodiments, the mol % of the PEGylated lipid in the liposome is about 5 mol %. In some embodiments, the mol % of cholesterol in the liposome ranges from about 1 mol % to about 50 mol %. In some embodiments, the mol % of the cholesterol in the liposome is about 50 mol %. In some embodiments, the mol % of non-PEGylated lipid in the liposome ranges from about 45 mol % to about 98 mol %. In some embodiments, the mol % of non-PEGylated lipid in the liposome is about 45 mol %. In some embodiments, the lipid molar ratio of the non-PEGylated neutral lipid:cholesterol:PEGylated lipid is about 9.8:5.7:0.8. In some embodiments, the lipid molar ratio of the non-PEGylated neutral lipid:cholesterol:PEGylated lipid is about 18:5.5:3. In some embodiments, the liposome further comprises at least one TLR agonist. In some embodiments, the TLR agonist comprises a TLR2 agonist, a TLR3 agonist, a TLR4 agonist, a TLR5 agonist, a TLR6 agonist, a TLR7 agonist, a TLR8 agonist, a TLR7/8 agonist, or a TLR9 agonist. In some embodiments, the TLR agonist comprises TLR4, SLA, GLA, 3D-MPL, R837, or R848. In some embodiments, the TLR agonist comprises a hydrophobic tail. In some embodiments, the TLR agonist comprises a TLR7/8 agonist. In some embodiments, the TLR agonist comprises a TLR7 agonist. In some embodiments, the TLR agonist comprises a TLR8 agonist. In some embodiments, the TLR7/8 agonist comprises an imidazoquinoline or an imidazoquinoline-containing compound. In some embodiments, the TLR7/8 agonist comprises 3M-052. In some embodiments, the TLR7/8 agonist comprises R848. In some embodiments, the TLR agonist comprises a TLR4 agonist. In some embodiments, the TLR4 agonist comprises 3D-MPL. In some embodiments, the TLR4 agonist comprises GLA. In some embodiments, the TLR4 agonist comprises a synthetic GLA of Formula (V). In some embodiments, the TLR4 agonist comprises a synthetic GLA of Formula (VI).

In some embodiments, the TLR4 agonist comprises a synthetic GLA of formula:

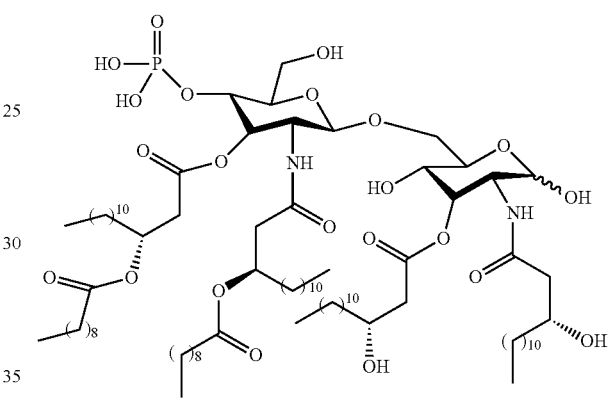

or a pharmaceutically acceptable salt thereof. In some embodiments, the liposome comprises a TLR4 agonist and a TLR7/8 agonist. In some embodiments, the liposome comprises GLA and 3M-052. In some embodiments, the liposome further comprises at least one agent. In some embodiments, the agent comprises a polypeptide, a polynucleotide, an antigen, an adjuvant, a diagnostic agent, a therapeutic agent, or an organism. In some embodiments, the agent comprises an antigen. In some embodiments, the antigen an amebiasis-related antigen. In some embodiments, the antigen comprises LecA. In some embodiments, the antigen comprises an influenza-related antigen. In some embodiments, the antigen comprises H5N1. In some embodiments, the antigen comprises a tuberculosis-related antigen. In some embodiments, the antigen comprises ID91. In some embodiments, the antigen comprises ID93. In some embodiments, the antigen comprises an antigen from BCG. In some embodiments, the antigen comprises a hepatitis virus-related antigen. In some embodiments, the antigen comprises a Hepatitis B antigen. In some embodiments, the antigen comprises a Hepatitis C antigen. In some embodiments, the antigen comprises a HIV-related antigen. In some embodiments, the antigen comprises a cancer-related antigen.

In a related aspect, provided herein is a composition comprising any one of the liposomes provided herein. In some embodiments, the composition comprises a pharmaceutically acceptable carrier, excipient, or diluent. In some embodiments, the composition is a vaccine. In some embodiments, the composition is a therapeutic. In some embodiments, the composition is a diagnostic.

In another aspect, provided herein is a method of stimulating an immune response in a subject, comprising administering to the subject any of the liposomes described herein, or any of the compositions comprising the liposomes described herein, whereby stimulating an immune response in the subject. In another aspect, provided herein is a method of inducing a Th1 response in a subject comprising administering to the subject the any of the liposomes described herein, or any of the compositions comprising the liposomes described herein, whereby a Th1 response is induced in the subject. In some embodiments, the immune response is a non-specific immune response. In some embodiments, the immune response is an antigen-specific immune response. In some embodiments, the immune response comprises a systemic immune response. In some embodiments, the immune response comprises a mucosal immune response. In some embodiments, the mucosal immune response comprises an intestinal, fecal, or vaginal mucosal immune response. In some embodiments, the composition is used for the treatment or prevention of cancer. In some embodiments, the composition is used as a vaccine. In some embodiments, the composition is used to enhance protective immunity against an influenza-causing virus. In some embodiments, the composition is used to enhance protective immunity against an amebiasis-causing organism. In some embodiments, the composition is used to enhance protective immunity against *Entamoeba histolytica*. In some embodiments, the composition is used to enhance protective immunity against influenza. In some embodiments, the composition is used to enhance protective immunity against amebiasis. In some embodiments, the route of administration of the composition is oral, topical, parenteral, sublingual, buccal, rectal, vaginal, intravenous, intradermal, transdermal, intranasal, intramucosal, or subcutaneous. In some embodiments, the route of administration is intranasal.

In another aspect, provided herein is a method of stimulating a systemic immune response and a mucosal immune response in a subject, comprising intranasally administering any one of the liposomes provided herein, or any one of the compositions comprising the liposomes, as provided herein, to the subject. In some embodiments, the method comprises administering a liposome that comprises a TLR4 agonist and a TLR7/8 agonist. In some embodiments, the method comprises administering a liposome that comprises GLA and 3M-052. In some embodiments, the mucosal immune response comprises an intestinal, fecal or vaginal mucosal immune response. In some embodiments, the mucosal immune response is distal to the nasal cavity.

In any of the methods described herein, the liposome or composition may be administered with a retinoic acid co-adjuvant.

In any of the methods described herein, the liposome or composition is administered to a human.

In any of the methods described herein, the liposome or composition is administered to a non-human mammal. In some embodiments, the non-human mammal is a dog, cow, or horse.

In another aspect, provided herein is a method of making any one of the PEGylated liposomes provided herein, comprising: (a) mixing the non-PEGylated neutral lipid, the PEGylated lipid, and the cholesterol in an organic solvent; (b) evaporating the organic solvent, whereby generating a lipid film; (c) rehydrating the lipid film in a buffer; and (d) sonicating, microfluidizing, or extruding the rehydrated product of step (c). In some embodiments, step (a) further comprises mixing a TLR agonist. In some embodiments, the organic solvent is chloroform. In some embodiments, the rehydrated product of step (c) is sonicated, and then microfluidized. In some embodiments, the method further comprises admixing an agent to the PEGylated liposome. In some embodiments, the agent comprises an antigen.

These and other aspects of the present invention will become evident upon reference to the following detailed description and attached drawings. In addition, various references are set forth herein which describe in more detail certain aspects of this invention, and are therefore incorporated by reference in their entireties.

BRIEF DESCRIPTION OF THE DRAWINGS

FIG. 1A depicts particle diameter, over time, at 5° C. FIG. 1B depicts the polydispersity index, over time, at 5° C. FIG. 1C depicts particle diameter, over time, at 37° C. FIG. 1D depicts the polydispersity index, over time, at 37° C.

FIGS. 3A-D depict LecA-specific cytokine response.

FIGS. 4A-B depict prechallenge mucosal IgA response and adherence inhibitory potential. Mice were immunized with GLA 3M-052 Liposome adjuvanted LecA using a mixed intranasal (weeks 0 and 4) and subcutaneous (week 2) regimen. Mice in the indicated groups received a weekly intraperitoneal injection of 150 mg all-trans retinoic acid (RA). Stool samples were collected three weeks post the third immunization. For FIG. 4A, fecal supernatants were diluted 120-folds and prechallenge anti-Lectin IgA titer was determined by ELISA; for FIG. 4B, potential of fecal IgA to inhibit adherence of trophozoites to mammalian cells was determined in vitro using adherence inhibition assay as described.

FIGS. 10A-B depict (a) Particle diameter and (b) size polydispersity index of representative formulations of 3M-052 at 5° C. for 6 months. Error bars represent standard deviation of three separate particle size assays from a single formulation batch at each timepoint. 3M-052 content was not measured for these batches but was estimated to be 0.04 mg/ml based on subsequent batches manufactured using the same process.

FIGS. 11A-H depict that mice immunized with 3M-052 show enhanced survival following H5N1 challenge. Animals were immunized once with rHA protein (A/VN/1203/04) in combination with adjuvants as indicated. Twenty one days post immunization, animals were challenged with $10^6$ PFU of A/VN/1203/04 (H5N1, Clade 1). Animals were monitored daily for survival (FIG. 11A) and weight loss (FIGS. 11B, 11C). 3 days (FIG. 11D) and 7 days (FIG. 11E) post-challenge, mice were euthanized, and lung virus titers determined by plaque assay. In addition, intact lungs were weighed at day 7 post-challenge as a measure of consolidation (11F), and were scored for the appearance of gross pathology (FIG. 11G). Significance was determined by Mantel-Cox Log-Rank Test (A) or by One-way ANOVA (FIGS. 11D-11G) ($p<0.005$, *$p<0.0005$, ****$p<0.0001$). FIG. 11H shows the lung virus titer.

FIGS. 12A-D depicts CD4 T-Cell responses in mice immunized with formulated 3M-052 Adjuvants. Animals were immunized once with rHA protein (A/VN/1203/04) in combination with adjuvants as indicated. Seven days post immunization, splenocytes from euthanized mice (n=5/group) were analyzed for cytokine stimulation following stimulation with rHA. Cytokine secretion patterns for IFNγ (I), TNFα (T), and IL-2 (2) were determined to investigate the induction of a Th1 CD4+ T-cell response. The relative percentage of polyfunctional t cells was also determined. Significance between groups was determined by one-way ANOVA (*$p<0.05$, **$p<0.005$).

FIGS. 14A-F depict induction of virus neutralizing titer by formulated 3M-052 adjuvants. Male Fitch ferrets were immunized once with a split H5N1 vaccine (SP-H5, Sanofi Pasteur) in combination with formulated 3M-052 adjuvants. Twenty one days post-immunization, blood was collected from all animals, and assayed for virus neutralizing antibodies using a retrovirus pseudotype neutralization assay. Inclusion of 3M-052 in adjuvant formulations resulted in significant (one-way ANOVA) increases in neutralizing titer against both homologous clade 1 virus (FIGS. A,D) as well as a clade 2 virus strain (FIGS. B,E) and a Clade 2.2 strain (FIGS. C,F).

DETAILED DESCRIPTION OF THE INVENTION

Figure 1A:
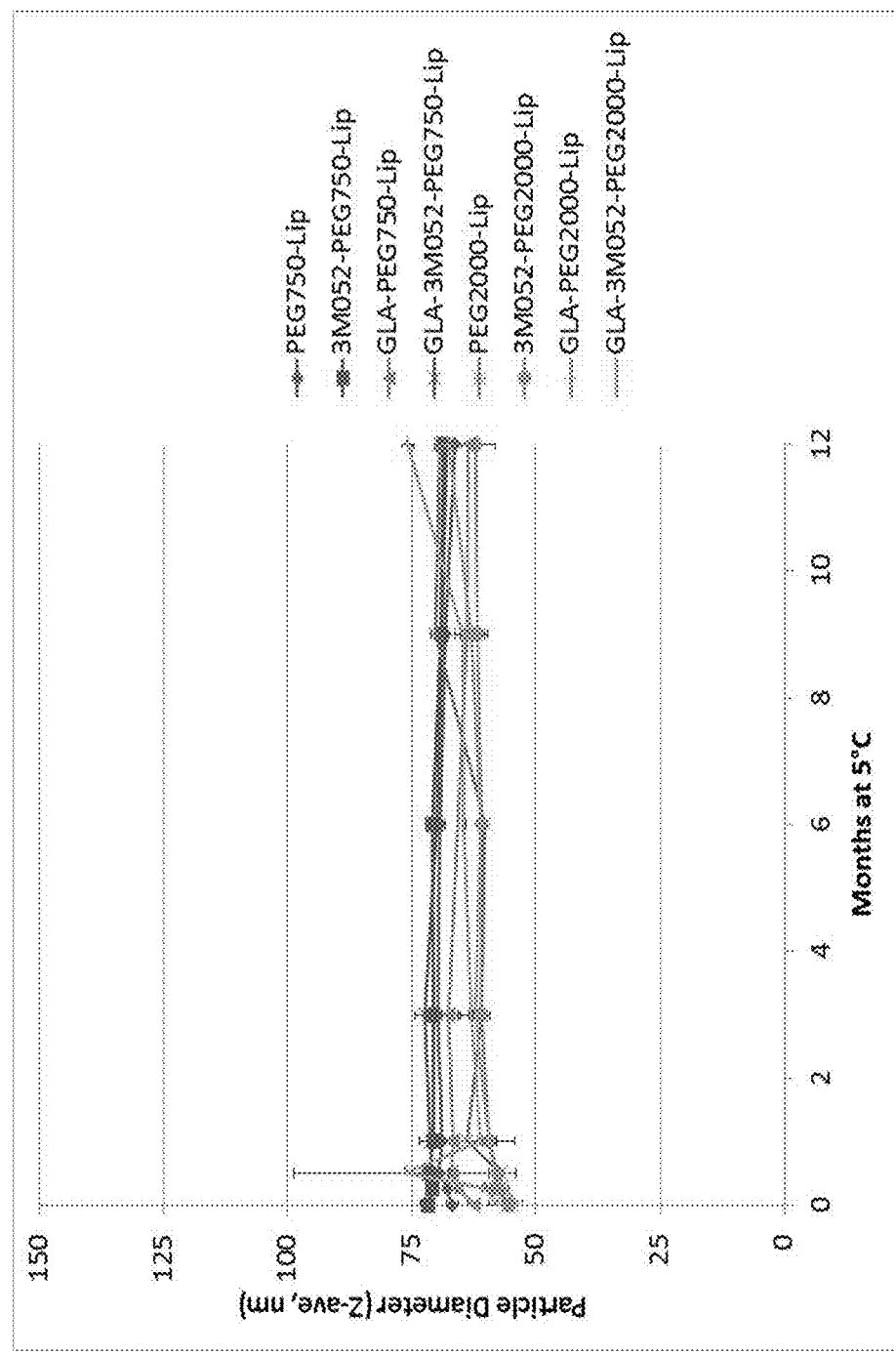
FIGS. 1A-1D depict physical and stability characteristics of various formulations.
Figure 1B:
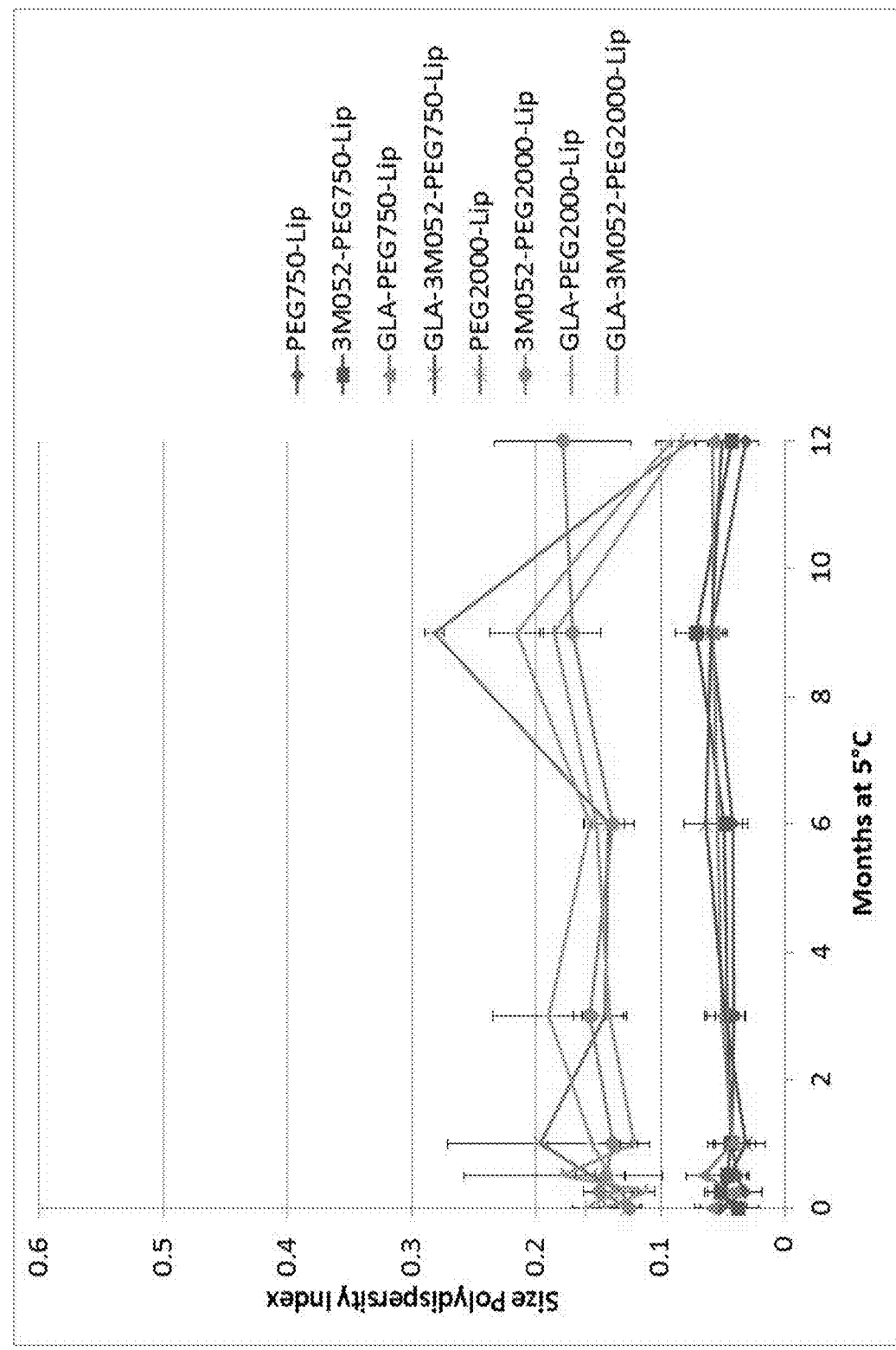

The present application is directed, inter alia, to PEGylated liposome formulations, compositions comprising the PEGylated liposomes, and methods of making and using the PEGylated liposomes. The inventors, while formulating an insoluble toll-like receptor (TLR) agonist, developed a liposome formulation that is surprisingly versatile at incorporating various TLR ligands and/or antigens while maintaining stability and that is effective at enhancing immune response when mixed with antigen. The inventors found that a variety of different antigens when mixed with these liposomes resulted in antigen-liposome formulations capable of administration to a mammal. The liposome formulations comprise a cholesterol, a non-PEGylated neutral lipid, and a PEGylated lipid, wherein the average molecular weight of the PEG in the PEGylated lipid is about 5000 daltons or less, preferably from about 750 to about 5000 daltons, or from 750 to about 2000 daltons. The use of the PEGylated lipids provides stability, and allows for the delivery and generation/stimulation/modification of an immune response. In some preferred embodiments, the non-PEGylated neutral lipid is DPPC and the PEGylated lipid is PEGylated DSPE or DPPE. In some particularly preferred embodiments, the liposomes further comprise a toll-like receptor (TLR) agonist and optionally, an antigen.

Compositions (such as vaccine compositions, pharmaceutical compositions) comprising the PEGylated liposomes described herein are also provided. The compositions are useful for generating/stimulating/modifying an immune response in a subject. In some embodiments, the composition described herein further comprises one or more antigens and/or TLR agonists.

The inventors also found, when formulating squalene-based oil-in-water emulsions of the insoluble toll-like receptor 3M-052, emulsions manufactured with egg phosphatidylcholine or POPC instead of DMPC resulted in higher recovery of the toll-like receptor after processing. Further, adding an initial mixing step of combining the toll-like receptor with egg phosphatidylcholine or POPC in chloroform further increased recovery of the toll-like receptor. The present application is also directed, inter alia, to squalene-based oil-in-water emulsions comprising squalene, unsaturated phosphatidylcholine, and a toll-like receptor (e.g., an insoluble toll-like receptor) and methods of making such emulsions by mixing the toll-like receptor with unsaturated phosphatidylcholine in chloroform.

I. Definitions

The following terms have the following meanings unless otherwise indicated. Any undefined terms have their art recognized meanings.

In the present description, the terms "about" and "consisting essentially of" mean±20% of the indicated range, value, or structure, unless otherwise indicated.

The use of the alternative (e.g., "or") should be understood to mean either one, both, or any combination thereof of the alternatives.

As used herein, the terms "include," "have" and "comprise" are used synonymously, which terms and variants thereof are intended to be construed as non-limiting.

As used herein and in the appended claims, the singular forms "a," "an," and "the" include plural reference unless the context clearly indicates otherwise.

The term "macromolecule" as used herein refers to large molecules exemplified by, but not limited to, peptides, proteins, oligonucleotides and polynucleotides of biological or synthetic origin.

The terms "polypeptide", "peptide", and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

The term "isolated" means the molecule has been removed from its natural environment.

"Purified" means that the molecule has been increased in purity, such that it exists in a form that is more pure than it exists in its natural environment and/or when initially synthesized and/or amplified under laboratory conditions. Purity is a relative term and does not necessarily mean absolute purity.

A "polynucleotide" or "nucleic acid," as used interchangeably herein, refer to polymers of nucleotides of any length, include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

An "individual" or a "subject" is any mammal. Mammals include, but are not limited to humans, primates, farm animals, sport animals, pets (such as cats, dogs, horses), and rodents.

"Alkyl" is a straight or branched saturated hydrocarbon. For example, an alkyl group can have 1 to 30 carbon atoms (i.e., ($C_1$-$C_{30}$)alkyl) or 1 to 20 carbon atoms (i.e., ($C_1$-$C_{20}$ alkyl) or 1 to 10 carbon atoms (i.e., ($C_1$-$C_{10}$)alkyl) or 1 to 8 carbon atoms (i.e., ($C_1$-$C_8$)alkyl) or 1 to 6 carbon atoms (i.e., ($C_1$-$C_6$)alkyl) or 1 to 4 carbon atoms (i.e., ($C_1$-$C_4$)alkyl). This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), neopentyl (($CH_3$)$_3$CCH$_2$—), and n-hexyl ($CH_3(CH_2)_5$—).

"Halo" or "halogen" refers to fluoro, chloro, bromo, and iodo.

"Hydroxy" or "hydroxyl" refers to the group —OH.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like.

"Carboxyl ester" or "carboxy ester" refers to the groups —C(O)O-alkyl and —C(O)O-substituted alkyl, wherein alkyl and substituted alkyl are as defined herein.

The practice of the present invention will employ, unless otherwise indicated, conventional techniques of molecular biology, recombinant DNA, biochemistry, and chemistry, which are within the skill of the art. Such techniques are explained fully in the literature. See, e.g., Molecular Cloning A Laboratory Manual, 2nd Ed., Sambrook et al., ed., Cold Spring Harbor Laboratory Press: (1989); DNA Cloning, Volumes I and II (D. N. Glover ed., 1985); Oligonucleotide Synthesis (M. J. Gait ed., 1984); Mullis et al., U.S. Pat. No. 4,683,195; Nucleic Acid Hybridization (B. D. Hames & S. J. Higgins eds. 1984); B. Perbal, A Practical Guide To Molecular Cloning (1984); the treatise, Methods In Enzymology (Academic Press, Inc., N.Y.); and in Ausubel et al., Current Protocols in Molecular Biology, John Wiley and Sons, Baltimore, Maryland (1989).

As used herein, "insoluble in water" refers to a compound that does not dissolve or dissolves to a negligible level when the compound is mixed with water, for example, when mixed with water at room temperature, for example, between or between about 25° C. and 50° C.

II. PEGylated Liposomes

The present disclosure provides PEGylated liposomes comprising at least a cholesterol, a non-PEGylated neutral lipid, and a PEGylated lipid, wherein the average molecular weight of the PEG component in the PEGylated lipid is about 5000 Daltons or less. The PEGylated liposomes provided herein may further comprise an agent, for example an agent for vaccine, therapeutic, or diagnostic uses. The PEGylated liposomes provided herein may further comprise a TLR agonist, for example for the above mentioned vaccine, therapeutic, or diagnostic uses. Description of each individual component of the PEGylated liposomes and characteristics of the PEGylated liposomes are described below.

A. PEGylated Lipids

The PEGylated liposomes provided herein comprise PEGylated lipids (lipids linked to a polyethylene glycol (PEG)), wherein the average molecular weight of the PEG in the PEGylated lipid is about 5000 Daltons or less. It was recognized that use of such lipids linked to PEG in combination with a neutral non-PEGylated lipid and a cholesterol confers stability to an otherwise neutral liposome that does not contain PEGylated lipids. The use of such PEGylated lipids allows for long-term stability of the PEGylated liposome structure and allows for the effective stimulation of an immune response.

Characteristics of the PEG in the PEGylated Lipid

In the embodiments contemplated herein, the average molecular weight of the PEG in the PEGylated lipid is about 5000 Daltons or less. In some embodiments the average molecular weight of the PEG in the PEGylated lipid is about 2000 Daltons or less. In particular embodiments, the average molecular weight of the PEG ranges from about 750 Daltons to about 5000 Daltons. In particular embodiments, the average molecular weight of the PEG ranges from about 750 Daltons to about 2000 Daltons. In some embodiments, the average molecular weight of the PEG ranges from about 750 to 1000; 750 to 1500; 750 to 2000; 750 to 2500; 750 to 3000; 750 to 3500; 750 to 4000; 750 to 4500; or 750 to 5000 Daltons. In some embodiments, the average molecular weight of the PEG ranges from about 4500 to 5000; 4000 to 5000; 3500 to 5000; 3000 to 5000; 2500 to 5000; 2000 to 5000; 1500 to 5000; 1000 to 5000; or 750 to 5000 Daltons. In some embodiments, the average molecular weight of the PEG ranges from about 500 to 1000; 500 to 750; or 750 to 1000 Daltons. In some embodiments, the average molecular weight of the PEG ranges from about 1500 to 2500; 1500 to 2000; or 2000 to 2500 Daltons. In some embodiments, the average molecular weight of the PEG ranges from about 4500 to 5500; 4500 to 5000; or 2000 to 5000 Daltons.

In one exemplary embodiment, PEGylated lipid comprises PEG750. In another exemplary embodiment, PEGylated lipid comprises PEG1000. In another exemplary embodiment, PEGylated lipid comprises PEG1500. In another exemplary embodiment, PEGylated lipid comprises PEG2000. In another exemplary embodiment, PEGylated lipid comprises PEG2500. In another exemplary embodiment, PEGylated lipid comprises PEG3000. In another exemplary embodiment, PEGylated lipid comprises PEG3500. In another exemplary embodiment, PEGylated lipid comprises PEG4000. In another exemplary embodiment, PEGylated lipid comprises PEG4500. In another exemplary embodiment, PEGylated lipid comprises PEG5000.

Characteristics of the Lipid in the PEGylated Lipid

It is contemplated herein that the lipid component of the PEGylated lipid can comprise any lipid (which includes phospholipids) that can associate with the cholesterol and the non-PEGylated neutral lipid components to form a stable liposome structure.

Table 1 provides a non-limiting list of exemplary lipids which can be linked to the PEG for use in the invention.

TABLE 1

Exemplary Lipids

Polysorbate 80

$w + x + y + z = 20$

DLPC

DMPC

DPPC

DSPC

DOPC

TABLE 1-continued

Exemplary Lipids

- POPC
- DLPG
- DMPG
- DPPG
- DSPG
- DOPG
- DSTAP
- DPTAP
- DSPE

TABLE 1-continued

Exemplary Lipids

DPPE

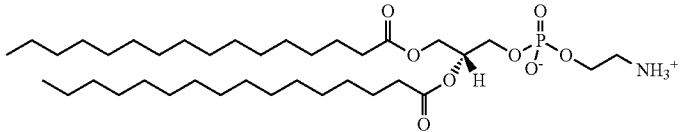 [SMILES: CCCCCCCCCCCCCCCC(=O)OC[C@H](COP(=O)([O-])OCC[NH3+])OC(=O)CCCCCCCCCCCCCCC]

DMPE

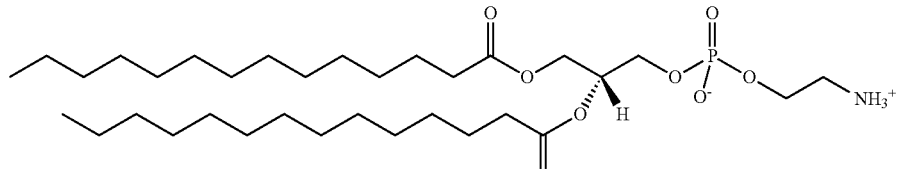

DLPE

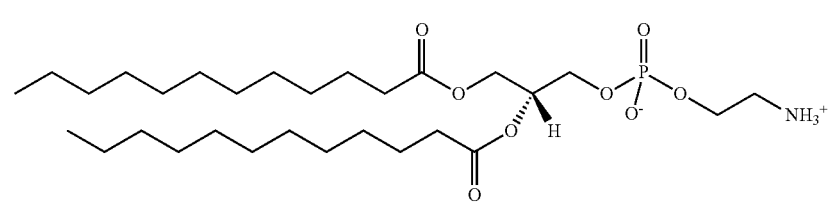 [SMILES: CCCCCCCCCCCC(=O)OC[C@H](COP(=O)([O-])OCC[NH3+])OC(=O)CCCCCCCCCCC]

In certain embodiments, the lipid component of the PEGylated lipid is a phospholipid or a quaternary ammonium salt lipid. In certain embodiments, the lipid component of the PEGylated lipid is a phospholipid that is a phosphatidylcholine or a phosphoglyceride. In certain embodiments, the lipid component of the PEGylated lipid comprises any of the following moieties:

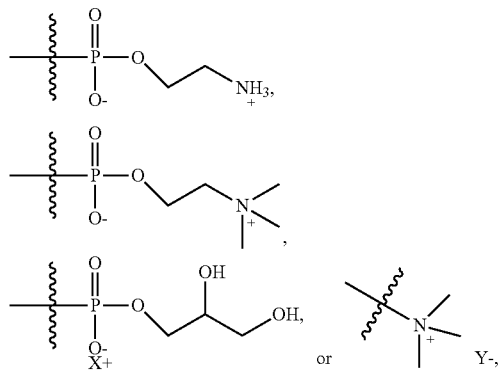

wherein $X^-$ is an alkali metal counterion and $Y^+$ is a halide counterion.

In certain embodiments, the lipid component of the PEGylated lipid comprises a $C_{10-20}$ alkyl chain. In certain embodiments, the lipid component of the PEGylated lipid comprises a $C_{12-18}$ alkyl chain. In some embodiments, the lipid component of the PEGylated lipid comprises a $C_{14}$ alkyl chain, a $C_{16}$ alkyl chain, or a $C_{18}$ alkyl chain.

In certain embodiments, the lipid component of the PEGylated lipid is anionic. In certain embodiments, the lipid component of the PEGylated lipid is cationic. In certain embodiments, the lipid component of the PEGylated lipid is overall neutrally charged. In certain embodiments, the lipid component of the PEGylated lipid is a zwitterion.

In certain exemplary embodiments, the lipid component of the PEGylated lipid is DPPC, DOPC, DLPC, DMPC, DSPC, POPC, DSPE, DPPE, or DMPE. In one exemplary embodiment, the lipid component of the PEGylated lipid is DSPE. In another exemplary embodiment, the lipid component of the PEGylated lipid is DPPE. In another exemplary embodiment, the lipid component of the PEGylated lipid is DMPE.

In any of the embodiments described herein, the lipid component of the PEGylated lipid can be DLPE.

In certain embodiments, the molar percentage (mol %) of the PEGylated lipid in the liposome ranges from about 1 mol % to about 25 mol %. In certain embodiments, the molar percentage (mol %) of the PEGylated lipid in the liposome is about 1 mol %, 2 mol %, 3 mol %, 4 mol %, 5 mol %, 6 mol %, 7 mol %, 8 mol %, 9 mol %, 10 mol %, 11 mol %, 12 mol %, 13 mol %, 14 mol %, 15 mol %, 16 mol %, 17 mol %, 18 mol %, 19 mol %, 20 mol %, 21 mol %, 22 mol %, 23 mol %, 24 mol %, or even about 25 mol %. In an exemplary embodiment, the mol % of the PEGylated lipid in the liposome is about 5 mol %. In another exemplary embodiment, the mol % of the PEGylated lipid in the liposome is about 10 mol %. In another exemplary embodiment, the mol % of the PEGylated lipid in the liposome is about 15 mol %. In another exemplary embodiment, the mol % of the PEGylated lipid in the liposome is about 20 mol %. In another exemplary embodiment, the mol % of the PEGylated lipid in the liposome is about 25 mol %.

Exemplary PEGylated Lipids

In certain embodiments, the PEGylated lipid in the PEGylated liposome is DSPE-PEG750, DSPE-PEG1000, DSPE-PEG1500, DSPE-PEG2000, DSPE-PEG2500, DSPE-PEG3000, DSPE-PEG3500, DSPE-PEG4000, DSPE-PEG4500 or DSPE-PEG5000.

In certain embodiments, the PEGylated lipid in the PEGylated liposome is DPPE-PEG750, DPPE-PEG1000, DPPE-PEG1500, DPPE-PEG2000, DPPE-PEG2500, DPPE-PEG3000, DPPE-PEG3500, DPPE-PEG4000, DPPE-PEG4500 or DPPE-PEG5000.

In certain embodiments, the PEGylated lipid in the PEGylated liposome is DMPE-PEG750, DMPE-PEG1000, DMPE-PEG1500, DMPE-PEG2000, DMPE-PEG2500, DMPE-PEG3000, DMPE-PEG3500, DMPE-PEG4000, DMPE-PEG4500 or DMPE-PEG5000.

In certain embodiments, the PEGylated lipid in the PEGylated liposome is DPPC-PEG750, DPPC-PEG1000, DPPC-PEG1500, DPPC-PEG2000, DPPC-PEG2500, DPPC-PEG3000, DPPC-PEG3500, DPPC-PEG4000, DPPC-PEG4500 or DPPC-PEG5000.

In certain embodiments, the PEGylated lipid in the PEGylated liposome is DOPC-PEG750, DOPC-PEG1000, DOPC-PEG1500, DOPC-PEG2000, DOPC-PEG2500, DOPC-PEG3000, DOPC-PEG3500, DOPC-PEG4000, DOPC-PEG4500 or DOPC-PEG5000.

In certain embodiments, the PEGylated lipid in the PEGylated liposome is DLPC-PEG750, DLPC-PEG1000, DLPC-PEG1500, DLPC-PEG2000, DLPC-PEG2500, DLPC-PEG3000, DLPC-PEG3500, DLPC-PEG4000, DLPC-PEG4500 or DLPC-PEG5000.

In certain embodiments, the PEGylated lipid in the PEGylated liposome is DMPC-PEG750, DMPC-PEG1000, DMPC-PEG1500, DMPC-PEG2000, DMPC-PEG2500, DMPC-PEG3000, DMPC-PEG3500, DMPC-PEG4000, DMPC-PEG4500 or DMPC-PEG5000.

In certain embodiments, the PEGylated lipid in the PEGylated liposome is POPC-PEG750, POPC-PEG1000, POPC-PEG1500, POPC-PEG2000, POPC-PEG2500, POPC-PEG3000, POPC-PEG3500, POPC-PEG4000, POPC-PEG4500 or POPC-PEG5000.

In certain embodiments, the PEGylated lipid in the PEGylated liposome is DSPC-PEG750, DSPC-PEG1000, DSPC-PEG1500, DSPC-PEG2000, DSPC-PEG2500, DSPC-PEG3000, DSPC-PEG3500, DSPC-PEG4000, DSPC-PEG4500 or DSPC-PEG5000.

B. Non-PEGylated Neutral Lipids

The PEGylated liposomes provided herein also comprise non-PEGylated neutral lipids (neutral lipids not linked to a polyethylene glycol (PEG)). It is contemplated herein that the non-PEGylated neutral lipid component of the liposome comprise any neutral lipid (which includes neutral phospholipids) that carries an overall neutral charge, or is zwitterionic, that can associate with the PEGylated lipid component to form a stable liposome structure.

As provided herein, the non-PEGylated neutral lipid is overall neutrally charged. In certain embodiments, the non-PEGylated neutral lipid is a zwitterion. A neutral non-PEGylated lipid component of the PEGylated liposome, in some variations, can render the PEGylated liposome to be overall neutrally charged.

In certain embodiments, the non-PEGylated neutral lipid component of the PEGylated liposome comprises a $C_{10-20}$ alkyl chain. In certain embodiments, the non-PEGylated neutral lipid component comprises a $C_{12-18}$ alkyl chain. In some embodiments, the non-PEGylated neutral lipid component comprises a $C_{14}$ alkyl chain, a $C_{16}$ alkyl chain, or a $C_{18}$ alkyl chain.

In some embodiments, the non-PEGylated neutral lipid is DPPC, DOPC, DLPC, DMPC, DSPC, POPC, DPPE, or DMPE.

In certain embodiments, the molar percentage (mol %) of the non-PEGylated neutral lipid in the liposome ranges from about 45 mol % to about 98 mol %. In certain embodiments, the molar percentage (mol %) of the non-PEGylated neutral lipid in the liposome is about 45 mol %, 50 mol %, 55 mol %, 60 mol %, 65 mol %, 70 mol %, 75 mol %, 80 mol %, 85 mol %, 90 mol %, 95 mol %, or even about 98 mol %. In an exemplary embodiment, the mol % of the non-PEGylated neutral lipid in the liposome is about 45 mol %.

In an exemplary embodiment, the lipid molar ratio of the non-PEGylated neutral lipid to the PEGylated lipid is 9.8:0.8. In an exemplary embodiment, the lipid molar ratio of the non-PEGylated neutral lipid to the PEGylated lipid is 18:3.

In an exemplary embodiment, the lipid molar ratio of the non-PEGylated neutral lipid DPPC to the PEGylated lipid DPPE-PEG2000 is 9.8:0.8. In an exemplary embodiment, the lipid molar ratio of the non-PEGylated neutral lipid DPPC to the PEGylated lipid DPPE-PEG750 is 9.8:0.8. In an exemplary embodiment, the lipid molar ratio of the non-PEGylated neutral lipid DPPC to the PEGylated lipid DPPE-PEG750 is 18:3.

C. Cholesterol

The PEGylated liposomes provided herein comprise a cholesterol (which includes cholesterol-containing compounds).

In some embodiments, the mol % of cholesterol in the PEGylated liposome ranges from about 1 mol % to about 50 mol %, from about 5 mol % to about 50 mol %, from about 10 mol % to about 50 mol %, from about 20 mol % to about 50 mol %, from about 25 mol % to about 50 mol %, from about 5 mol % to about 10 mol %, from about 5 mol % to about 20 mol %, from about 5 mol % to about 25 mol %, from about 10 mol % to about 20 mol %, from about 10 mol % to about 25 mol %, from about 20 mol % to about 30 mol %, from about 20 mol % to about 40 mol %, or even from about 1 mol % to about 10 mol %. In some embodiments, the mol % of the cholesterol in the PEGylated liposome is about 50 mol %. In some embodiments, the mol % of the cholesterol in the PEGylated liposome is about 45 mol %. In some embodiments, the mol % of the cholesterol in the PEGylated liposome is about 40 mol %. In some embodiments, the mol % of the cholesterol in the PEGylated liposome is about 35 mol %. In some embodiments, the mol % of the cholesterol in the PEGylated liposome is about 30 mol %. In some embodiments, the mol % of the cholesterol in the PEGylated liposome is about 25 mol %. In some embodiments, the mol % of the cholesterol in the PEGylated liposome is about 20 mol %. In some embodiments, the mol % of the cholesterol in the PEGylated liposome is about 15 mol %. In some embodiments, the mol % of the cholesterol in the PEGylated liposome is about 10 mol %. In some embodiments, the mol % of the cholesterol in the PEGylated liposome is about 5 mol %.

In certain embodiments the lipid molar ratio of the cholesterol to non-PEGylated neutral lipid to the PEGylated lipid is about 5.7:9.8:0.8. In certain embodiments the lipid molar ratio of the cholesterol to non-PEGylated neutral lipid to the PEGylated lipid is about 5.5:18:3.

In certain embodiments the lipid molar ratio of the cholesterol to non-PEGylated neutral lipid DPPC to the PEGylated lipid DPPE-PEG2000 is about 5.7:9.8:0.8. In certain embodiments the lipid molar ratio of the cholesterol to non-PEGylated neutral lipid DPPC to the PEGylated lipid DPPE-PEG750 is about 5.7:9.8:0.8. In certain embodiments the lipid molar ratio of the cholesterol to non-PEGylated neutral lipid DPPC to the PEGylated lipid DPPE-PEG750 is about 5.5:18:3.

D. TLR Agonists

As described herein, the PEGylated liposomes described herein may comprise one or more toll-like receptor agonists (TLR agonists). Toll-like receptors (TLR) include cell surface transmembrane receptors of the innate immune system that confer early-phase recognition capability to host cells for a variety of conserved microbial molecular structures such as may be present in or on a large number of infectious pathogens. Induction of TLR-mediated signal transduction to potentiate the initiation of immune responses via the innate immune system may be effected by TLR agonists, which engage cell surface TLR. For example, lipopolysaccharide (LPS) may be a TLR agonist through TLR2 or TLR4 (Tsan et al., 2004 *J. Leuk. Biol.* 76:514; Tsan et al., 2004 *Am. J. Physiol. Cell Phsiol.* 286:C739; Lin et al., 2005 Shock 24:206); poly(inosine-cytidine) (polyI:C) may be a TLR agonist through TLR3 (Salem et al., 2006 *Vaccine* 24:5119); CpG sequences (oligodeoxynucleotides containing unmethylated cytosine-guanosine or "CpG" dinucleotide motifs, e.g., CpG 7909, Cooper et al., 2005 AIDS 19:1473; CpG 10101 Bayes et al. *Methods Find Exp Clin Pharmacol* 27:193; Vollmer et al. *Expert Opinion on Biological Therapy* 5:673; Vollmer et al., 2004 *Antimicrob. Agents Chemother.* 48:2314; Deng et al., 2004 *J. Immunol.* 173:5148) may be TLR agonists through TLR9 (Andaloussi et a., 2006 Glia 54:526; Chen et al., 2006 *J. Immunol.* 177:2373); peptidoglycans may be TLR2 and/or TLR6 agonists (Soboll et al., 2006 *Biol. Reprod.* 75:131; Nakao et al., 2005 *J. Immunol.* 174:1566); 3M003 (4-amino-2-(ethoxymethyl)-α,α-dimethyl-6,7,8,9-tetrahydro-1H-imidazo[4,5-c]quinoline-1-ethanol hydrate, Mol. Wt. 318 Da from 3M Pharmaceuticals, St. Paul, MN, which is also a source of the related compounds 3M001 and 3M002; Gorden et al., 2005 *J. Immunol.* 174:1259) may be a TLR7 agonist (Johansen 2005 *Clin. Exp. Allerg.* 35:1591) and/or a TLR8 agonist (Johansen 2005); flagellin may be a TLR5 agonist (Feuillet et al., 2006 *Proc. Nat. Acad. Sci. USA* 103:12487); and hepatitis C antigens may act as TLR agonists through TLR7 and/or TLR9 (Lee et al., 2006 *Proc. Nat. Acad. Sci. USA* 103:1828; Horsmans et al., 2005 *Hepatol.* 42:724). Other TLR agonists are known (e.g., Schirmbeck et al., 2003 *J. Immunol.* 171: 5198) and may be used according to certain of the presently described embodiments.

In various embodiments, the TLR agonist may be a TLR2 agonist, TLR3 agonist, TLR4 agonist, TLR5 agonist, TLR6 agonist, TLR7 agonist, TLR8 agonist, TLR7/8 agonist, TLR9 agonist, combinations thereof.

TLR7/8 Agonists

Provided herein are TLR7/8 agonists that can be used in the compositions described herein. As used herein, a "TLR7/8 agonist" refers to an agonist that affects its biological activities through its interaction with TLR7, TLR8, or both. Such biological activities include, but are not limited to, the induction of TLR7 and/or TLR8 mediated signal transduction to potentiate immune responses via the innate immune system. In some embodiments, the TLR is an imidazoquinoline, an imidazoquinoline containing compound, or an imidazoquinoline amine derivative (see, e.g., U.S. Pat. No. 4,689,338 (Gerster)), but other compound classes are known as well (see, e.g., U.S. Pat. No. 5,446,153 (Lindstrom et al.); U.S. Pat. No. 6,194,425 (Gerster et al.); and U.S. Pat. No. 6,110,929 (Gerster et al.); and International Publication Number WO2005/079195 (Hays et al.)).

In certain embodiments, a TLR7/8 agonist used in the compositions described herein comprises an imidazoquinoline derivative, such as those described in Shi et al. (*ACS Med. Chem. Lett.*, 2012, 3(6), pp. 501-504), the contents of which is incorporated herein by reference in its entirety.

In some embodiments, the TLR7/8 comprises an imidazoquinoline or an imidazoquinoline-containing compound. In some embodiments the imidazoquinoline is imiquimod (referred to as IMQ or R837), an immune response modifier. In some embodiments the imidazoquinoline is resiquimod (R848), a drug that acts as an immune response modifier (Tomai M A, Miller R L, Lipson K E, Kieper W C, Zarraga I E, Vasilakos J P (October 2007). "Resiquimod and other immune response modifiers as vaccine adjuvants". Expert Review of Vaccines 6 (5): 835-47.) In certain embodiments, the TLR 7/8 agonist is CL075.

For example, in certain embodiments, the TLR7/8 agonist is a compound of following structure of Formula (I):

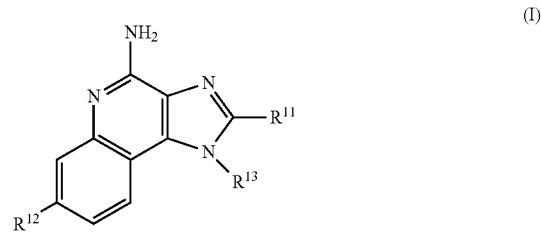

or a pharmaceutically acceptable salt thereof, wherein:

$R^{11}$ is selected from the group consisting of hydrogen and $C_{1-6}$alkyl, wherein the $C_{1-6}$alkyl is optionally substituted with one or more groups selected from the group consisting of halo, hydroxyl, and $C_{1-6}$ alkoxy;

$R^{12}$ is selected from the group consisting of hydrogen and carboxyl ester; and $R^{13}$ is selected from the group consisting of hydrogen and $C_{1-6}$alkyl, wherein the $C_{1-6}$alkyl is optionally substituted with one or more groups selected from the group consisting of halo, hydroxyl, and $C_{1-6}$ alkoxy.

In some embodiments of Formula (I), $R^{11}$ is hydrogen. In some embodiments, $R^{11}$ is $C_{1-6}$alkyl. In some embodiments, $R^{11}$ is methyl, ethyl, n-propyl, or n-butyl. In some embodiments, $R^{11}$ is n-butyl. In some embodiments, $R^{11}$ is $C_{1-6}$alkyl, which is substituted $C_{1-6}$alkoxy. In some embodiments, $R^{11}$ is —$CH_2$—O—$CH_2$—$CH_3$.

In some embodiments of Formula (I), $R^{12}$ is hydrogen. In some embodiments, $R^{12}$ is carboxyl ester. In some embodiments, $R^{12}$ is —C(O)O—$C_{1-4}$ alkyl. In some embodiments, $R^{12}$ is —C(O)O—$CH_3$.

In some embodiments of Formula (I), $R^{13}$ is $C_{1-6}$alkyl. In some embodiments, $R^{13}$ is $C_{2-4}$alkyl. In some embodiments, $R^{13}$ is —$CH_2$—$CH(CH_3)_2$.

In some embodiments, $R^{13}$ is $C_{1-6}$alkyl, which is substituted with halo, hydroxyl, or $C_{1-6}$alkoxy. In some embodiments, $R^{13}$ is $C_{1-6}$alkyl, which is substituted with hydroxyl. In some embodiments, $R^{13}$ is $C_{2-4}$ alkyl, which is substituted with hydroxyl. In some embodiments, $R^{13}$ is —$CH_2$—C$(CH_3)_2$OH.

In certain embodiments, the TLR7/8 agonist is a compound of following structure of Formula (II):

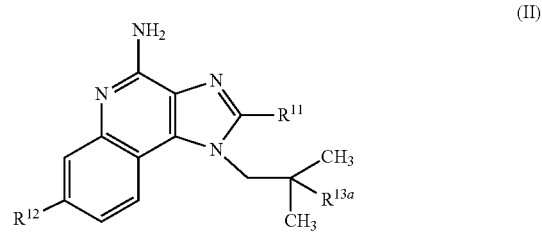

or a pharmaceutically acceptable salt thereof, wherein:

$R^{11}$ is selected from the group consisting of hydrogen and $C_{1-6}$alkyl, wherein the $C_{1-6}$alkyl is optionally substituted with one or more groups selected from the group consisting of halo, hydroxyl, and $C_{1-6}$ alkoxy;

$R^{12}$ is selected from the group consisting of hydrogen and carboxyl ester; and $R^{13a}$ is selected from the group consisting of hydrogen and hydroxyl.

In some embodiments of Formula (II), $R^{11}$ is hydrogen. In some embodiments, $R^{11}$ is $C_{1-6}$alkyl. In some embodiments, $R^{11}$ is methyl, ethyl, n-propyl, or n-butyl. In some embodiments, $R^{11}$ is n-butyl. In some embodiments, $R^{11}$ is $C_{1-6}$alkyl, which is substituted $C_{1-6}$alkoxy. In some embodiments, $R^{11}$ is —$CH_2$—O—$CH_2$—$CH_3$.

In some embodiments of Formula (II), $R^{12}$ is hydrogen. In some embodiments, $R^{12}$ is carboxyl ester. In some embodiments, $R^{12}$ is —C(O)O—$C_{1-4}$ alkyl. In some embodiments, $R^{12}$ is —C(O)O—$CH_3$.

In some embodiments of Formula (II), $R^{13a}$ is hydroxyl. In some embodiments, $R^{13a}$ is hydrogen.

In certain embodiments, the TLR7/8 agonist is a compound of following structure of Formula (III):

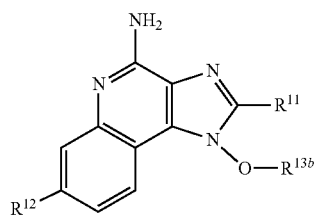

(III)

or a pharmaceutically acceptable salt thereof, wherein:

$R^{11}$ is selected from the group consisting of hydrogen and $C_{1-6}$alkyl, wherein the $C_{1-6}$alkyl is optionally substituted with one or more groups selected from the group consisting of halo, hydroxyl, and $C_{1-6}$ alkoxy;

$R^{12}$ is selected from the group consisting of hydrogen and carboxyl ester; and $R^{13b}$ is $C_{1-6}$alkyl optionally substituted with one or more groups selected from the group consisting of halo, hydroxyl, $C_{1-6}$alkoxy, and acylamino.

In some embodiments of Formula (III), $R^{11}$ is hydrogen. In some embodiments, $R^{11}$ is $C_{1-6}$alkyl. In some embodiments, $R^{11}$ is methyl, ethyl, n-propyl, or n-butyl. In some embodiments, $R^{11}$ is n-butyl. In some embodiments, $R^{11}$ is $C_{1-6}$alkyl, which is substituted $C_{1-6}$alkoxy. In some embodiments, $R^{11}$ is —$CH_2$—O—$CH_2$—$CH_3$.

In some embodiments of Formula (III), $R^{12}$ is hydrogen. In some embodiments, $R^{12}$ is carboxyl ester. In some embodiments, $R^{12}$ is —C(O)O—$C_{1-4}$ alkyl. In some embodiments, $R^{12}$ is —C(O)O—$CH_3$.

In some embodiments of Formula (III), $R^{13b}$ is $C_{2-4}$alkyl, which is substituted with acylamino. In some embodiments, $R^{13b}$ is —$(CH_2)_4$-acylamino. In some embodiments, $R^{13b}$ is —$(CH_2)_4$—NH—C(O)—$C_{1-25}$alkyl. In some embodiments, $R^{13b}$ is —$(CH_2)_4$—NH—C(O)—$C_{15-25}$alkyl. In some embodiments, $R^{13b}$ is —$(CH_2)_4$—NH—C(O)—$C_{15-20}$alkyl. In some embodiments, $R^{13b}$ is —$(CH_2)_4$—NH—C(O)—$C_{17}$alkyl.

In certain embodiments, the TLR7/8 agonist is a compound of following structure of Formula (IV):

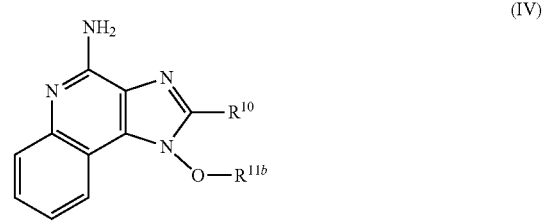

(IV)

or a pharmaceutically acceptable salt thereof, wherein:

$R^{10}$ is selected from the group consisting of hydrogen and $C_{1-6}$alkyl; and $R^{11b}$ is $C_{1-6}$alkyl optionally substituted with one or more groups selected from the group consisting of halo, hydroxyl, $C_{1-6}$alkoxy, and acylamino.

In some embodiments of Formula (IV), $R^{10}$ is hydrogen. In some embodiments, $R^{10}$ is $C_{1-6}$alkyl. In some embodiments, $R^{10}$ is methyl, ethyl, n-propyl, or n-butyl. In some embodiments, $R^{10}$ is n-butyl.

In some embodiments of Formula (IV), $R^{a}b$ is $C_{2-4}$alkyl, which is substituted with acylamino. In some embodiments, $R^{a}b$ is —$(CH_2)_4$-acylamino. In some embodiments, $R^{a}b$ is —$(CH_2)_4$—NH—C(O)—$C_{1-25}$alkyl. In some embodiments, Rib is —$(CH_2)_4$—NH—C(O)—$C_{15-25}$alkyl. In some embodiments, Rub is —$(CH_2)_4$—NH—C(O)—$C_{15-20}$alkyl. In some embodiments, Rub is —$(CH_2)_4$—NH—C(O)—$C_{17}$alkyl.

In certain embodiments, the TLR7/8 agonist is a compound of any of the following structures or pharmaceutically acceptable salts thereof:

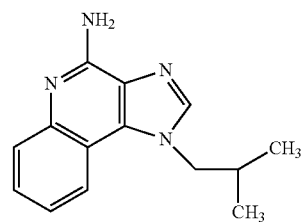

(Imiquimod)

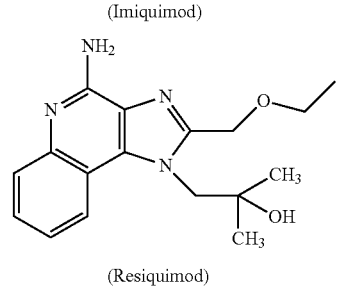

(Resiquimod)

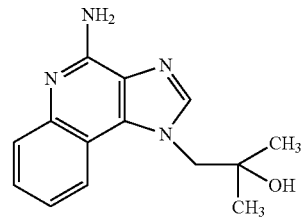

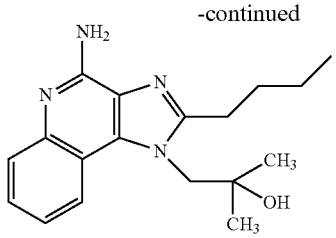

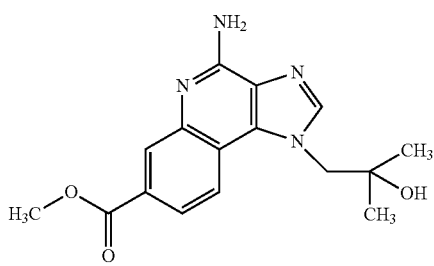

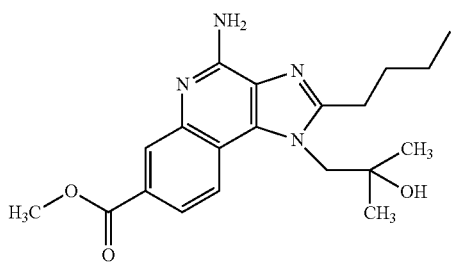

In certain embodiments, the TLR7/8 agonist is a compound of the following structure or pharmaceutically acceptable salts thereof:

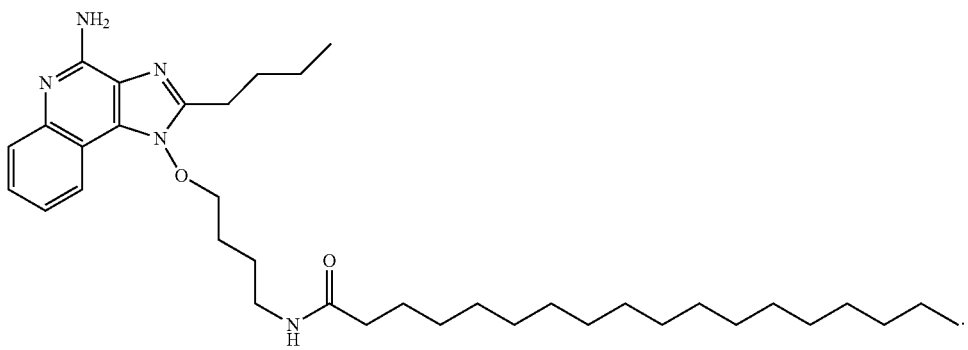

In certain exemplary embodiments, a TLR7/8 agonist used in the compositions herein comprises a N-(4-{[4-amino-2-butyl-1H-imidazo[4,5-c]quinolin-1-yl]oxy}butyl) octadecanamide), 3M-052 as described in U.S. Pat. No. 9,242,980.

TLR4 Agonists

Provided herein are TLR4 agonists that can be used in the compositions described herein. In certain embodiments, a TLR4 agonist used in the compositions herein comprises a glucopyranosyl lipid adjuvant (GLA), such as those described in U.S. Patent Publication Nos. US2007/021017, US2009/045033, US2010/037466, and US 2010/0310602, the contents of which are incorporated herein by reference in their entireties.

For example, in certain embodiments, the TLR4 agonist is a synthetic GLA adjuvant having the following structure of Formula (V):

(V)

[Structure of Formula (V)]

or a pharmaceutically acceptable salt thereof, wherein:
$L_1$, $L_2$, $L_3$, $L_4$, $L_5$ and $L_6$ are the same or different and independently —O—, —NH— or —(CH$_2$)—;
$L_7$, $L_8$, $L_9$, and $L_{10}$ are the same or different and independently absent or —C(=O)—;
$Y_1$ is an acid functional group;
$Y_2$ and $Y_3$ are the same or different and independently —OH, —SH, or an acid functional group;
$Y_4$ is —OH or —SH;
$R_1$, $R_3$, $R_5$ and $R_6$ are the same or different and independently $C_{8-13}$ alkyl; and
$R_2$ and $R_4$ are the same or different and independently $C_{6-11}$ alkyl.

In some embodiments of the synthetic GLA structure, $R^1$, $R^3$, $R^5$ and $R^6$ are $C_{10}$ alkyl; and $R^2$ and $R^4$ are $C_8$ alkyl. In certain embodiments, $R^1$, $R^3$, $R^5$ and $R^6$ are $C_{11}$ alkyl; and $R^2$ and $R^4$ are $C_9$ alkyl.

For example, in certain embodiments, the TLR4 agonist is a synthetic GLA adjuvant having the following structure of Formula (VI):

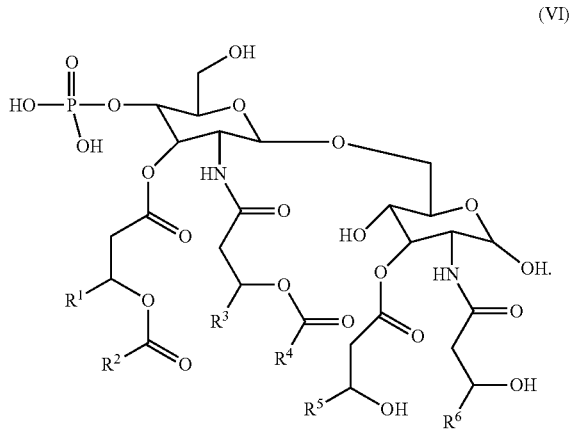

(VI)

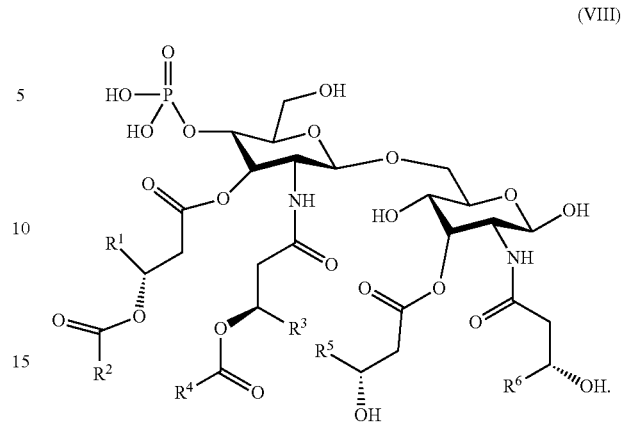

(VIII)

In a specific embodiment, $R^1$, $R^3$, $R^5$ and $R^6$ are $C_{11}$-$C_{20}$ alkyl; and $R^2$ and $R^4$ are $C_{12}$-$C_{20}$ alkyl.

In another specific embodiment, the GLA has the formula set forth above wherein $R^1$, $R^3$, $R^5$ and $R^6$ are $C_{11}$ alkyl; and $R^2$ and $R^4$ are $C_{13}$ alkyl.

In another specific embodiment, the GLA has the formula set forth above wherein $R^1$, $R^3$, $R^5$ and $R^6$ are $C_{10}$ alkyl; and $R^2$ and $R^4$ are $C_8$ alkyl.

In another specific embodiment, the GLA has the formula set forth above wherein $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the TLR4 agonist is a synthetic GLA adjuvant having the following structure of Formula (VII):

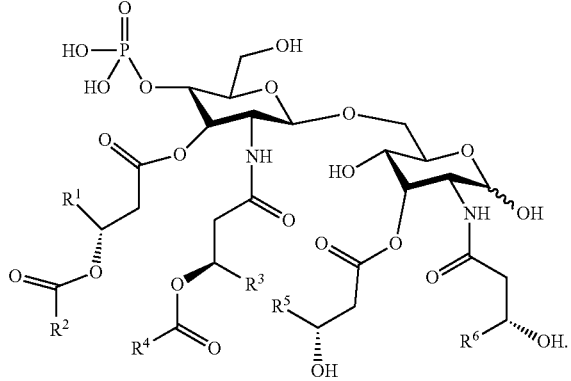

(VII)

In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the TLR4 agonist is a synthetic GLA adjuvant having the following structure of Formula (VIII):

In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the TLR4 agonist is a synthetic GLA adjuvant having the following structure of Formula (IX):

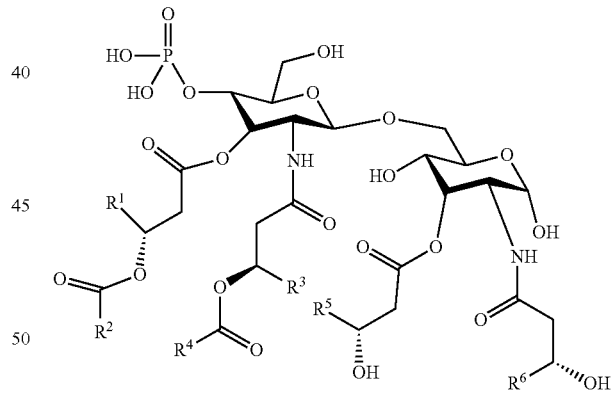

(IX)

In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the TLR4 agonist is a synthetic GLA adjuvant having the following structure:

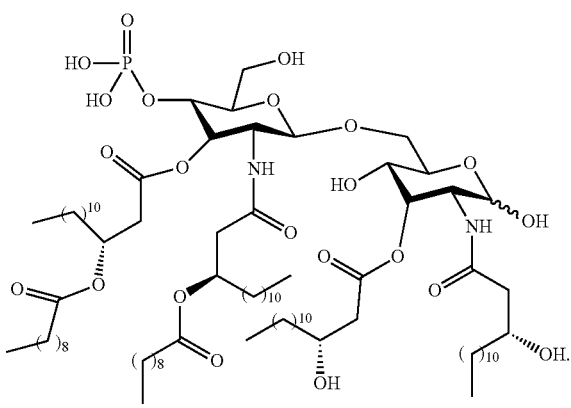

In certain embodiments, the TLR4 agonist is a synthetic GLA adjuvant having the following structure:

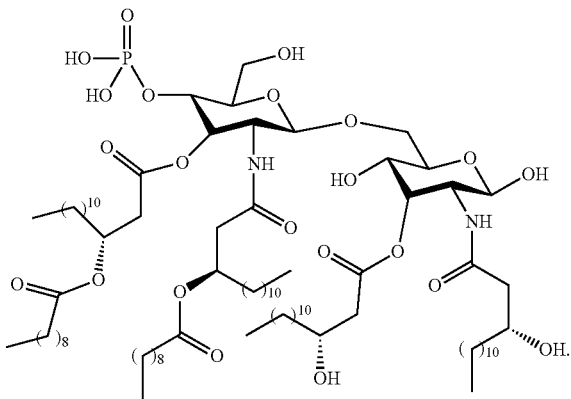

In certain embodiments, the TLR4 agonist is a synthetic GLA adjuvant having the following structure:

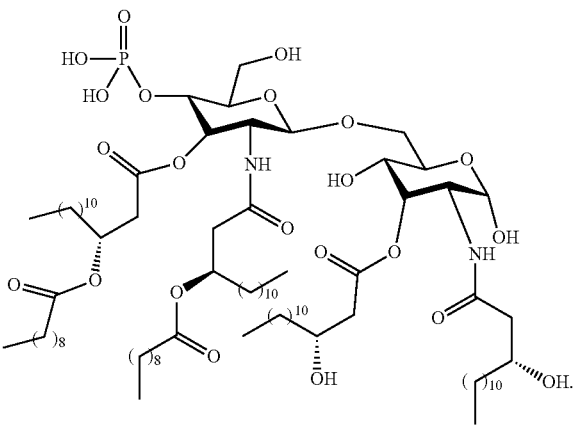

In another embodiment, an attenuated lipid A derivative (ALD) is incorporated into the compositions described herein. ALDs are lipid A-like molecules that have been altered or constructed so that the molecule displays lesser or different of the adverse effects of lipid A. These adverse effects include pyrogenicity, local Shwarzman reactivity and toxicity as evaluated in the chick embryo 50% lethal dose assay (CELD50). ALDs useful according to the present disclosure include monophosphoryl lipid A (MPL) and 3-deacylated monophosphoryl lipid A (3D-MPL). MPL and 3D-MPL are known and need not be described in detail herein. See, for example, U.S. Pat. No. 4,436,727 which discloses monophosphoryl lipid A and its manufacture. U.S. Pat. No. 4,912,094 and reexamination certificate B1 U.S. Pat. No. 4,912,094 embodies 3-deacylated monophosphoryl lipid A and a method for its manufacture. Also, see for example, GB 2220211 and WO 92/116556. 3 De-O-acylated monophosphoryl lipid A is known from GB 2220211 (Ribi). Chemically it is a mixture of 3 De-O-acylated monophosphoryl lipid A with 4, 5 or 6 acylated chains and is manufactured by Ribi Immunochem Montana. A certain form of 3 De-O-acylated monophosphoryl lipid A is disclosed in International Patent Application No. WO 92/116556. Disclosures of each of these patents with respect to MPL and 3D-MPL are incorporated herein by reference.

In the TLR4 agonist compounds above, the overall charge can be determined according to the functional groups in the molecule. For example, a phosphate group can be negatively charged or neutral, depending on the ionization state of the phosphate group.

Exemplary TLR Agonist Embodiments

In some embodiments, the TLR agonist associates with the lipid bilayer of the PEGylated liposome.

In some embodiments, the TLR agonist is enveloped into the PEGylated liposome.

In some embodiments, the TLR agonist is one that would disrupt the structure of a non-PEGylated liposome.

In some embodiments, the TLR agonist comprises a hydrophobic tail. In some embodiments, the hydrophobic tail of the TLR agonist associates with the lipid bilayer of the PEGylated liposome.

In some embodiments, the TLR agonist comprises TLR4, SLA, GLA, MPL, 3D-MPL, R848, R837, or combinations thereof.

In some embodiments, the TLR agonist comprises a TLR4 agonist.

In some embodiments, the TLR agonist comprises a TLR7/8 agonist.

In some embodiments, the TLR agonist comprises a TLR7 agonist.

In some embodiments, the TLR agonist comprises a TLR8 agonist.

In some embodiments, the TLR agonist comprises an imidazoquinoline.

In some embodiments, the TLR agonist comprises 3M-052.

In some embodiments, the TLR agonist comprises a combination of a TLR4 agonist and a TLR 7/8 agonist. In some embodiments, the PEGylated liposome comprises 3M-052 and GLA.

E. Agents

The PEGylated liposomes provided herein may further comprise one or more agents, wherein the agent can be a polypeptide, a polynucleotide, an antigen, an adjuvant, a diagnostic agent, a therapeutic agent, an organism, a genome, or a virus. In some embodiments, the PEGylated liposome comprises two or more agents.

In some embodiments, the agent is associated with the PEGylated liposome. In some embodiments, the agent is associated with the PEGylated by ligand exchange and/or by an electrostatic (charge-based) interaction.

In certain embodiments, the agent may be between about 0.01 to 1% by weight of the PEGylated liposome.

Polypeptides

In some embodiments the agent is a polypeptide. In some embodiments the polypeptide is a full length protein or a fragment thereof. In some embodiments the polypeptide is a peptide. In some embodiments, the polypeptide is a fusion protein. In some particular embodiments, the fusion protein is capable of eliciting an immune response upon administration to an individual. In some embodiments, the polypeptide is an antigen, as further described below.

Antigens

In one embodiment, the agent comprises an antigen.

In some embodiments the polypeptide antigen is involved in, or derived from, an allergy, cancer, or infectious disease.

In some embodiments the compositions described herein are useful for vaccination purposes, and are provided as vaccine formulations (vaccine compositions).

An antigen may be any target epitope, molecule (including a biomolecule), molecular complex (including molecular complexes that contain biomolecules), subcellular assembly, cell or tissue against which elicitation or enhancement of immunoreactivity in a subject is desired. Frequently, the term antigen will refer to a polypeptide antigen of interest. However, antigen, as used herein, may also refer to a recombinant construct which encodes a polypeptide antigen of interest (e.g., an expression construct). In certain embodiments the antigen may be, or may be derived from, or may be immunologically cross-reactive with, an infectious pathogen and/or an epitope, biomolecule, cell or tissue that is associated with infection, cancer, autoimmune disease, allergy, asthma, or any other condition where stimulation of an antigen-specific immune response would be desirable or beneficial.

Certain embodiments contemplate an antigen that is derived from at least one infectious pathogen such as a bacterium, a virus or a fungus, including an Actinobacterium such as *M. tuberculosis* or *M. leprae* or another *mycobacterium*; a bacterium such as a member of the genus *Salmonella, Neisseria, Borrelia, Chlamydia* or *Bordetella*; a virus such as a herpes simplex virus, a human immunodeficiency virus (HIV), a feline immunodeficiency virus (Hy), cytomegalovirus, Varicella Zoster Virus, hepatitis virus, Epstein Barr Virus (EBV), respiratory syncytial virus, human papilloma virus (HPV) and a cytomegalovirus; HIV such as HIV-1 or HIV-2; a fungus such as *Aspergillus, Blastomyces, Coccidioides* and Pneumocysti or a yeast, including *Candida* species such as *C. albicans, C. glabrata, C. krusei, C. lusitaniae, C. tropicalis* and *C. parapsilosis*; a parasite such as a protozoan, for example, a *Plasmodium* species including *P. falciparum, P. vivax, P. malariae* and *P. ovale*; or another parasite such as one or more of *Acanthamoeba, Entamoeba histolytica, Angiostrongylus, Schistosoma mansonii, Schistosoma haematobium, Schistosoma japonicum, Cryptosporidium, Ancylostoma, Entamoeba histolytica, Entamoeba coli, Entamoeba dispar, Entamoeba hartmanni, Entamoeba polecki, Wuchereria bancrofti, Giardia*, and *Leishmania*. In specific embodiments, the antigen may be from, or related to antigens involved in tuberculosis, influenza, amebiasis, HIV, hepatitis, or Leishmaniasis.

In some embodiments, the antigen is an amebiasis-related antigen. In some embodiments, the antigen is an amebiasis-causing antigen. In some embodiments, the antigen is from an amebiasis causing organism. In some embodiments, the antigen is from *Entamoeba histolytica*. In one embodiment, the antigen comprises LecA. In one embodiment, the antigen is LecA.

In some embodiments, the antigen is an influenza-related antigen. In some embodiments, the antigen is an influenza-causing antigen. In some embodiments, the antigen is from an influenza causing virus. In one embodiment, the antigen comprises H5N1. In one embodiment, the antigen comprises H5N1.

For example, in certain embodiments, antigens are derived from *Borrelia* sp., the antigens may include nucleic acid, pathogen derived antigen or antigenic preparations, recombinantly produced protein or peptides, and chimeric fusion proteins. One such antigen is OspA. The OspA may be a full mature protein in a lipidated form by virtue of its biosynthesis in a host cell (Lipo-OspA) or may alternatively be a non-lipidated derivative. Such non-lipidated derivatives include the non-lipidated NS1-OspA fusion protein which has the first 81 N-terminal amino acids of the non-structural protein (NS1) of the influenza virus, and the complete OspA protein, and another, MDP-OspA is a non-lipidated form of OspA carrying 3 additional N-terminal amino acids.

In certain embodiments the antigen is derived from a virus such as from HIV-1, (such as tat, nef, gp120 or gp160), human herpes viruses, such as gD or derivatives thereof or Immediate Early protein such as ICP27 from HSV1 or HSV2, cytomegalovirus ((esp. Human)(such as gB or derivatives thereof), Rotavirus (including live-attenuated viruses), Epstein Barr virus (such as gp350 or derivatives thereof), Varicella Zoster Virus (such as gpl, II and IE63), or from a hepatitis virus such as hepatitis B virus (for example Hepatitis B Surface antigen or a derivative thereof), hepatitis A virus, hepatitis C virus and hepatitis E virus, or from other viral pathogens, such as paramyxoviruses: Respiratory Syncytial virus (such as F and G proteins or derivatives thereof), parainfluenza virus, measles virus, mumps virus, human papilloma viruses (for example HPV6, 11, 16, 18, etc.), flaviviruses (e.g., Yellow Fever Virus, Dengue Virus, Tick-borne encephalitis virus, Japanese Encephalitis Virus) or Influenza virus (whole live or inactivated virus, split influenza virus, grown in eggs or MDCK cells, or whole flu virosomes (as described by Gluck, *Vaccine,* 1992, 10, 915-920) or purified or recombinant proteins thereof, such as HA, NP, NA, or M proteins, or combinations thereof).

In certain other embodiments, the antigen is derived from one or more bacterial pathogens such as *Neisseria* spp, including N. gonorrhea and *N. meningitidis* (for example capsular polysaccharides and conjugates thereof, transferrin-binding proteins, lactoferrin binding proteins, Pi1C, adhesins); *S. pyogenes* (for example M proteins or fragments thereof, C5A protease, lipoteichoic acids), *S. agalactiae, S. mutans: H. ducreyi; Moraxella* spp, including *M. catarrhalis*, also known as Branhamella *catarrhalis* (for example high and low molecular weight adhesins and invasins); *Bordetella* spp, including *B. pertussis* (for example pertactin, pertussis toxin or derivatives thereof, filamenteous hemagglutinin, adenylate cyclase, fimbriae), *B. parapertussis* and *B. bronchiseptica; Mycobacterium* spp., including *M. tuberculosis* (for example ESAT6, Antigen 85A, —B or —C), *M. bovis, M. leprae, M. avium, M. paratuberculosis, M. smegmatis; Legionella* spp, including *L. pneumophila; Escherichia* spp, including enterotoxic *E. coli* (for example colonization factors, heat-labile toxin or derivatives thereof, heat-stable toxin or derivatives thereof), enterohemorragic *E. coli*, enteropathogenic *E. coli* (for example shiga toxin-like toxin or derivatives thereof); *Vibrio* spp, including *V. cholera* (for example cholera toxin or derivatives thereof); *Shigella* spp, including *S. sonnei, S. dysenteriae*, S. flexnerii; *Yersinia* spp, including *Y. enterocolitica* (for example a Yop protein), *Y. pestis, Y. pseudotuberculosis; Campylobacter* spp, including *C. jejuni* (for example toxins, adhesins and invasins) and *C. coli; Salmonella* spp, including *S. typhi, S.*

*paratyphi, S. choleraesuis, S. enteritidis; Listeria* spp., including *L. monocytogenes; Helicobacter* spp, including *H. pylori* (for example urease, catalase, vacuolating toxin); *Pseudomonas* spp, including *P. aeruginosa; Staphylococcus* spp., including *S. aureus, S. epidermidis; Enterococcus* spp., including *E. faecalis, E. faecium; Clostridium* spp., including *C. tetani* (for example tetanus toxin and derivative thereof), *C. botulinum* (for example botulinum toxin and derivative thereof), *C. difficile* (for example *clostridium* toxins A or B and derivatives thereof); *Bacillus* spp., including *B. anthracis* (for example botulinum toxin and derivatives thereof); *Corynebacterium* spp., including C. diphtherias (for example diphtheria toxin and derivatives thereof); *Borrelia* spp., including *B. burgdorferi* (for example OspA, OspC, DbpA, DbpB), *B. garinii* (for example OspA, OspC, DbpA, DbpB), *B. afzelii* (for example OspA, OspC, DbpA, DbpB), *B. andersonii* (for example OspA, OspC, DbpA, DbpB), *B. hermsii; Ehrlichia* spp., including E. equi and the agent of the Human Granulocytic Ehrlichiosis; *Rickettsia* spp, including *R. rickettsii; Chlamydia* spp. including *C. trachomatis* (for example MOMP, heparin-binding proteins), *C. pneumoniae* (for example MOMP, heparin-binding proteins), *C. psittaci*; Leptospira spp., including L. interrogans; *Treponema* spp., including *T. pallidum* (for example the rare outer membrane proteins), *T. denticola, T. hyodysenteriae*; or other bacterial pathogens.

In certain other embodiments, the antigen is derived from one or more parasites (See, e.g., John, D. T. and Petri, W. A., *Markell and Voge's Medical Parasitology-9th Ed.,* 2006, WB Saunders, Philadelphia; Bowman, D. D., *Georgis' Parasitology for Veterinarians-8th Ed.,* 2002, WB Saunders, Philadelphia) such as *Plasmodium* spp., including *P. falciparum; Toxoplasma* spp., including *T. gondii* (for example SAG2, SAG3, Tg34); *Entamoeba* spp., including *E. histolytica; Babesia* spp., including *B. microti; Trypanosoma* spp., including *T. cruzi; Giardia* spp., including *G. lamblia; Leshmania* spp., including *L. major; Pneumocystis* spp., including *P. carinii; Trichomonas* spp., including *T. vaginalis*; or from a helminth capable of infecting a mammal, such as: (i) nematode infections (including, but not limited to, *Enterobius vermicularis, Ascaris lumbricoides, Trichuris trichiura, Necator americanus, Ancylostoma duodenale, Wuchereria bancrofti, Brugia malayi, Onchocerca volvulus, Dracunculus medinensis, Trichinella spiralis,* and *Strongyloides stercoralis*); (ii) trematode infections (including, but not limited to, *Schistosoma mansoni, Schistosoma haematobium, Schistosoma japonicum, Schistosoma mekongi, Opisthorchis sinensis, Paragonimus* sp, *Fasciola hepatica, Fasciola magna, Fasciola gigantica*); and (iii) cestode infections (including, but not limited to, *Taenia saginata* and *Taenia solium*). In certain embodiments, the antigen is derived from Schisostoma spp., *Schistosoma* mansonii, *Schistosoma haematobium,* and/or *Schistosoma japonicum,* or derived from yeast such as *Candida* spp., including *C. albicans; Cryptococcus* spp., including *C. neoformans.*

Other specific antigens are derived from *M. tuberculosis*, for example Th Ra12, Tb H9, Tb Ra35, Tb38-1, Erd 14, DPV, MTI, MSL, mTTC2 and hTCC1 (WO 99/51748). Proteins for *M. tuberculosis* also include fusion proteins and variants thereof where at least two, three, or four or more, polypeptides of *M. tuberculosis* are fused into a larger protein. Certain fusions include Ra12-TbH9-Ra35, Erd14-DPV-MTI, DPV-MTI-MSL, Erd14DPV-MTI-MSL-mTCC2, Erd14-DPV-MTI-MSL, DPV-MTI-MSL-mTCC2, TbH9-DPV-MTI (WO 99151748). Other antigens that may be used include antigens, combination of antigens, and fusion proteins described in US 2010/0129391 and WO 2008/124647. In one exemplary embodiment, the fusion protein is ID93. In one exemplary embodiment, the fusion protein is ID91.

Other specific antigens are derived from *Chlamydia*, and include for example the High Molecular Weight Protein (HWMP) (WO 99/17741), ORF3 (EP 366 412), and putative membrane proteins (Pmps). Other *Chlamydia* antigens can be selected from the group described in WO 99128475. Certain antigens may be derived from *Streptococcus* spp, including *S. pneumoniae* (for example capsular polysaccharides and conjugates thereof, PsaA, PspA, streptolysin, choline-binding proteins) and the protein antigen Pneumolysin (Biochem Biophys Acta, 1989, 67, 1007; Rubins et al., Microbial Pathogenesis, 25, 337-342), and mutant detoxified derivatives thereof (WO 90/06951; WO 99/03884). Other bacterial vaccines comprise antigens derived from *Haemophilus* spp., including *H. influenzae* type B (for example PRP and conjugates thereof), non typeable *H. influenzae,* for example OMP26, high molecular weight adhesins, P5, P6, protein D and lipoprotein D, and fimbrin and fimbrin derived peptides (U.S. Pat. No. 5,843,464) or multiple copy varients or fusion proteins thereof.

Other specific antigens fare derived from Hepatitis B. Derivatives of Hepatitis B Surface antigen are well known in the art and include, inter alia, those PreS1, Pars2 S antigens set forth described in European Patent applications EP-A414 374; EP-A-0304 578, and EP 198474. In one aspect antigen is HIV-1 gp120, especially when expressed in CHO cells. In a further embodiment, the antigen is gD2t.

In other embodiments, the antigen is derived from the Human Papilloma Virus (HPV) considered to be responsible for genital warts (HPV 6 or HPV 11 and others), and the HPV viruses responsible for cervical cancer (HPV16, HPV18 and others). Particular antigens include L1 particles or capsomers, and fusion proteins comprising one or more antigens selected from the HPV 6 and HPV 11 proteins E6, E7, L1, and L2. Certain forms of fusion protein include L2E7 as disclosed in WO 96/26277, and proteinD(1/3)-E7 disclosed in GB 9717953.5 (PCT/EP98/05285). Additional possible antigens include HPV 16 or 18 antigens. For example, L1 or L2 antigen monomers, or L1 or L2 antigens presented together as a virus like particle (VLP) or the L1 alone protein presented alone in a VLP or caposmer structure. Such antigens, virus like particles and capsomer are per se known. See for example WO94/00152, WO94/20137, WO94/05792, and WO93/02184.

In other embodiments, the antigen is a fusion protein. Fusion proteins may be included alone or as fusion proteins such as E7, E2 or F5 for example; particular embodiments include a VLP comprising L1E7 fusion proteins (WO 96/11272). Particular HPV 16 antigens comprise the early proteins E6 or F7 in fusion with a protein D carrier to form Protein D-E6 or E7 fusions from HPV 16, or combinations thereof; or combinations of E6 or E7 with L2 (WO 96/26277). Alternatively the HPV 16 or 18 early proteins E6 and E7, may be presented in a single molecule, for example a Protein D-E6/E7 fusion. Compositions may optionally contain either or both E6 and E7 proteins front HPV 18, for example in the form of a Protein D-E6 or Protein D-E7 fusion protein or Protein D E6/E7 fusion protein. Compositions may additionally comprise antigens from other HPV strains, for example from strains HPV 31 or 33.

Antigens may also be derived from parasites that cause Malaria. For example, antigens from Plasmodia *falciparum* include RTS, S and TRAP. RTS is a hybrid protein comprising substantially all the C-terminal portion of the circumsporozoite (CS) protein of *P. falaparum* linked via four amino acids of the preS2 portion of Hepatitis B surface antigen to the surface (S) antigen of hepatitis B virus. Its full structure is disclosed in the International Patent Application No. PCT/EP92/02591, published as WO 93/10152 claiming priority from UK patent application No. 9124390.7. When expressed in yeast RTS is produced as a lipoprotein particle, and when it is co-expressed with the S antigen from HBV it produces a mixed particle known as RTS,S.

TRAP antigens are described in the International Patent Application No. PCT/GB89/00895 published as WO 90/01496. An embodiment of the present invention is a Malaria vaccine wherein the antigenic preparation comprises a combination of the RTS,S and TRAP antigens. Other plasmodia antigens that are likely candidates to be components of a multistage Malaria vaccine are *P. faciparum* MSP1, AMA1, MSP3, EBA, GLURP, RAP1, RAP2, Sequestrin, PfEMP1, Pf332, LSA1, LSA3, STARP, SALSA, PfEXP1, Pfs25, Pfs28, PFS27125, Pfs16, Pfs48/45, Pfs230 and their analogues in *Plasmodium* spp.

In one embodiment, the antigen is derived from a cancer cell, as may be useful for the immunotherapeutic treatment of cancers. For example, the antigen may be a tumor rejection antigen such as those for prostate, breast, colorectal, lung, pancreatic, renal or melanoma cancers. Exemplary cancer or cancer cell-derived antigens include MAGE 1, 3 and MAGE 4 or other MAGE antigens such as those disclosed in WO99/40188, PRAIVIE, BAGE, Lage (also known as NY Eos 1) SAGE and HAGE (WO 99/53061) or GAGE (Robbins and Kawakami, 1996 *Current Opinions in Immunology* 8, pps 628-636; Van den Eynde et al., *International Journal of Clinical & Laboratory Research* (1997 & 1998); Correale et al. (1997), *Journal of the National Cancer Institute* 89, p. 293. These non-limiting examples of cancer antigens are expressed in a wide range of tumor types such as melanoma, lung carcinoma, sarcoma and bladder carcinoma. See, e.g., U.S. Pat. No. 6,544,518.

Other tumor-specific antigens are include, but are not restricted to, tumor-specific or tumor-associated gangliosides such as GM2, and GM3 or conjugates thereof to carrier proteins; or a self peptide hormone such as whole length Gonadotrophin hormone releasing hormone (GnRH, WO 95/20600), a short 10 amino acid long peptide, useful in the treatment of many cancers. In another embodiment prostate antigens are used, such as Prostate specific antigen (PSA), PAP, PSCA (e.g., *Proc. Nat. Acad. Sci. USA* 95(4) 1735-1740 1998), PSMA or, in one embodiment an antigen known as Prostase. (e.g., Nelson, et al., *Proc. Natl. Acad. Sci. USA* (1999) 96: 3114-3119; Ferguson, et al. *Proc. Natl. Acad. Sci. USA* 1999. 96, 3114-3119; WO 98/12302; U.S. Pat. No. 5,955,306; WO 98/20117; U.S. Pat. Nos. 5,840,871 and 5,786,148; WO 00/04149. Other prostate specific antigens are known from WO 98/137418, and WO/004149. Another is STEAP (PNAS 96 14523 14528 7-12 1999).

Other tumor associated antigens useful in the context of the present invention include: Plu-1 (*J Biol. Chem* 274 (22) 15633-15645, 1999), HASH-1, HasH-2, Cripto (Salomon et al Bioessays 199, 21:61-70, U.S. Pat. No. 5,654,140) and Criptin (U.S. Pat. No. 5,981,215). Additionally, antigens particularly relevant for vaccines in the therapy of cancer also comprise tyrosinase and survivin.

In other embodiments, the agents used in the compositions of the invention include antigens associated with respiratory diseases, such as those caused or exacerbated by bacterial infection (e.g. pneumococcal), for the prophylaxis and therapy of conditions such as chronic obstructive pulmonary disease (COPD). COPD is defined physiologically by the presence of irreversible or partially reversible airway obstruction in patients with chronic bronchitis and/or emphysema (Am J Respir Crit Care Med. 1995 November; 152(5 Pt 2):577-121). Exacerbations of COPD are often caused by bacterial (e.g. pneumococcal) infection (Clin Microbiol Rev. 2001 April; 14(2):336-63).

Polynucleotides

In some embodiments the agent is a polynucleotide. A polynucleotide includes, but is not limited to a DNA, an RNA, an aptamer, and an oligonucleotide. In some embodiments the polynucleotide is DNA. In some embodiments the polynucleotide is RNA. In some embodiments, the DNA or RNA is single stranded or double stranded. In some embodiments the polynucleotide is a non-coding RNA. In some embodiments the polynucleotide is a coding RNA. In some embodiments the RNA is selected from the group consisting of replicon RNA, mRNA, tRNA, siRNA, shRNA, and microRNA.

In some embodiments, the polynucleotide encodes a polypeptide. In some embodiments, the polynucleotide encodes a polypeptide that is an antigen or comprises an antigen. In some embodiments, the polypeptide encoded by the polynucleotide is a fusion protein. In some embodiments, the polypeptide encoded by the polynucleotide is LecA. In some embodiments, the polypeptide encoded by the polynucleotide is H5N1. In some embodiments, the polypeptide encoded by the polynucleotide is ID93.

In some embodiments, the polynucleotide is a replicon. In some embodiments, the replicon is a plasmid, cosmid, bacmid, phage or virus, that is capable of replication largely under its own control. In some embodiments, the replicon is RNA or DNA. In some embodiments, the replicon is single or double stranded. In some embodiments, the replicon is derived from an RNA virus.

Adjuvants

In some embodiments, the PEGylated liposomes provided herein further comprise an adjuvant or may be co-administered with a co-adjuvant. In some embodiments, the adjuvant is selected from the group consisting of a retinoic acid (RA), AS-2, monophosphoryl lipid A, 3-de-O-acylated monophosphoryl lipid A, IFA, QS21, CWS, TOM, AGPs, CpG-containing oligonucleotides, Toll-like receptor (TLR) agonists, Leif, saponins, saponin mimetics, biological and synthetic lipid A, imiquimod, gardiquimod, resiquimod, polyI:C, flagellin, GLA, SLA, Stingin, and combinations thereof.

Organisms

In some embodiments, the PEGylated liposomes provided herein comprise an organism. For example, the *Entamoeba histolytica*, an influenza-causing virus, or the bacterium *Mycobacterium tuberculosis* which causes tuberculosis (TB). Currently, vaccination with live bacteria is the most efficient method for inducing protective immunity against tuberculosis. The most common *Mycobacterium* employed for this purpose is *Bacillus* Calmette-Guerin (BCG), an avirulent strain of *Mycobacterium bovis*. Thus in some embodiments the composition comprises a PEGylated liposome and a *Mycobacterium*.

In some embodiments the agent is a virus or a viral genome. Thus in these embodiments, the PEGylated liposomes comprise an virus or viral genome.

F. Exemplary PEGylated Liposomes

In certain embodiments, the lipid molar ratio of the non-PEGylated neutral lipid:cholesterol:PEGylated lipid in the PEGylated liposome of the invention is about 9.8:5.7:0.8.

In certain embodiments, the lipid molar ratio of the non-PEGylated neutral lipid:cholesterol:PEGylated lipid in the PEGylated liposome of the invention is about 18:5.5:3.

In certain embodiments, the lipid molar ratio of the non-PEGylated neutral lipid DPPC:cholesterol:PEGylated lipid DPPE-PEG750 in the PEGylated liposome of the invention is about 9.8:5.7:0.8.

In certain embodiments, the lipid molar ratio of the non-PEGylated neutral lipid DPPC:cholesterol:PEGylated lipid DPPE-PEG2000 in the PEGylated liposome of the invention is about 9.8:5.7:0.8.

In certain embodiments, the lipid molar ratio of the non-PEGylated neutral lipid DPPC:cholesterol:PEGylated lipid DPPE-PEG750 in the PEGylated liposome of the invention is about 18:5.5:3.

In certain embodiments, the PEGylated liposome comprises GLA, a cholesterol, a non-PEGylated neutral lipid, and a PEGylated lipid, wherein the PEG component is PEG2000.

In certain embodiments, the PEGylated liposome comprises GLA, a cholesterol, a non-PEGylated neutral lipid, and a PEGylated lipid, wherein the PEG component is PEG750.

In certain embodiments, the PEGylated liposome comprises a LecA antigen, GLA, a cholesterol, a non-PEGylated neutral lipid, and a PEGylated lipid, wherein the PEG component is PEG2000.

In certain embodiments, the PEGylated liposome a LecA antigen, GLA, a cholesterol, a non-PEGylated neutral lipid, and a PEGylated lipid, wherein the PEG component is PEG750.

In certain embodiments, the PEGylated liposome comprises a H5N1 antigen, GLA, a cholesterol, a non-PEGylated neutral lipid, and a PEGylated lipid, wherein the PEG component is PEG2000.

In certain embodiments, the PEGylated liposome a H5N1 antigen, GLA, a cholesterol, a non-PEGylated neutral lipid, and a PEGylated lipid, wherein the PEG component is PEG750.

In certain embodiments, the PEGylated liposome comprises an ID93 antigen, GLA, a cholesterol, a non-PEGylated neutral lipid, and a PEGylated lipid, wherein the PEG component is PEG2000.

In certain embodiments, the PEGylated liposome an ID93 antigen, GLA, a cholesterol, a non-PEGylated neutral lipid, and a PEGylated lipid, wherein the PEG component is PEG750.

In certain embodiments, the PEGylated liposome comprises an ID91 antigen, GLA, a cholesterol, a non-PEGylated neutral lipid, and a PEGylated lipid, wherein the PEG component is PEG2000.

In certain embodiments, the PEGylated liposome an ID91 antigen, GLA, a cholesterol, a non-PEGylated neutral lipid, and a PEGylated lipid, wherein the PEG component is PEG750.

In certain embodiments, the PEGylated liposome comprises 3M-052, a cholesterol, a non-PEGylated neutral lipid, and a PEGylated lipid, wherein the PEG component is PEG2000.

In certain embodiments, the PEGylated liposome comprises 3M-052, a cholesterol, a non-PEGylated neutral lipid, and a PEGylated lipid, wherein the PEG component is PEG 750.

In certain embodiments, the PEGylated liposome comprises 3M-052 and GLA, a cholesterol, a non-PEGylated neutral lipid, and a PEGylated lipid, wherein the PEG component is PEG2000.

In certain embodiments, the PEGylated liposome comprises 3M-052 and GLA, a cholesterol, a non-PEGylated neutral lipid, and a PEGylated lipid, wherein the PEG component is PEG750.

In certain embodiments, the PEGylated liposome comprises a LecA antigen, 3M-052 and GLA, a cholesterol, a non-PEGylated neutral lipid, and a PEGylated lipid, wherein the PEG component is PEG2000.

In certain embodiments, the PEGylated liposome comprises a LecA antigen, 3M-052 and GLA, a cholesterol, a non-PEGylated neutral lipid, and a PEGylated lipid, wherein the PEG component is PEG750.

In certain embodiments, the PEGylated liposome comprises a H5N1 antigen, 3M-052 and GLA, a cholesterol, a non-PEGylated neutral lipid, and a PEGylated lipid, wherein the PEG component is PEG2000.

In certain embodiments, the PEGylated liposome comprises a H5N1 antigen, 3M-052 and GLA, a cholesterol, a non-PEGylated neutral lipid, and a PEGylated lipid, wherein the PEG component is PEG750.

In certain embodiments, the PEGylated liposome comprises a tuberculosis-related antigen, an HIV-related antigen, a cancer-related antigen, an amebiasis-related antigen, an influenza-related antigen, or a hepatitis-related antigen, a TLR agonist, a cholesterol, a non-PEGylated neutral lipid, and a PEGylated lipid, wherein the PEG component is PEG2000.

In certain embodiments, the PEGylated liposome comprises a tuberculosis-related antigen, an HIV-related antigen, a cancer-related antigen, an amebiasis-related antigen, an influenza-related antigen, or a hepatitis-related antigen, a TLR agonist, a cholesterol, a non-PEGylated neutral lipid, and a PEGylated lipid, wherein the PEG component is PEG750.

In certain embodiments, the PEGylated liposome comprises a tuberculosis-related antigen, an HIV-related antigen, a cancer-related antigen, an amebiasis-related antigen, an influenza-related antigen, or a hepatitis-related antigen, GLA, a cholesterol, a non-PEGylated neutral lipid, and a PEGylated lipid, wherein the PEG component is PEG2000.

In certain embodiments, the PEGylated liposome comprises a tuberculosis-related antigen, an HIV-related antigen, a cancer-related antigen, an amebiasis-related antigen, an influenza-related antigen, or a hepatitis-related antigen, GLA, a cholesterol, a non-PEGylated neutral lipid, and a PEGylated lipid, wherein the PEG component is PEG750.

In certain embodiments, the PEGylated liposome comprises a tuberculosis-related antigen, an HIV-related antigen, a cancer-related antigen, an amebiasis-related antigen, an influenza-related antigen, or a hepatitis-related antigen, 3M-052, a cholesterol, a non-PEGylated neutral lipid, and a PEGylated lipid, wherein the PEG component is PEG2000.

In certain embodiments, the PEGylated liposome comprises a tuberculosis-related antigen, an HIV-related antigen, a cancer-related antigen, an amebiasis-related antigen, an influenza-related antigen, or a hepatitis-related antigen, 3M-052, a cholesterol, a non-PEGylated neutral lipid, and a PEGylated lipid, wherein the PEG component is PEG750.

III. Physiochemical Characteristics of the PEGylated Liposomes

A. Size

As provided herein, the size of the PEGylated liposome ranges from about 1 nm to 450 nm, and can be considered to be a PEGylated nanoliposome. Such nanoliposomes are amenable to manufacturing and are filter sterilizable. Furthermore, in vivo, delivery of such nanoliposomes comprising an agent (e.g. an antigen and/or an adjuvant) typically do not display, or reduce the occurrence of a depot effect. Moreover in vivo delivery of such nanoliposomes comprising an agent (e.g. an antigen and/or an adjuvant) allow for delivery to draining lymph nodes, and allow for presentation to antigen presenting cells and allow for generation of an effective Th1-based immune response.

In some embodiments, the size of the PEGylated liposome can be assessed by known techniques in the art, including but not limited to, x-ray and laser diffraction, dynamic light scattering (DLS), CryoEM, or Malvern Zetasize. In some embodiments, the size of the PEGylated liposome refers to the Z-average diameter.

In some embodiments the size of the PEGylated liposome ranges from about 50 nm to 75 nm. In some embodiments the size of the PEGylated liposome ranges from about 50 nm to 100 nm. In some embodiments the size of the PEGylated liposome ranges from about 50 nm to 150 nm. In some embodiments the size of the PEGylated liposome ranges from about 50 nm to 200 nm. In some embodiments the size of the PEGylated liposome ranges from about 50 nm to 300 nm. In some embodiments the size of the PEGylated liposome ranges from about 20 nm to 100 nm. In some embodiments the size of the PEGylated liposome ranges from about 20 nm to 50 nm. In some embodiments the size of the PEGylated liposome ranges from about 10 nm to 200 nm. In some embodiments the size of the PEGylated liposome ranges from about 10 nm to 100 nm. In some embodiments the size of the PEGylated liposome ranges from about 10 nm to 50 nm. In some embodiments the size of the PEGylated liposome is about 1 nm, is about 5 nm, is about 10 nm, is about 15 nm, is about 20 nm, is about 25 nm, is about 30 nm, is about 35 nm, is about 40 nm, is about 45 nm, is about 50 nm, is about 55 nm, is about 60 nm, is about 65 nm, is about 70 nm, is about 75 nm, is about 80 nm, is about 85 nm, is about 90 nm, is about 95 nm, is about 100 nm, is about 105 nm, is about 110 nm, is about 115 nm, is about 120 nm, is about 125 nm, is about 130 nm, is about 135 nm, is about 140 nm, is about 145 nm, is about 150 nm, is about 155 nm, is about 160 nm, is about 165 nm, is about 170 nm, is about 175 nm, is about 180 nm, is about 185 nm, is about 190 nm, is about 195 nm, or is about 200 nm. In some embodiments, the size of the PEGylated liposome is no greater than about 1 nm, no greater than about 5 nm, no greater than about 10 nm, no greater than about 15 nm, no greater than about 20 nm, no greater than about 25 nm, no greater than about 30 nm, no greater than about 35 nm, no greater than about 40 nm, no greater than about 45 nm, no greater than about 50 nm, no greater than about 55 nm, no greater than about 60 nm, no greater than about 65 nm, no greater than about 70 nm, no greater than about 75 nm, no greater than about 80 nm, no greater than about 85 nm, no greater than about 90 nm, no greater than about 95 nm, no greater than about 100 nm, no greater than about 105 nm, no greater than about 110 nm, no greater than about 115 nm, no greater than about 120 nm, no greater than about 125 nm, no greater than about 130 nm, no greater than about 135 nm, no greater than about 140 nm, no greater than about 145 nm, no greater than about 150 nm, no greater than about 155 nm, no greater than about 160 nm, no greater than about 165 nm, no greater than about 170 nm, no greater than about 175 nm, no greater than about 180 nm, no greater than about 185 nm, no greater than about 190 nm, no greater than about 195 nm, or no greater than about 199 nm.

As provided herein, in preferred embodiments, the PEGylated liposome is capable of being filtered through at least a 0.45 micron filter. In some embodiments, the PEGylated liposome is capable of being filtered through a filter smaller than 0.45 microns. In an exemplary embodiment, the PEGylated liposome is capable of being filtered through a 0.20 or 0.22 micron filter.

B. Stability

The PEGylated liposomes provided herein are stable, allowing for ease of use, manufacturability, transportability, and storage. The inventors have discovered that PEGylating a liposome contributes to the stability of the liposome. The physiochemical characteristics of the PEGylated liposome, including, but not limited to its size, is maintained over time, at various temperatures, and under various conditions.

In some embodiments, the PEGylated liposome exhibits reduced aggregation, or no aggregation, when compared to liposome in the absence of a PEGylated lipid. In some embodiments, the PEGylated liposome or composition comprised of PEGylated liposomes does not aggregate, displays little to no aggregation, displays reduced aggregation, or does not demonstrate an overall increase in average size over time compared to its initial size.

The stability of the PEGylated liposome can be measured by techniques familiar to those of skill in the art. In some embodiments, the stability is observed visually. Visual inspection can include inspection for particulates, flocculence, or aggregates. In some embodiments, the stability is determined by the size of the PEGylated liposome, and optionally expressed as change in size over time, or at various temperatures, or under certain conditions. In some embodiments, the stability is determined by assessing the % aggregation of PEGylated liposomes in the composition. In some embodiments, the stability is assessed by the ability of the PEGylated liposome to pass through a filter of a particular size, for example through a 0.20, 0.22 or 0.45 micron filter. In some embodiments, stability is determined by pH. In some embodiments, stability is determined by measurement of the polydispersity index (PdI), for example with the use of the dynamic light scattering (DLS) technique.

In some embodiments, the Z-average diameter of the PEGylated liposome increases less than 50%, less than 40%, less than 30%, less than 25%, less than 20%, less than 15%, less than 12%, less than 10%, less than 7%, less than 5%, less than 3%, less than 1% over the time period assayed.

In some embodiments, the PEGylated liposome is stable at 0-8° C. In some embodiments, the PEGylated liposome is stable at 0° C., 1° C., 2° C., 3° C., 4° C., 5° C., 6° C., 7° C., or 8° C. for at least 1 minute, for at least 5 minutes, for at least 10 minutes, for at least 15 minutes, for at least 20 minutes, for at least 25 minutes, for at least 30 minutes, for at least 35 minutes, for at least 40 minutes, for at least 45 minutes, for at least 50 minutes, for at least 55 minutes, for at least 1 hour, for at least 2 hours, for at least 6 hours, for at least 12 hours, for at least 18 hours, for at least 24 hours, for at least 48 hours, for at least 72 hours, for at least 1 week, for at least 2 weeks, for at least 3 weeks, for at least 1 month, for at least 2 months, for at least 3 months, for at least 4 months, for at least 5 months, for at least 6 months, for at least 7 months, for at least 8 months, for at least 9 months, for at least 10 months, for at least 11 months, for at least 1 year, for at least 2 years, or for at least 5 years. In one exemplary embodiment, the PEGylated liposome is stable for at least 1 month at a temperature of about 2° C. to about 8° C. In another exemplary embodiment, the PEGylated liposome is stable for at least 1 month at a temperature of about 4° C. to about 8° C. In another exemplary embodiment, the PEGylated liposome is stable for at least 6 months at a temperature of about 4° C. to about 8° C. In another exemplary embodiment, the PEGylated liposome is stable for at least 1 year at a temperature of about 4° C. to about 8° C.

In some embodiments, the PEGylated liposome is stable at 8-20° C. In some embodiments, the PEGylated liposome is stable at 8-20° C. for at least 1 minute, for at least 5 minutes, for at least 10 minutes, for at least 15 minutes, for at least 20 minutes, for at least 25 minutes, for at least 30 minutes, for at least 35 minutes, for at least 40 minutes, for at least 45 minutes, for at least 50 minutes, for at least 55 minutes, for at least 1 hour, for at least 2 hours, for at least 6 hours, for at least 12 hours, for at least 18 hours, for at least 24 hours, for at least 48 hours, for at least 72 hours, for at least 1 week, for at least 2 weeks, for at least 3 weeks, for at least 1 month, for at least 2 months, for at least 3 months, for at least 4 months, for at least 5 months, for at least 6 months, for at least 7 months, for at least 8 months, for at least 9 months, for at least 10 months, for at least 11 months, for at least 1 year, for at least 2 years, or for at least 5 years. In one exemplary embodiment, the PEGylated liposome is stable for at least 1 month at a temperature of about 8° C. to about 20° C. In another exemplary embodiment, the PEGylated liposome is stable for at least 1 month at a temperature of about 8° C. to about 20° C. In another exemplary embodiment, the PEGylated liposome is stable for at least 6 months at a temperature of about 8° C. to about 20° C. In another exemplary embodiment, the PEGylated liposome is stable for at least 1 year at a temperature of about 8° C. to about 20° C.

In some embodiments, the PEGylated liposome is stable at 20-30° C. In some embodiments, the PEGylated liposome is stable at 25° C. for at least 1 minute, for at least 5 minutes, for at least 10 minutes, for at least 15 minutes, for at least 20 minutes, for at least 25 minutes, for at least 30 minutes, for at least 35 minutes, for at least 40 minutes, for at least 45 minutes, for at least 50 minutes, for at least 55 minutes, for at least 1 hour, for at least 2 hours, for at least 6 hours, for at least 12 hours, for at least 18 hours, for at least 24 hours, for at least 48 hours, for at least 72 hours, for at least 1 week, for at least 2 weeks, for at least 3 weeks, for at least 1 month, for at least 2 months, for at least 3 months, for at least 4 months, for at least 5 months, for at least 6 months, for at least 7 months, for at least 8 months, for at least 9 months, for at least 10 months, for at least 11 months, for at least 1 year, for at least 2 years, or for at least 5 years. In one exemplary embodiment, the PEGylated liposome is stable for at least 1 month at a temperature of about 25° C. In another exemplary embodiment, the PEGylated liposome is stable for at least 6 months at a temperature of about 25° C. In another exemplary embodiment, the PEGylated liposome is stable for at least 1 year at a temperature of about 25° C.

In some embodiments, the PEGylated liposome is stable at 30-40° C. In some embodiments, the PEGylated liposome is stable at 30° C., 31° C., 32° C., 33° C., 34° C. 35° C., 36° C., 37° C., 38° C., 39° C., or 40° C. for at least 1 minute, for at least 5 minutes, for at least 10 minutes, for at least 15 minutes, for at least 20 minutes, for at least 25 minutes, for at least 30 minutes, for at least 35 minutes, for at least 40 minutes, for at least 45 minutes, for at least 50 minutes, for at least 55 minutes, for at least 1 hour, for at least 2 hours, for at least 6 hours, for at least 12 hours, for at least 18 hours, for at least 24 hours, for at least 48 hours, for at least 72 hours, for at least 1 week, for at least 2 weeks, for at least 3 weeks, for at least 1 month, for at least 2 months, for at least 3 months, for at least 4 months, for at least 5 months, for at least 6 months, for at least 7 months, for at least 8 months, for at least 9 months, for at least 10 months, for at least 11 months, for at least 1 year, for at least 2 years, or for at least 5 years. In one exemplary embodiment, the PEGylated liposome is stable for at least 1 month at a temperature of about 37° C.

In some embodiments, the PEGylated liposome is stable at 40-62° C. In some embodiments, the PEGylated liposome is stable at 40-62° C. for at least 1 minute, for at least 5 minutes, for at least 10 minutes, for at least 15 minutes, for at least 20 minutes, for at least 25 minutes, for at least 30 minutes, for at least 35 minutes, for at least 40 minutes, for at least 45 minutes, for at least 50 minutes, for at least 55 minutes, for at least 1 hour, for at least 2 hours, for at least 6 hours, for at least 12 hours, for at least 18 hours, for at least 24 hours, for at least 48 hours, for at least 72 hours, for at least 1 week, for at least 2 weeks, for at least 3 weeks, for at least 1 month.

In one exemplary embodiment, the PEGylated liposome is stable at 4-8° C. for at least one year. In another exemplary embodiment, the PEGylated liposome is stable at 25° C. for at least one year.

In some embodiments, the PEGylated liposome is stable after 1-5 freeze thaws. In some embodiments, the PEGylated liposome is stable after 1, after 2, after 3, after 4, or after 5 freeze thaws.

In some embodiments the polydispersity index of the PEGylated liposome is maintained at about 0.3 or less. In some embodiments the polydispersity index of the PEGylated liposome is maintained at about 0.25 or less. In some embodiments the polydispersity index of the PEGylated liposome is maintained at about 0.2 or less.

IV. Methods of Making the PEGylated Liposomes

As provided herein, a method of making a PEGylated liposome comprises (a) mixing the non-PEGylated neutral lipid, the PEGylated lipid, and the cholesterol in an organic solvent; (b) evaporating the organic solvent, whereby generating a lipid film; (c) rehydrating the lipid film in a buffer; and (d) applying a high energy input source (e.g. sonication, microfluidization, extrusion) to the rehydrated product of step (c). In some embodiments, the high energy source comprises microfluidization. In some embodiments, the high energy source comprises sonication. In some embodiments, the high energy source comprises extrusion. In some embodiments, the organic solvent is chloroform or a chloroform/methanol/water mixture. In some embodiments, step (a) further comprises mixing a TLR agonist with the other components.

In an exemplary embodiment, DPPC, cholesterol, and DPPE-PEG750 is combined with various amounts of 3M-052 in organic solvent (chloroform or chloroform/methanol/water mixture). The organic solvent is then evaporated. The resulting lipid film is rehydrated in a buffer and sonicated until the formulation is translucent with no large visible particles. Larger batches (100 mL) of PEGylated liposomes can be manufactured as above but with shorter sonication time followed by high shear homogenization.

In some embodiment, the resulting PEGylating liposome admixing with an agent (e.g. an antigen).

V. Compositions Comprising the PEGylated Liposomes

Provided herein are formulations, compositions, and pharmaceutical compositions comprising the PEGylated liposomes described herein.

In some embodiments, the composition comprising PEGylated liposome further comprises a pharmaceutically acceptable carrier, excipient or diluent.

The compositions described herein can be administered to a subject for any vaccination, therapeutic or diagnostic purposes.

Pharmaceutical compositions generally comprise compositions described herein and may further comprise one or more components as provided herein that are selected from an antigen, additional agonists, or a recombinant expression construct, in combination with a pharmaceutically acceptable carrier, excipient or diluent.

In the embodiments provided herein, the pharmaceutical composition is capable of being filtered through a 0.45 micron filter. In some embodiments, the pharmaceutical composition is capable of being filtered through a 0.20 micron filter. In some embodiments, the pharmaceutical composition is capable of being filtered through a 0.22 micron filter.

In one embodiment, the present invention is drawn to a pharmaceutical composition comprising a PEGylated liposome which comprises a TLR7/8 agonist or a TLR4 agonist. Such a composition can be used for "monotherapy" wherein the TLR7/8 agonist or TLR 4 agonist, as described herein, is formulated in a composition and the composition is substantially devoid of other antigens, and is administered to a subject in order to stimulate an immune response, e.g., a non-specific immune response or an antigen-specific immune response, for the purpose of diagnosis, treating or preventing a disease or other condition, such as an infection by an organism.

In other embodiments, the pharmaceutical composition is a vaccine composition that comprises both compositions described herein and an antigen and may further comprise one or more components, as provided herein, in combination with a pharmaceutically acceptable carrier, excipient or diluent. Illustrative carriers are usually nontoxic to recipients at the dosages and concentrations employed.

In the therapeutic embodiments provided herein, a dosage of about 1 µg/kg to about 1 mg/kg of a therapeutic pharmaceutical composition is administered. It will be evident to those skilled in the art that the number and frequency of administration will be dependent upon the response of the subject.

In the vaccine-based embodiments provided herein, about 1 ug-25 ug of the agent (e.g. adjuvant, or antigen) will be administered per administration. It will be evident to those skilled in the art that the number and frequency of administration will be dependent upon the response of the subject.

"Pharmaceutically acceptable carriers" for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

"Pharmaceutically acceptable salt" refers to salts of the compounds of the present invention derived from the combination of such compounds and an organic or inorganic acid (acid addition salts) or an organic or inorganic base (base addition salts). The compositions of the present invention may be used in either the free base or salt forms, with both forms being considered as being within the scope of the present invention.

The pharmaceutical compositions may be in any form which allows for the composition to be administered to a patient. For example, the composition may be in the form of a solid, liquid or gas (aerosol). Typical routes of administration include, without limitation, oral, topical, parenteral, sublingual, buccal, rectal, vaginal, intravenous, intradermal, transdermal, intranasal, intramucosal, or subcutaneous. The term parenteral as used herein includes iontophoretic (e.g., U.S. Pat. Nos. 7,033,598; 7,018,345; 6,970,739), sonophoretic (e.g., U.S. Pat. Nos. 4,780,212; 4,767,402; 4,948,587; 5,618,275; 5,656,016; 5,722,397; 6,322,532; 6,018,678), thermal (e.g., U.S. Pat. Nos. 5,885,211; 6,685,699), passive transdermal (e.g., U.S. Pat. Nos. 3,598,122; 3,598,123; 4,286,592; 4,314,557; 4,379,454; 4,568,343; 5,464,387; UK Pat. Spec. No. 2232892; U.S. Pat. Nos. 6,871,477; 6,974,588; 6,676,961), microneedle (e.g., U.S. Pat. Nos. 6,908,453; 5,457,041; 5,591,139; 6,033,928) administration and also subcutaneous injections, intravenous, intramuscular, intrasternal, intracavernous, intrathecal, intrameatal, intraurethral injection or infusion techniques. In a particular embodiment, a composition as described herein (including vaccine and pharmaceutical compositions) is administered intradermally by a technique selected from iontophoresis, microcavitation, sonophoresis or microneedles.

The pharmaceutical composition can be formulated so as to allow the active ingredients contained therein to be bioavailable upon administration of the composition to a subject. Compositions that will be administered to a subject take the form of one or more dosage units, where for example, a tablet may be a single dosage unit, and a container of one or more compounds of the invention in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, compositions can contain one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following carriers or excipients: sterile diluents such as water for injection, saline solution, preferably physiological saline, Ringer's solution, isotonic sodium chloride, fixed oils such as squalene, squalane, mineral oil, a mannide monooleate, cholesterol, and/or synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose.

In another embodiment, a composition of the invention is formulated in a manner which can be aerosolized.

It may also be desirable to include other components in a pharmaceutical composition, such as delivery vehicles including but not limited to aluminum salts, water-in-oil emulsions, biodegradable oil vehicles, oil-in-water emulsions, biodegradable microcapsules, and liposomes. Examples of additional immunostimulatory substances (co-adjuvants) for use in such vehicles are also described above and may include N-acetylmuramyl-L-alanine-D-isoglutamine (MDP), glucan, IL-12, GM-CSF, gamma interferon and IL-12.

While any suitable carrier known to those of ordinary skill in the art may be employed in the pharmaceutical compositions of this invention, the type of carrier will vary depending on the mode of administration and whether a sustained release is desired. For parenteral administration, such as subcutaneous injection, the carrier can comprise water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109. In this regard, it is preferable that the microsphere be larger than approximately 25 microns.

Pharmaceutical compositions may also contain diluents such as buffers, antioxidants such as ascorbic acid, polypeptides, proteins, amino acids, carbohydrates including glucose, sucrose or dextrins, chelating agents such as EDTA, glutathione and other stabilizers and excipients. Neutral buffered saline or saline mixed with nonspecific serum albumiskilln are exemplary appropriate diluents. For example, a product may be formulated as a lyophilizate using appropriate excipient solutions (e.g., sucrose) as diluents.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the antigen (e.g., GLA-antigen vaccine composition) or GLA (e.g., immunological adjuvant composition; GLA is available from Avanti Polar Lipids, Inc., Alabaster, AL; e.g., product number 699800) of from about 0.1 to about 10% w/v (weight per unit volume).

The composition may be intended for rectal administration, in the form, e.g., of a suppository which can melt in the rectum and release the drug. The composition for rectal administration may contain an oleaginous base as a suitable nonirritating excipient. Such bases include, without limitation, lanolin, cocoa butter and polyethylene glycol. In the methods of the invention, the pharmaceutical compositions/adjuvants may be administered through use of insert(s), bead(s), timed-release formulation(s), patch(es) or fast-release formulation(s).

VI. Methods of Use of the PEGylated Liposomes

Provided herein is a method of stimulating an immune response in a subject comprising administering any one of the PEGylated liposomes or compositions comprising the PEGylated liposomes provided herein. The PEGylated liposomes and compositions find uses for vaccination, therapeutics and diagnostics.

In one embodiment, a PEGylated liposome composition is used for the treatment or prevention of cancer.

In some embodiments, a pharmaceutical composition comprising a PEGylated liposome provided herein is a vaccine composition and is used as a vaccine. In some embodiments, the compositions described herein are used for stimulating an immune response in the subject (including a non-specific response and an antigen-specific response). In some embodiments, the immune response comprises a systemic immune response. In some embodiments, the immune response comprises a mucosal immune response.

In one embodiment, a PEGylated liposome composition is used to enhance protective immunity against an influenza-causing virus.

In one embodiment, a PEGylated liposome composition is used to enhance protective immunity against an amebiasis-causing organism.

In one embodiment, a PEGylated liposome composition is used to enhance protective immunity against *Entamoeba histolytica*.

In one embodiment, a PEGylated liposome composition is used to enhance protective immunity against influenza.

In one embodiment, a PEGylated liposome composition is used to enhance protective immunity against amebiasis.

In one embodiment, the PEGylated liposome composition is used to stimulate both a systemic immune response (characterized by an IgG immune response) and a mucosal immune response (characterized by an IgA immune response) in a subject, comprising intranasally administering any one of the PEGylated liposome compositions provided herein. In one embodiment, the PEGylated liposome composition is used to stimulate both a systemic immune response and a mucosal immune response in a subject, comprising intranasally administering a PEGylated liposome comprising a TLR4 agonist and a TLR7/8 agonist. In a related embodiment, the PEGylated liposome composition is used to stimulate both a systemic immune response and a mucosal immune response in a subject, comprising intranasally administering a PEGylated liposome comprising a GLA and a 3M-052. Surprisingly, the inventors have discovered that intranasal administration of a composition comprising a PEGylated liposome can generate a local mucosal response (in the nasal cavity), generate a systemic immune response, and generate a distal mucosal response (e.g. fecal, intestinal, and/or vaginal mucosal response).

In the embodiments provided herein, the subject is a mammal (e.g., an animal including farm animals (cows, pigs, goats, horses, etc.), pets (cats, dogs, etc.), and rodents (rats, mice, etc.), or a human). In one embodiment, the subject is a human. In another embodiment, the subject is a non-human mammal. In another embodiment, the non-human mammal is a dog, cow, or horse.

VII. Kits and Articles of Manufacture

Also contemplated in certain embodiments are kits comprising the herein described PEGylated liposomes and compositions, which may be provided in one or more containers. In one embodiment all components of the compositions are present together in a single container, but the invention embodiments are not intended to be so limited and also contemplate two or more containers in which, for example, an immunological adjuvant composition is separate from, and not in contact with, the antigen component. By way of non-limiting theory, it is believed that in some cases administration only of the PEGylated liposome composition as an immunological adjuvant composition may be performed beneficially, whilst in other cases such administration may beneficially be separated temporally and/or spatially (e.g., at a different anatomical site) from administration of the antigen, whilst in still other cases administration to the subject is beneficially conducted of a vaccine composition as described herein and containing both antigen and adjuvant composition, and optionally other herein described components as well.

In some embodiments, one vial of the kit comprises a composition comprising PEGylated liposomes, and a second vial of the kit contains an agent. In some embodiments, the kit comprises a third vial containing an optional agent.

The kits of the invention may further comprise instructions for use as herein described or instructions for mixing the materials contained in the vials. In some embodiments, the material in the vial is dry or lyophilized. In some embodiments, the material in the vial is liquid.

A container according to such kit embodiments may be any suitable container, vessel, vial, ampule, tube, cup, box, bottle, flask, jar, dish, well of a single-well or multi-well apparatus, reservoir, tank, or the like, or other device in which the herein disclosed compositions may be placed, stored and/or transported, and accessed to remove the contents. Typically such a container may be made of a material that is compatible with the intended use and from which recovery of the contained contents can be readily achieved. Non-limiting examples of such containers include glass and/or plastic sealed or re-sealable tubes and ampules, including those having a rubber septum or other sealing means that is compatible with withdrawal of the contents using a needle and syringe. Such containers may, for instance, by made of glass or a chemically compatible plastic or resin, which may be made of, or may be coated with, a material that permits efficient recovery of material from the container and/or protects the material from, e.g., degradative conditions such as ultraviolet light or temperature extremes, or from the introduction of unwanted contaminants including microbial contaminants. The containers are preferably sterile or sterilizable, and made of materials that will be compatible with any carrier, excipient, solvent, vehicle or the like, such as may be used to suspend or dissolve the herein described vaccine compositions and/or immunological adjuvant compositions and/or antigens and/or recombinant expression constructs, etc.

VIII. Exemplary Embodiments

In a first embodiment, the present invention is directed to, inter alia, a liposome comprising a cholesterol; a non-PEGylated neutral lipid; and a PEGylated lipid, wherein the average molecular weight of the PEG in the PEGylated lipid is about 5000 Daltons or less.

The present invention also provides in a second embodiment, any of the liposomes of the $1^{st}$ embodiment, wherein the average molecular weight of the PEG in the PEGylated lipid ranges from about 750 Daltons to about 5000 Daltons; liposomes of the first embodiment, wherein the average molecular weight of the PEG in the PEGylated lipid is about 2000 Daltons or less; or liposomes of the first embodiment, wherein the average molecular weight of the PEG in the PEGylated lipid is about 750 Daltons.

The present invention provides in a third embodiment, any of the liposome of the $1^{st}$ or $2^{nd}$ embodiment, wherein the lipid component of the PEGylated lipid comprises a neutral lipid; wherein the lipid component of the PEGylated lipid comprises a $C_{14}$ alkyl chain, a $C_{16}$ alkyl chain, or a $C_{18}$ alkyl chain; wherein the lipid component of the PEGylated lipid is DSPE, DPPC, DOPC, DLPC, DMPC, DSPC, POPC, DPPE, or DMPE; wherein the lipid component of the PEGylated lipid is DSPE; or wherein the lipid component of the PEGylated lipid is DPPE.

The present invention provides in a fourth embodiment, any of the liposomes of the $1^{st}$, $2^{nd}$ or $3^{rd}$ embodiments, wherein the non-PEGylated neutral lipid comprises a $C_{14}$ alkyl chain, a $C_{16}$ alkyl chain, or a $C_{18}$ alkyl chain; wherein the non-PEGylated neutral lipid is DPPC, DOPC, DLPC, DMPC, DSPC, POPC, DPPE, or DMPE; or wherein the non-PEGylated neutral lipid is DPPC.

The present invention provides in a fifth embodiment, any of the liposomes of the $1^{st}$, $2^{nd}$ $3^{rd}$, or $4^{th}$ embodiments, wherein the liposome is stable; wherein the liposome is stable for at least 1 month at a temperature of about 2° C. to about 8° C.; wherein the liposome is stable for at least 1 month at a temperature of about 25° C.; or wherein the liposome is stable for at least 1 month at a temperature of about 37° C.

The present invention provides in a sixth embodiment, any of the liposomes of the Pt, $2^{nd}$ $3^{rd}$, $4^{th}$ or $5^{th}$ embodiments, wherein the polydispersity index of the liposome is maintained at about 0.3 or less.

The present invention provides in a seventh embodiment, any of the liposomes of the Pt, $2^{nd}$ $3^{rd}$, $4^{th}$, $5^{th}$ or $6^{th}$ embodiments, wherein the size of the liposome is less than or about 450 nm; wherein the size of the liposome is maintained at less than or about 450 nm; or wherein the size of the liposome ranges from about 50 nm to about 300 nm.

The present invention provides in an eighth embodiment, any of the liposomes of the Pt, $2^{nd}$ $3^{rd}$, $4^{th}$, $5^{th}$, $6^{th}$ or $7^{th}$ embodiments, wherein the molar percentage (mol %) of the PEGylated lipid in the liposome ranges from about 1 mol % to about 25 mol %; wherein the mol % of the PEGylated lipid in the liposome ranges from about 1 mol % to about 10 mol %; or wherein the mol % of the PEGylated lipid in the liposome is about 5 mol %.

The present invention provides in a ninth embodiment, any of the liposomes of the $1^{st}$, $2^{nd}$ $3^{rd}$, $4^{th}$, $5^{th}$, $6^{th}$, $7^{th}$ or $8^{th}$ embodiment, wherein the mol % of cholesterol in the liposome ranges from about 1 mol % to about 50 mol %; or wherein the mol % of the cholesterol in the liposome is about 50 mol %.

The present invention provides in a tenth embodiment, any of the liposomes of the $1^{st}$, $2^{nd}$ $3^{rd}$, $4^{th}$, $5^{th}$, $6^{th}$, $7^{th}$ or $8^{th}$, $9^{th}$ or embodiment, wherein the mol % of non-PEGylated lipid in the liposome ranges from about 45 mol % to about 98 mol % or wherein the mol % of non-PEGylated lipid in the liposome is about 45 mol %.

The present invention provides in an eleventh embodiment, any of the liposomes of the $1^{st}$, $2^{nd}$ $3^{rd}$, $4^{th}$, $5^{th}$, $6^{th}$, $7^{th}$ or $8^{th}$, $9^{th}$ or $10^{th}$ embodiment, wherein the lipid molar ratio of the non-PEGylated neutral lipid:cholesterol:PEGylated lipid is about 9.8:5.7:0.8 or wherein the lipid molar ratio of the non-PEGylated neutral lipid:cholesterol:PEGylated lipid is about 18:5.5:3.

The present invention provides in a twelfth embodiment, any of the liposomes of the $1^{st}$, $2^{nd}$, $3^{rd}$, $4^{th}$, $5^{th}$, $6^{th}$, $7^{th}$, $8^{th}$, $9^{th}$, $10^{th}$, or $11^{th}$ embodiments, wherein the liposome further comprises at least one TLR agonist; wherein the liposome comprises a TLR2 agonist, a TLR3 agonist, a TLR4 agonist, a TLR5 agonist, a TLR6 agonist, a TLR7 agonist, a TLR8 agonist, a TLR7/8 agonist, or a TLR9 agonist; wherein the liposome comprises a TLR4, SLA, GLA, 3D-MPL, R837, or R848; wherein the liposome comprises a TLR agonist with a hydrophobic tail; wherein the liposome comprises a TLR7/8 agonist; wherein the liposome comprises a TLR7 agonist, wherein the liposome comprises a TLR8 agonist; wherein the liposome comprises a TLR7/8 agonist comprising an imidazoquinoline or an imidazoquinoline-containing compound; wherein the liposome comprises 3M-052; wherein the liposome comprises R848; wherein the liposome comprises a TLR4 agonist; wherein the liposome comprises 3D-MPL; wherein the liposome comprises GLA; wherein the liposome comprises a synthetic GLA of Formula (V) as provided herein or a pharmaceutically acceptable salt thereof and any of the corresponding embodiments of Formula (V) or a pharmaceutically acceptable salt thereof; wherein the liposome comprises a synthetic GLA of Formula (VI) as provided herein or a pharmaceutically acceptable salt thereof and any of the corresponding embodiments of Formula (VI) or a pharmaceutically acceptable salt thereof; or wherein the liposome comprises a synthetic GLA of formula:

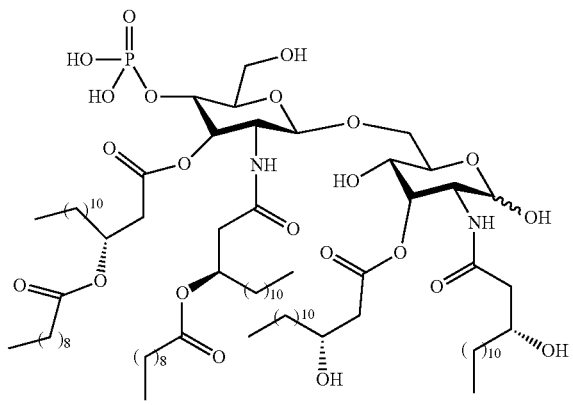

or a pharmaceutically acceptable salt thereof; wherein the liposome comprises a TLR4 agonist and a TLR7/8 agonist; wherein the liposome comprises any one of the TLR4 or TLR7/8 agonists described herein; or wherein the liposome comprises GLA and 3M-052.

The present invention provides in a thirteenth embodiment, any of the liposomes of the $1^{st}$, $2^{nd}$, $3^{rd}$, $4^{th}$, $5^{th}$, $6^{th}$, $7^{th}$, $8^{th}$, $9^{th}$, $10^{th}$, $11^{th}$ or $12^{th}$ embodiments, wherein the liposome comprises at least one agent; wherein the liposome comprises at least one agent that comprises a polypeptide, a polynucleotide, an antigen, an adjuvant, a diagnostic agent, a therapeutic agent, or an organism; wherein the liposome comprises at least one agent that comprises an antigen; wherein the liposome comprises at least one agent that comprises an antigen and wherein the antigen comprises an amebiasis-related antigen, LecA, an influenza-related antigen, H5N1, a tuberculosis-related antigen, ID91, ID93, an antigen from BCG, a hepatitis virus-related antigen, a Hepatitis B antigen, a Hepatitis C antigen, a HIV-related antigen, or a cancer-related antigen.

The present invention provides in a fourteenth embodiment, a composition comprising any of the liposomes of the $1^{st}$, $2^{nd}$, $3^{rd}$, $4^{th}$, $5^{th}$, $6^{th}$, $7^{th}$, $8^{th}$, $9^{th}$, $10^{th}$, $11^{th}$, $12^{th}$ or $13^{th}$ embodiments or a composition comprising any of the liposomes of the $1^{st}$, $2^{nd}$, $3^{rd}$, $4^{th}$, $5^{th}$, $6^{th}$, $7^{th}$, $8^{th}$, $9^{th}$, $10^{th}$, $11^{th}$, $12^{th}$ or $13^{th}$ embodiments and a pharmaceutically acceptable carrier, excipient, or diluent. The composition can be, for example, a vaccine, a therapeutic or a diagnostic.

The present invention provides in a fifteenth embodiment, a method of stimulating an immune response in a subject comprising administering to the subject the liposome or composition of any one of the $1^{st}$, $2^{nd}$, $3^{rd}$, $4^{th}$, $5^{th}$, $6^{th}$, $7^{th}$, $8^{th}$, $9^{th}$, $10^{th}$, $11^{th}$, $12^{th}$ $13^{th}$, or $14^{th}$ embodiments whereby stimulating an immune response in the subject. The immune response can be, for example, a non-specific immune response; an antigen-specific immune response; a systemic immune response; a mucosal immune response; or an intestinal, fecal, or vaginal mucosal immune response. The compositions can be used, for example, for the treatment or prevention of cancer; as a vaccine; to enhance protective immunity against an influenza-causing virus; to enhance protective immunity against an amebiasis-causing organism; to enhance protective immunity against *Entamoeba histolytica*; to enhance protective immunity against influenza; or to enhance protective immunity against amebiasis. The route of administration of the composition can be oral, topical, parenteral, sublingual, buccal, rectal, vaginal, intravenous, intradermal, transdermal, intranasal, intramucosal, or subcutaneous. The liposome or composition can be administered with a retinoic acid co-adjuvant. The subject can be, for example, a human or a non-human mammal.

The present invention provides in a sixteenth embodiment, a method of inducing a Th1 response in a subject comprising administering to the subject the liposome or composition of any one of the $1^{st}$, $2^{nd}$, $3^{rd}$, $4^{th}$, $5^{th}$, $6^{th}$, $7^{th}$, $8^{th}$, $9^{th}$, $10^{th}$, $1^{th}$, $12^{th}$ $13^{th}$, or $14^{th}$ embodiments, whereby a Th1 response is induced in the subject. The immune response can be, for example, a non-specific immune response, an antigen-specific immune response, a systemic immune response, a mucosal immune response, or an intestinal, fecal, or vaginal mucosal immune response. The compositions can be used, for example, for the treatment or prevention of cancer, as a vaccine; to enhance protective immunity against an influenza-causing virus; to enhance protective immunity against an amebiasis-causing organism; to enhance protective immunity against *Entamoeba histolytica*; to enhance protective immunity against influenza; or to enhance protective immunity against amebiasis. The route of administration of the composition can be oral, topical, parenteral, sublingual, buccal, rectal, vaginal, intravenous, intradermal, transdermal, intranasal, intramucosal, or subcutaneous. The liposome or composition can be administered with a retinoic acid co-adjuvant. The subject can be, for example, a human or a non-human mammal.

The present invention provides in a seventeenth embodiment, a method of stimulating a systemic immune response and a mucosal immune response in a subject, comprising intranasally administering the liposome or composition of any one of the $1^{st}$, $2^{nd}$, $3^{rd}$, $4^{th}$, $5^{th}$, $6^{th}$, $7^{th}$, $8^{th}$, $9^{th}$, $10^{th}$, 11th, $12^{th}$, $13^{th}$, or $14^{th}$ embodiments to the subject. The mucosal immune response can comprise, for example, an intestinal, fecal or vaginal mucosal immune response. The mucosal immune response can be, for example, distal to the nasal cavity. The liposome or composition can be administered with a retinoic acid co-adjuvant. The subject can be, for example, a human or a non-human mammal.

The present invention provides in an eighteenth embodiment, a method of making any of the PEGylated liposomes described herein, comprising: a) mixing the non-PEGylated neutral lipid, the PEGylated lipid, and the cholesterol in an organic solvent; b) evaporating the organic solvent, whereby generating a lipid film; c) rehydrating the lipid film in a buffer; and sonicating, microfluidizing, or extruding the rehydrated product of step c). Step a) can further comprise the step of mixing a TLR agonist. The organic solvent can be, for example, chloroform. The rehydrated product of step (c) can be, for example, sonicated, and then microfluidized. The method can further comprise admixing an agent to the PEGylated liposome. The agent can be any one of the agents described herein.

The present invention provides in a nineteenth embodiment, a squalene-based oil in water emulsion comprising a TLR agonist, squalene, and unsaturated phosphatidylcholine. In such embodiments, emulsions manufactured with the unsaturated phosphatidylcholine as compared to a saturated phospholid, e.g., DMPC, resulted in higher recovery of TLR agonist, i.e., higher concentration of TLR agonist in the final formulation when starting with same initial concentration of TLR agonist.

The present invention provides in a twentieth embodiment, a squalene-based oil in water emulsion comprising a TLR agonist, squalene, and unsaturated phosphatidylcholine wherein squalene is at a concentration between about 30 to about 40 mg/ml and the unsaturated phosphatidylcholine is at a concentration of from about 5 to about 10 mg/ml.

The present invention provides in a twenty-first embodiment, a squalene-based oil in water emulsion optimized for formulation with a TLR agonist, typically a TLR agonist that is insoluble in water (negligible solubility in water) comprising the TLR agonist, squalene, and unsaturated phosphatidylcholine (e.g., egg phosphatidylcholine) wherein squalene is at a concentration between about 34 mg/ml and the unsaturated phosphatidylcholine is at a concentration of from about 7-8 mg/ml or about 7.6 mg/ml.

The present invention provides in a twenty-second embodiment, any one of the emulsions of the $19^{th}$, $20^{th}$, or $21^{st}$ embodiment, further optionally comprising a co-emulsifying agent, a tonicity agent and a buffering agent. In any of the embodiments described herein, the co-emulsifying agent can be for example a non-ionic linear triblock copolymer such as a poloxamer (e.g., poloxamer 188). In any of the embodiments described herein, the tonicity agent can be for example, a polyol such as mannitol or glycerol. In any of the embodiments described herein, the buffering agent can be for example, a phosphate buffering agent such as, for example, an ammonium phosphate buffer. The co-emulsifying agent, when present in the emulsion is preferably present in the emulsion at a concentration of 0.1 to about 2 mg/ml, more preferably at about 0.5 mg/ml, most preferably at about 0.36 mg/ml. The tonicity agent, when present in the emulsion is present in an amount sufficient to cause the composition to have an osmolality of about 250-350 mOsm/kg, preferably 270-315 mOsm/kg.

The present invention provides in a twenty-third embodiment, any one of the emulsions of the $19^{th}$, $20^{th}$, $21^{st}$ or $22^{nd}$ embodiment, wherein the TLR agonist (a) is synthetic (b) is insoluble in water (c) is an imidazoquinoline or imidazoquinoline-containing compound (d) has a hydrophobic tail (e) is 3M-052 or any combinations thereof. The emulsions can further comprise at least one agent; wherein the at least one agent can be a polypeptide, a polynucleotide, an antigen, an adjuvant, a diagnostic agent, a therapeutic agent, or an organism. Exemplary agents include, for example, an amebiasis-related antigen, LecA, an influenza-related antigen, H5N1, a tuberculosis-related antigen, ID91, ID93, an antigen from BCG, a hepatitis virus-related antigen, a Hepatitis B antigen, a Hepatitis C antigen, a HIV-related antigen, or a cancer-related antigen.

The present invention provides in a twenty-fourth embodiment, a method of making the emulsions of the $19^{th}$, $20^{th}$, $21^{st}$ $22^{nd}$ and $23^{rd}$ embodiments comprising combining the TLR agonist with the unsaturated phosphatidylcholine in an organic solvent. Any organic solvent capable of solubilizing both the TLR agonist and the unsaturated phosphatidylcholine is suitable for use including, for example, ethanol, DMF, and chloroform. The method can further comprise the step of (a) removing the chloroform by any suitable method including evaporation to generate a lipid film (b) adding the squalene to the dried lipid film and (c) and mixing the resultant mixture, e.g., by sonication (e.g., in a 60 C water bath) or microfluidization or simple agitation.

The present invention provides in a twenty-fifth embodiment, pharmaceutical compositions comprising any one of the emulsions of the $19^{th}$, $20^{th}$, $21^{st}$, $22^{nd}$ and $23^{rd}$ embodiments; and a pharmaceutically acceptable carrier.

The present invention provides in a twenty-sixth embodiment, a method of stimulating an immune response in a subject comprising administering any one of the emulsions of the $19^{th}$, $20^{th}$, $21^{st}$, $22^{nd}$ and $23^{rd}$ embodiments or pharmaceutical compositions of the $25^{th}$ embodiment to a subject. The immune response can be, for example, a Th1 immune response; a non-specific immune response, an antigen-specific immune response, a systemic immune response, a mucosal immune response, or an intestinal, fecal, or vaginal mucosal immune response. The emulsions or compositions can be used, for example, for the treatment or prevention of cancer, as a vaccine; to enhance protective immunity against an influenza-causing virus; to enhance protective immunity against an amebiasis-causing organism; to enhance protective immunity against *Entamoeba histolytica*; to enhance protective immunity against influenza; or to enhance protective immunity against amebiasis. The route of administration of the composition can be oral, topical, parenteral, sublingual, buccal, rectal, vaginal, intravenous, intradermal, transdermal, intranasal, intramucosal, or subcutaneous. The liposome or composition can be administered with a retinoic acid co-adjuvant. The subject can be, for example, a human or a non-human mammal.

The following Examples are offered by way of illustration and not by way of limitation.

EXAMPLES

Example 1: Formulation and Testing of TLR Ligand Containing Liposomes for Amebiasis Vaccines Materials and Methods Formulations with Adjuvants, LecA Antigen All adjuvants were prepared at the Infectious Disease Research Institute (IDRI, Seattle, WA) and provided as 2× or 5× concentrated formulations for mixing with antigen immediately prior to injection.

The LecA antigen was manufactured by TECHLAB (Blacksburg, VA) as described (Barroso L, Abhyankar M, Noor Z, Read K, Pedersen K, White R, et al. Expression, purification, and evaluation of recombinant LecA as a candidate for an amebic colitis vaccine. Vaccine. 2014; 32(10): 1218-). Glucopyranosyl lipid adjuvant (GLA), 1,2-dipalmitoyl-sn-glycero-3-phosphocholine (DPPC), 1,2-distearoyl-sn-glycero-3-phosphoethanolamine-N-[methoxy (polyethylene glycol)-750] (DSPE-PEG750), and 1,2-distearoyl-sn-glycero-3-phosphoethanolamine-N-[methoxy (polyethylene glycol)-2000] (DSPE-PEG2000) were obtained from Corden Pharma (Liestal, Switzerland) or Avanti Polar Lipids (Alabaster, AL). 3M-052 was provided courtesy of 3M Drug Delivery Systems (St. Paul, MN). Cholesterol and buffer salts were purchased from J. T. Baker (San Francisco, CA). GLA used in the examples has the structure of Formula (VI) wherein $R^1$, $R^3$, $R^5$ and $R^6$ are $C_{11}$ alkyl; and $R^2$ and $R^4$ are $C_{13}$ alkyl.

PEGylated liposome formulations were manufactured by combining DPPC, cholesterol, DSPE-PEG750 or DPPE-PEG2000, and 3M-052 and/or GLA in chloroform. The lipid molar ratio was 9.8:5.7:0.8 (DPPC:cholesterol:PEGylated lipid). The organic solvent from the formulations was then evaporated for at least 12 h using a rotary evaporator. The lipid thin film was rehydrated in 25 mM ammonium phosphate buffer (pH ~5.7) and sonicated in a Crest Powersonic CP230D (Trenton, NJ) water bath at ~60° C. for up to 30 min. The formulation was then microfluidized at 10,000-30,000 psi for 5-6 passes with a recirculating water chiller set at 10° C. Liposomes were filtered through a 0.8/0.2 µm double membrane polyethersulfone filter and stored at 5° C., ambient temperature, 37° C., or 60° C. An alternative to microfluidization is sonication.

Squalene-in-water emulsions were prepared by microfluidization (M110P, Microfluidics Corp) at 30,000 psi essentially as described (Fox et al. Vaccine 2013, 31:5848). Alum-adsorbed formulations were prepared by mixing an aqueous lipid component of the PEGylated lipid-based suspension of GLA or an aqueous solution of CpG 1826 to Alhydrogel® (Brenntag Biosector) as previously described (Fox et al. J Pharm Sci 2012, 101:4357 and Fox et al.)

Physicochemical Stability Measurements

Emulsion and liposome particle sizes were measured by dynamic light scattering after 1:100 dilution in water. The short-term (≤24 h) physicochemical compatibility of the antigen-adjuvant mixture was evaluated by monitoring particle size, visual appearance, and antigen primary structure immediately after mixing and 4 and 24 h after mixing, with mixtures stored at 5° C. and ambient temperature. The antigen was first diluted in saline to 0.1 mg/ml, and subsequently mixed in 1:1 volume with the liposomal adjuvant formulation. Particle size was measured as described above except that one cuvette was prepared instead of three. SDS-PAGE was conducted by mixing 50 µL sample with 50 µL 4× reducing sample buffer and 100 µL 20% SDS. The sample was heated at 90° C. for 5 min and stored at −20° C., after which they were reheated for 1 min at 90° C. and loaded onto a polyacrylamide gel with Tris-glycine running buffer for 65 m at 180 V, followed by staining with Coomassie blue.

Using an HPLC method, the concentration of 3M-052 was determined by UV absorbance detection at 320 nm and the concentration of GLA was determined by charged aerosol detection. The HPLC method was described previously (Misquith A, Fung M, Dowling Q M, Guderian J A, Vedvick T S, Fox C B. In vitro evaluation of TLR4 agonist activity: formulation effects. Coll Surf B: Biointerfaces. 2014; 113: 312-9). Adjuvant concentrations were considered within specification if measured values were within +/−20% of target concentration. Liposome particle size and size polydispersity was evaluated using a Malvern Instruments (Worcestershire, UK) Zetasizer Nano-S or -ZS. The formulation was diluted 100-fold in ultrapure (18.2 MS2) water in a 1.5 ml polystyrene disposable cuvette. For each formulation, three separate cuvettes were prepared. All size measurements were then made three times for each cuvette. On rare occasions dust particles result in obvious measurement deviations; in such cases, the measurement from the suspected cuvette is discarded from the set. TLR ligand concentration, particle size, and visual appearance were monitored regularly as indicated.

Immunizations

Four to six week old CBA/J male mice were purchased from the Jackson Labs. Non-tagged LecA antigen was purified at the TechLab Inc. (Blacksburg, VA) and 5 ug antigen was used per immunization per mouse. All mice studies were carried out strictly in accordance with the IACUC regulations. For subcutaneous immunization in the neck region, LecA was mixed with the respective adjuvant (Table-1) and volume brought up to 100 ul with saline for injection. Intranasal immunizations were carried out under anesthesia and typically 10 ul of antigen-adjuvant mixture was used per nostril. A two week interval was maintained between successive immunizations for all the regimens. For experiments involving weekly dose of all trans retinoic acid (RA), each mouse received 150 ug all trans retinoic acid (Sigma) dissolved in a 50 ul final volume of DMSO intraperitoneally. RA stock was stored at −80° C. and protected from light. All adjuvants were stored at 4° C. and formulations prepared aseptically just before immunization.

Measurement of Immunogenicity

Antibody titers were measured by ELISA using 96-well plates coated with 0.5 ug Lectin per well. Plasma samples were diluted appropriately and antigen specific IgG subtypes were measured using 1:10,000 diluted horseradish peroxidase conjugated goat anti-mouse IgG1 and IgG2a detection antibodies (Southern Biotechnology). Stool supernatants were prepared as described (Guo X, Barroso L, Becker S M, Lyerly D M, Vedvick T S, Reed S G, et al). Protection against intestinal amebiasis by a recombinant vaccine is transferable by T cells and mediated by gamma interferon. Infect Immun. 2009 September; 77(9):3909-18). In short, freshly collected stool samples were resuspended (5 ul diluent per mg of stool) in PBS containing protease inhibitor cocktail (Roche) and vigorously mixed for 5 minutes. Insoluble material was removed through two consecutive spins at 3000 rpm and 12,000 rpm and supernatant stored at −20° C. Appropriately diluted stool supernatants were used for ELISA and horseradish peroxidase conjugated goat anti-mouse IgA at 1:5000 dilution was used as a secondary antibody. Antibody units were determined using standard curves.

For the measurement of extracellular cytokines, splenocytes were re-stimulated with 50 µg/ml LecA for 72 h and supernatants analyzed by a multiplex suspension array system using Luminex beads (BioRad) (Guo X, Barroso L, Becker S M, Lyerly D M, Vedvick T S, Reed S G, et al. Protection against intestinal amebiasis by a recombinant vaccine is transferable by T cells and mediated by gamma interferon. Infect Immun. 2009 September; 77(9):3909-18). Samples were run undiluted as per manufacturer's instructions and measured in picograms per milliliter of supernatant.

Culture Conditions and Challenge Experiments

Trophozoites originally derived from HM1: IMSS (ATCC) passed sequentially through mice ceca were used for the challenge experiments. Trophozoites were maintained in a trypsin-yeast extract-iron (TYI-S-33) medium supplemented with 2% Diamond vitamins, 13% heat inactivated bovine serum (Gemini Labs) and 100 U/ml penicillin plus 100 ug/ml streptomycin (Invitrogen) (Diamond L S, Harlow D R, Cunnick C C. A new medium for the axenic cultivation of Entamoeba histolytica and other Entamoeba. Trans R Soc Trop Med Hyg. 1978; 72(4):431-2). Mice from immunized and control groups were challenged intracecally four weeks after the final boost with two million trophozoites in 150 ul medium following laparotomy (Houpt E, Barroso L, Lockhart L, Wright R, Cramer C, Lyerly D, et al. Prevention of intestinal amebiasis by vaccination with the *Entamoeba histolytica* Gal/GalNac lectin. Vaccine. 2004 Jan. 26; 22(5-6):611-7). Mice were euthanized a week after the challenge. Ceca were rinsed with 1 ml PBS, 300 ul of cecal rinse was cultured in TYI-S-33 broth for up to five days and 200 ul used for antigen load ELISA. Vaccine efficacy was calculated as 100×(1-(% of vaccinated mice with infection)/(% of sham mice with infection) (Guo X, Barroso L, Becker S M, Lyerly D M, Vedvick T S, Reed S G, et al. Protection against intestinal amebiasis by a recombinant vaccine is transferable by T cells and mediated by gamma interferon. Infect Immun. 2009 September; 77(9): 3909-18; Soong C J, Kain K C, Abd-Alla M, Jackson T F, Ravdin J I. A recombinant cysteine-rich section of the *Entamoeba histolytica* galactose-inhibitable lectin is efficacious as a subunit vaccine in the gerbil model of amebic liver abscess. J Infect Dis. 1995 March; 171(3):645-51).

Fecal Antigen Detection

Fecal antigen in the cecal contents was detected using the E. his II ELISA kit (TechLab Inc., Blacksburg, VA). An optical density at 450 nm of ≥0.05 above the negative control was considered positive. A standard curve was generated using purified LecA.

Adherence Assay

Chinese hamster ovary (CHO) cells were grown in α-MEM medium and *E. histolytica* trophozoites were grown as described above. *E. histolytica* trophozoites were preincubated with a tenfold dilution of fecal supernatants from control or immunized groups on ice for 1 h. Trophozoites and CHO cells were then mixed at a 1:20 ratio and incubation continued for 90 min on ice in round bottom polystyrene tubes. Just prior to microscopic counting, the tubes were briefly vortexed and cells counted on a hemocytometer. Adherence was measured as the number of trophozoites having at least 3 adherent CHO cells and reported as % rosette formation. Each sample was run in triplicate and a minimum of 100 amebae were counted (Barroso L, Abhyankar M, Noor Z, Read K, Pedersen K, White R, et al. Expression, purification, and evaluation of recombinant LecA as a candidate for an amebic colitis vaccine. Vaccine. 2014 Feb. 26; 32(10):1218-24; Ravdin J I, Guerrant R L. Role of adherence in cytopathogenic mechanisms of *Entamoeba histolytica*. Study with mammalian tissue culture cells and human erythrocytes. J Clin Invest. 1981 November; 68(5):1305-13).

Statistical Analysis

All analyses were performed using Graph Pad Prism software. Proportions of infected and uninfected mice from challenge trials were analyzed using Fisher's exact test. Antigen loads, antibody titers and adherence inhibition differences were analyzed using Mann-Whitney test.

Results

Physiochemical Stability—

Figure 1C:
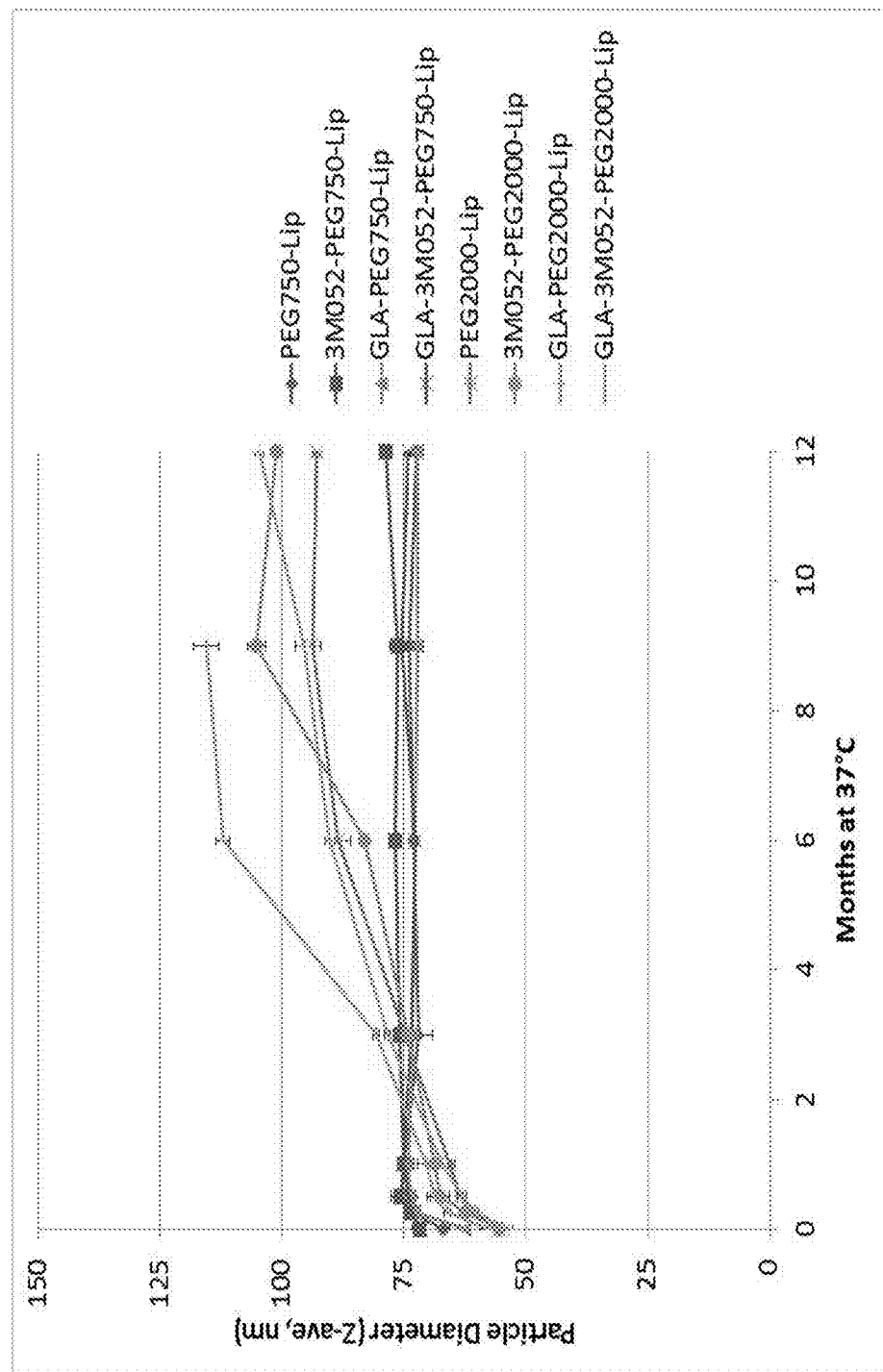
Figure 1D:
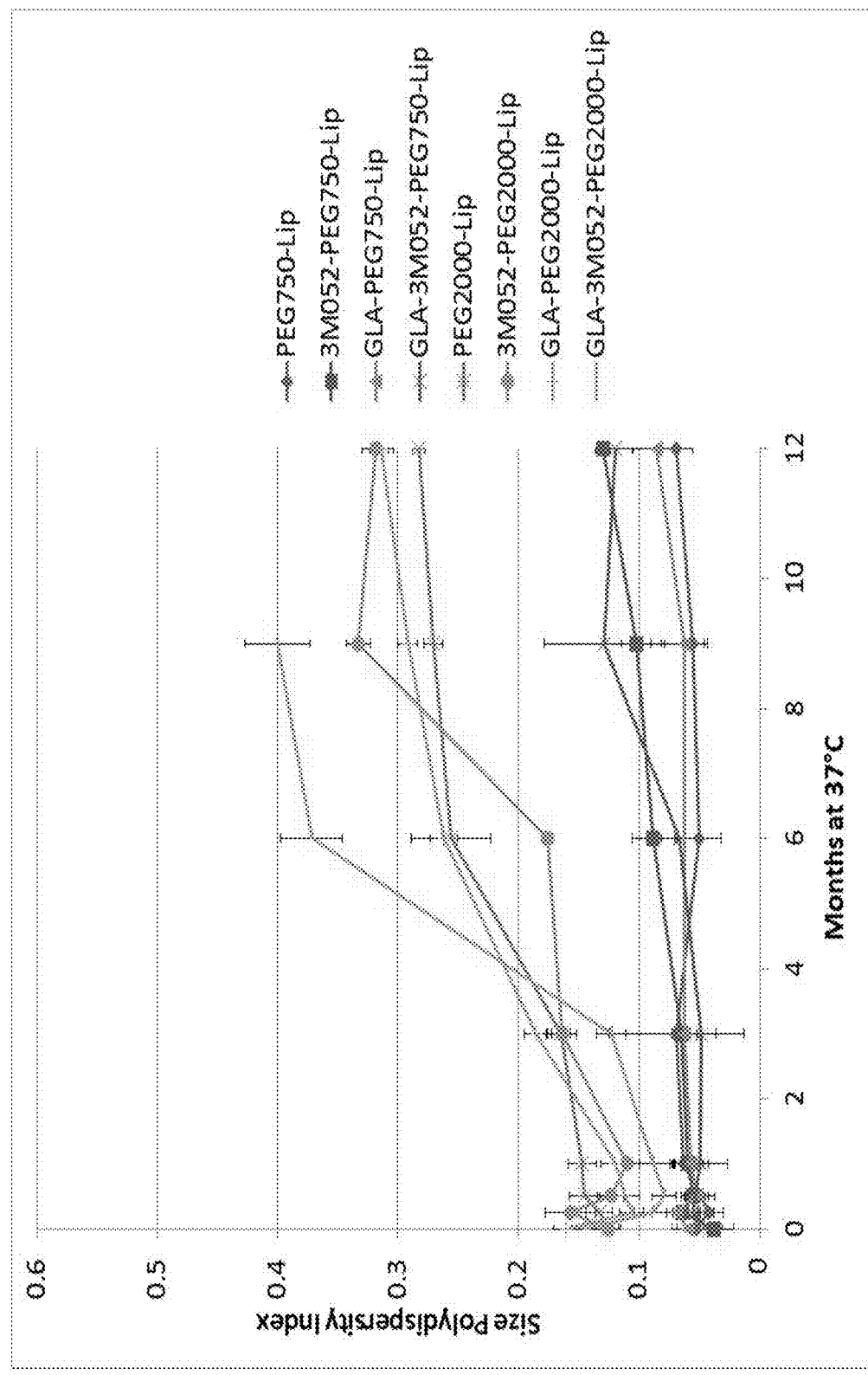

Liposome stability was monitored by dynamic light scattering (particle size and size polydispersity), visual appearance, and HPLC (GLA and 3M-052 concentration). Particle size and size polydispersity values showed little or no change over 12 months at 5° C., although the polydispersity values for liposomes containing DSPE-PEG2000 were significantly higher than the polydispersity values for liposomes containing DSPE-PEG750 (FIG. 1A). The visual appearance of the liposomes was consistently translucent and homogeneous and did not change over time. When stored at 37° C., liposomes containing DSPE-PEG2000 showed greater change in particle size and size polydispersity over time compared to liposomes containing DSPE-PEG750 (FIGS. 1C-1D). GLA and 3M-052 concentrations did not change over 12 months in samples stored at 5° C. At 37° C., the rate of GLA loss was greater than that of 3M-052, with >40% of GLA loss after 6 months, whereas no detectable loss had occurred with 3M-052.

Figure 2:
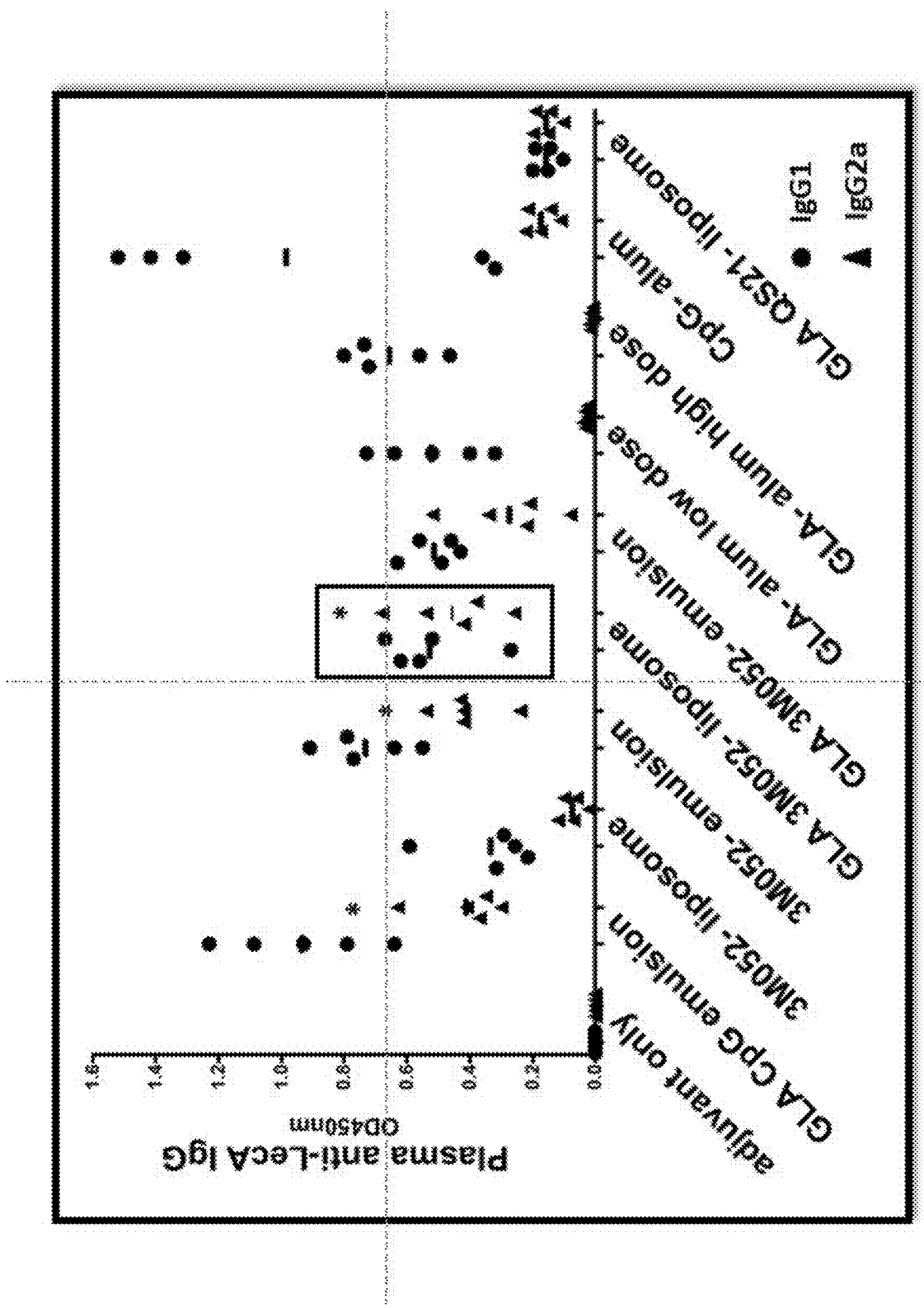
FIG. 2 shows the IgG1 and IgG2a response of various formulations, as determined by ELISA. The figure depicts comparison of plasma IgG1 and IgG2a titers following the immunization of mice with various formulations of the LecA antigen mixed with the corresponding adjuvant.

To evaluate the short-term (≤24 h) compatibility of adjuvant and LecA antigen after mixing, stock antigen was diluted in saline and then mixed in 1:1 volume ratio with adjuvant to mimic the planned mixing procedure for the in vivo immunization studies described below. Formulations had a translucent, homogeneous appearance before and after mixing with antigen. Overall, there was little (<15%) or no change in particle size over 24 h after mixing with antigen whether stored at 5° C. or ambient temperature although liposomes containing DSPE-PEG2000 showed a slightly greater tendency to increase in size compared to the liposomes containing the shorter PEG length (DSPE-PEG750). Overall, the presence of GLA, 3M-052, or both agonists together did not appear to affect the particle size compatibility results. Likewise, size polydispersity values changed little, although polydispersity was higher for liposomes containing DSPE-PEG2000 compared to liposomes containing DSPE-PEG750. SDS-PAGE analysis of the antigen-adjuvant mixtures indicated no change in antigen primary structure at any timepoint or storage condition over 24 h, regardless of liposome composition, with a uniform single band near the expected MW. Together, these data indicate that the antigen-adjuvant mixture demonstrated acceptable short term compatibility for at least up to 24 h at 5° C. or ambient temperature.

Evaluation of Immunogenicity and Selection of a Liposome Formulation

Using an *E. histolytica* recombinant adhesin LecA as an immunogen, adjuvants that could generate a balanced immune response were screened for. Adjuvants containing synthetic TLR agonists were prepared as shown in Table 2 and their ability to generate an antigen specific humoral response was evaluated.

TABLE 2

Adjuvants Containing TLR agonists

| Adjuvant | Agonists | Formulation | IgG2a/IgG1 ratio |
|---|---|---|---|
| GLA CpG Emulsion | TLR-4 (20 ug GLA), TLR-9 (25 ug CpG) | Oil-in-water emulsion (2% v/v squalene) | 0.44 |
| 3M-052 Liposome | TLR-7/8 (2 ug 3M-052) | Liposome (4 mg/ml or 11 mg/ml phospholipid) | 0.22 |
| 3M-052 Emulsion | TLR-7/8 (2 ug 3M-052) | Oil-in-water emulsion (2% v/v squalene) | 0.56 |
| GLA 3M-052 Liposome | TLR-4 (5 ug GLA), TLR-7/8 (2 ug 3M-052) | Liposome (4 mg/ml or 11 mg/ml phospholipid) | 0.86 |
| GLA 3M-052 Emulsion | TLR-4 (5 ug GLA), TLR-7/8 (2 ug 3M-052) | Oil-in-water emulsion (2% v/v squalene) | 0.53 |
| GLA Alum Low dose | TLR-4 (5 μg GLA) | Alum (0.2 mg/ml $Al^{+3}$) | 0.06 |
| GLA Alum High dose | TLR-4 (20 μg GLA) | Alum (0.2 mg/ml $Al^{+3}$) | 0.02 |
| CpG Alum | TLR-9 (25 ug CpG) | Alum (0.2 mg/ml $Al^{+3}$) | 0.18 |
| GLA-LSQ | TLR-4 (5 ug GLA), saponin (10 ug QS-21) | Liposome (1 mg/ml phospholipid) | 1.0 |

Each of these adjuvants are comprised of pharmaceutically acceptable components and would be suitable for clinical studies. The emulsion and liposome formulations demonstrated an average particle size of 65-130 nm depending on composition and processing method, whereas the Alum-containing formulations contained microparticles. Nine formulations were prepared by mixing the adjuvants with purified non-tagged LecA protein and mice were immunized subcutaneously. Five mice per group were immunized three times subcutaneously at a 2-week interval with LecA antigen mixed with the corresponding adjuvant. Plasma samples collected a week after the final immunization were diluted 256,000-fold and analyzed for IgG1 and IgG2a production by ELISA. *IgG2a level elicited by GLA 3M-052-liposome adjuvanted LecA was statistically significant in comparison with all other groups except EM014 (GLA-CpG-SE) and 3M-052-emulsion. Titers of plasma IgG subclasses were determined by ELISA (FIG. 2). FIG. 2 shows that the liposome formulation containing a mixture of GLA (a TLR-4 agonist) and 3M-052 (a TLR-7/8 agonist) (designated as GLA-3M-052-LS) showed a balanced IgG response, and was selected for further studies.

Next, the GLA-3M-052-LS' ability to elicit an antigen specific cytokine production indicative of a cell mediated immune response was investigated. Splenocytes were re-stimulated with LecA in vitro and culture supernatants analyzed. GLA 3M-052 liposome adjuvanted containing LecA elicited strong IFN-γ and IL-17 responses, which are markers of protection in the mouse model (FIGS. 3A-3D). Specifically, mice were euthanized a week after third immunization and splenocytes re-stimulated with LecA for 72 h. Production of extracellular IFN-γ, IL-17, IL-2 and IL-4 were detected in the culture supernatant by Luminex and expressed as pg/ml. *=p<0.05; **=p<0.001.

Additionally, PBMCs only from the GLA 3M-052 liposome adjuvanted LecA group showed a moderate but statistically significant intracellular IFN-γ staining.

The compatibility of all-trans retinoic acid (RA) as a co-adjuvant was also tested. Mice in the respective groups received a weekly injection of RA. The RA assisted regimen further increased the levels of IFN-γ and IL-17 (also FIGS. 3A-3D). Both (adjuvant+LecA) and (adjuvant+LecA+RA) groups generated an equivalent IL-2 response; whereas the RA assisted regimen resulted in a slightly higher IL-4 response.

Since a liposome-based vaccine is also suitable for mucosal immunization, a mixed mucosal/parenteral immunization regimen was used for the subsequent experiments to test its ability to generate an antigen specific gut IgA response.

Mucosal IgA Response and its Adherence Inhibitory Potential

Mice were primed with an intranasal immunization, followed by a subcutaneous and an intranasal boost. Mice in the RA assisted groups received a weekly injection of RA. As shown in FIG. 4A, adjuvanted LecA generated a robust mucosal IgA response that was antigen specific. Inclusion of RA helped increase the IgA titer. Adherence of E. histolytica trophozoites to the target cells is an initial and a crucial step in the onset of infection.

To assess if the mucosal IgA was protective in nature, its ability to block adherence of parasites to the CHO cells in vitro was tested. Preincubation of trophozoites with fecal supernatants from the immunized mice significantly reduced their adherence potential (FIG. 4B). Stool suspensions from (adjuvant+LecA) or (adjuvant+LecA+RA) regimens showed comparable adherence inhibitory potential. Thus, adjuvanted LecA elicited a high titer gut IgA response that was protective in vitro.

Figure 5A:
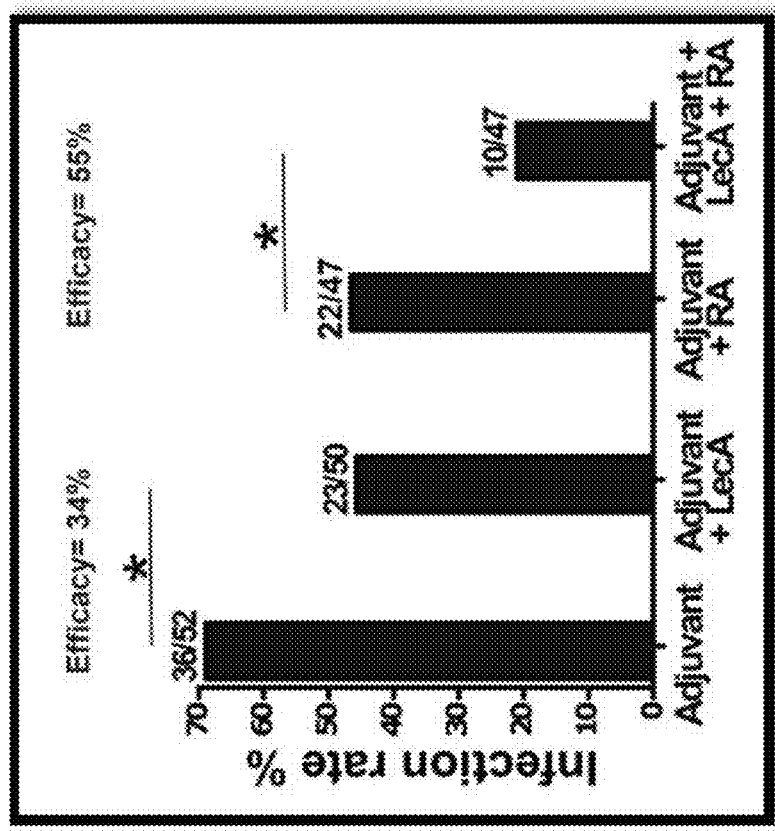
FIGS. 5A-B depict vaccine mediated protection using mouse model of intestinal amebiasis. GLA 3M-052 Liposome adjuvant gave a moderate protection in a cecal challenge trial. Mice immunized using a heterologous regimen were challenged intracecally with *E. histolytica* four weeks post the final immunization. Mice were euthanized a week after the challenge and cecal contents analyzed for (FIG. 5A) antigen load using ELISA and (FIG. 5B) live ameba by culture as a measure of sterile immunity. Number of infected mice from total challenged are indicated above each column. Data from two independent but identical trials were pooled.
Figure 5B:
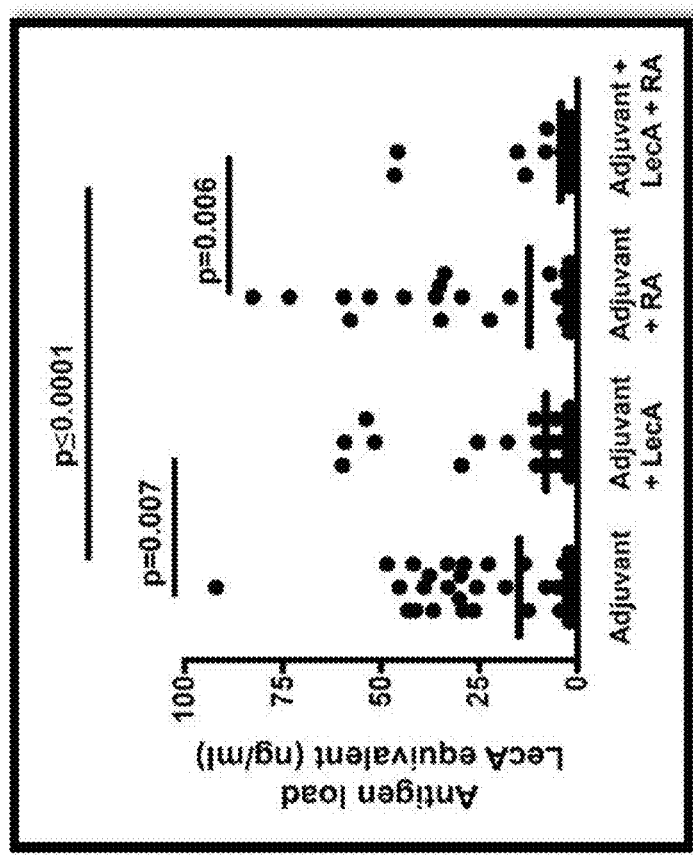

Nanoliposome Formulation Containing Synergistic TLR Agonists has the Potential to Protect Against Intestinal Parasitic Challenge The potential of the GLA 3M-052 liposome adjuvant to protect against E. histolytica challenge using the mouse model of intestinal Amebiasis was tested. Mice from the control and experimental immunized groups were challenged intracecally with a virulent strain of E. histolytica and ceca harvested a week after the challenge to assess the antigen load (FIG. 5A) as well as presence of live parasites (FIG. 5B). Adjuvanted LecA significantly reduced the antigen load compared to control mice and this reduction was even more pronounced with the use of RA as a co-adjuvant. The adjuvant with the current regimen showed a moderate 34% efficacy. However, inclusion of RA in the regimen substantially improved the efficacy to 69.2% (Table 3). The formula used to calculate vaccine efficacy was:

Efficacy=100×(1-(% of vaccinated mice with infection)/(% of sham mice with infection)

Efficacy for adjuvant+LecA group=100×(1−46/69.2) =100×(1−0.66)=34%

TABLE 3

| Vaccine Efficacy | | |
|---|---|---|
| Group | Infection Rate | Efficacy (%) |
| Adjuvant only (Control) | 69.2 | |
| Adjuvant + LecA | 46 | 34 |
| Adjuvant + RA (Control) | 46.8 | |
| Adjuvant + RA + LecA | 21.3 | 69.2 |

These data support that a nanoliposome formulation containing the mixture of synthetic synergistic TLR agonists has the potential to generate an antigen specific protective response and it is compatible with the micronutrient assisted immunization.

Effects of PEG Length

Figure 6:
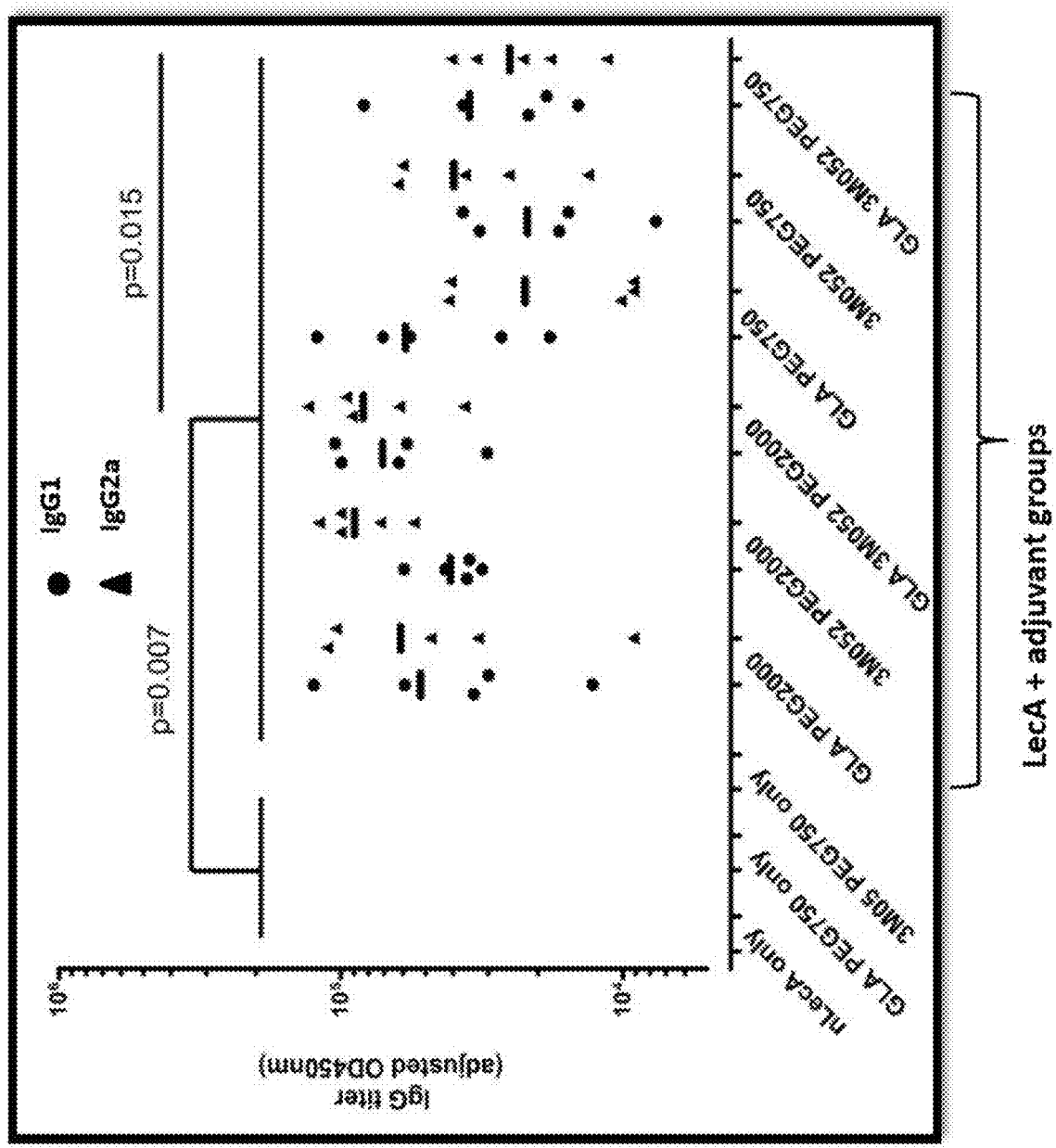
FIG. 6 depicts the plasma IgG response to the indicated formulations.
Figure 7:
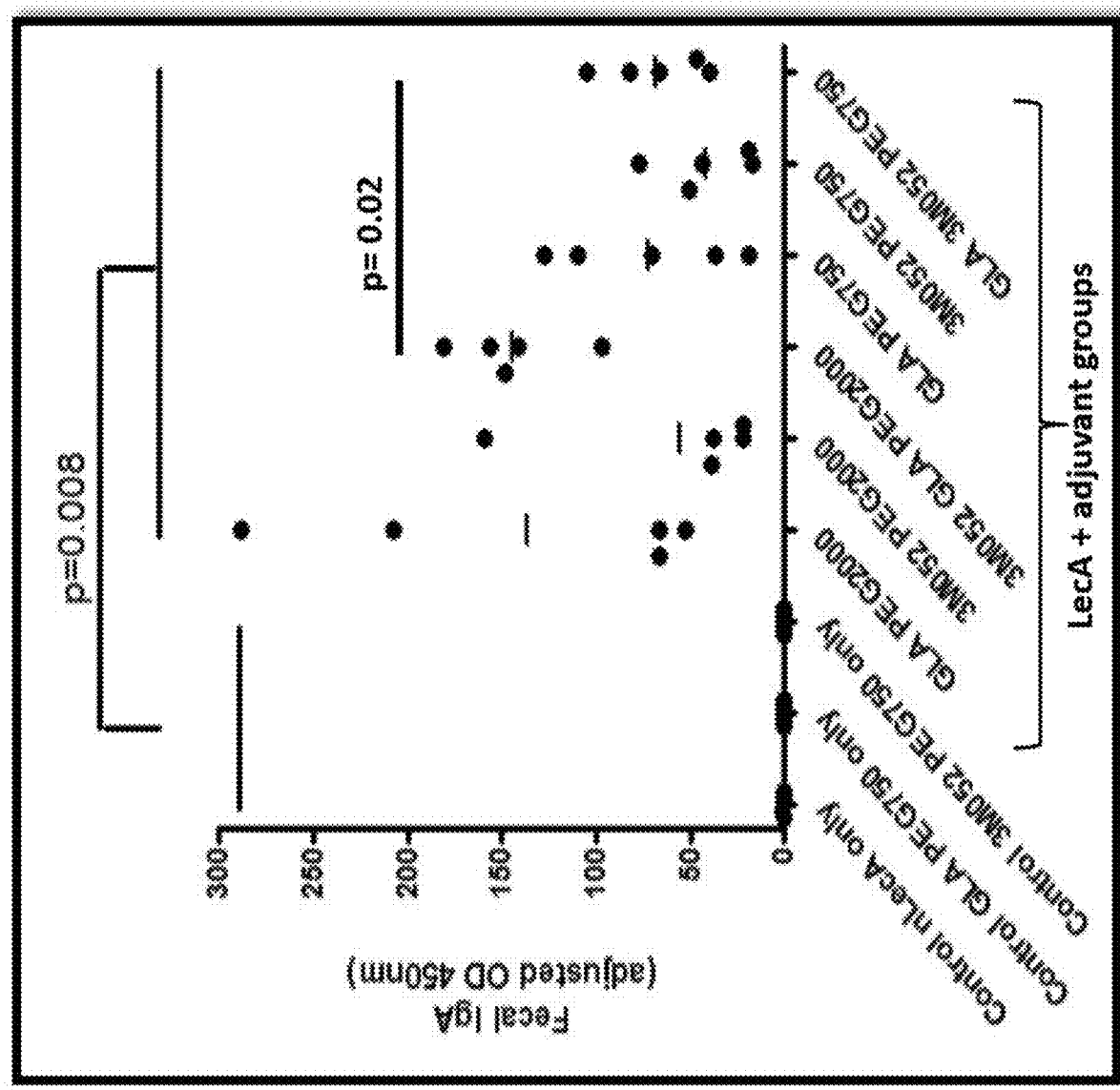
FIG. 7 depicts the fecal IgA response to the indicated formulations. The figure depicts that an increase in PEG length enhances the mucosal IgA response.

FIGS. 6-7 show that higher responses were observed with PEG2000 formulations compared to PEG750. FIG. 6 shows balanced IgG2a and IgG1 titers for the GLA-3M-052 PEG2000+LecA group; there were also higher titers for this group compared to the GLA-3M-052 PEG750+LecA group. In FIG. 7, the effects of PEG length on a fecal mucosal IgA response was investigated. FIG. 7 shows that the fecal IgA response for GLA-3M-052 PEG2000+LecA group was greater than for the GLA-3M-052 PEG750+LecA group. Thus an increase in PEG length in the liposome, enhanced the mucosal IgA response.

Effects of Route of Delivery

Figure 8A:
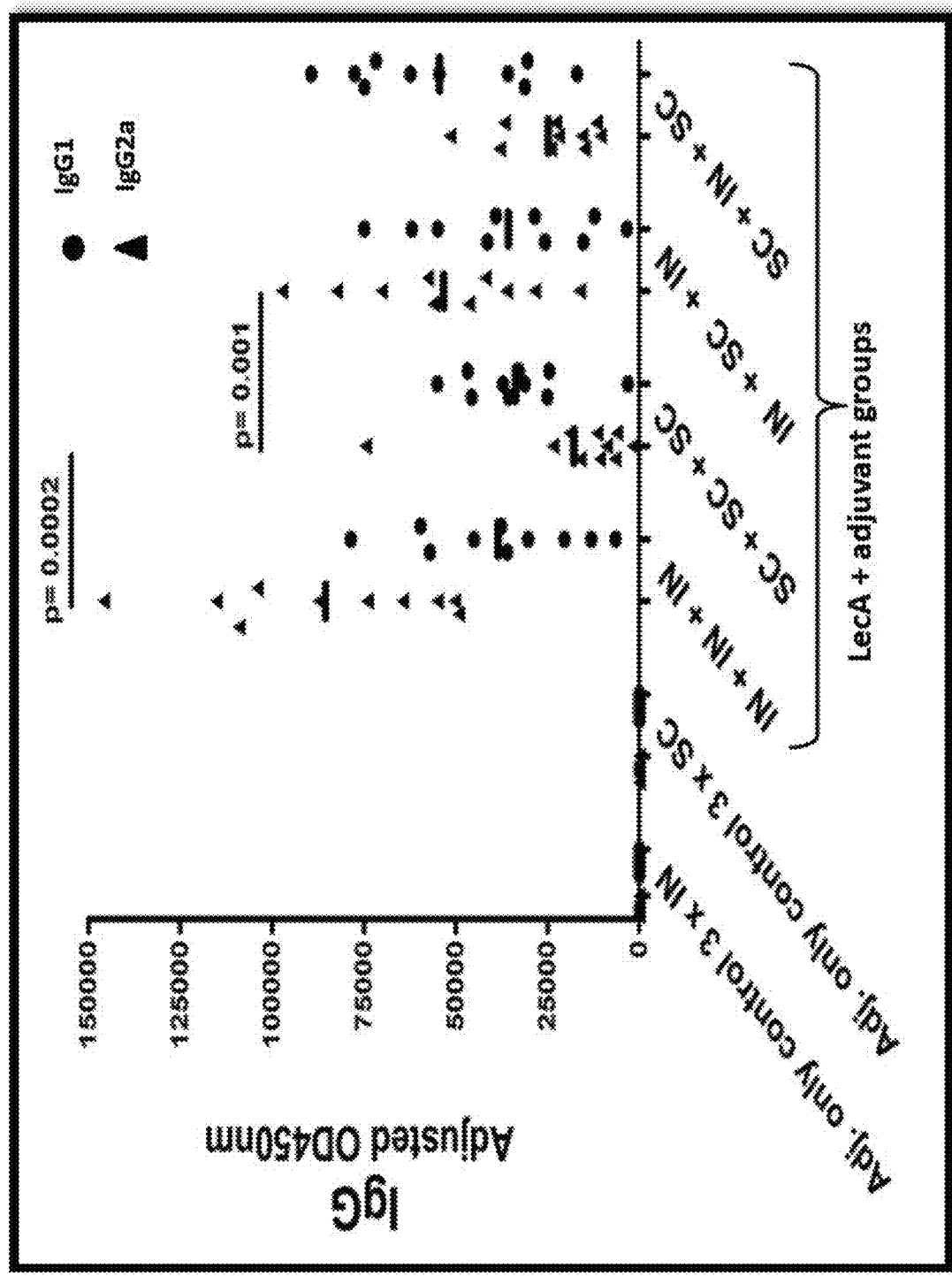
FIGS. 8A-B depict the effects of the route of delivery on immunization with highest IgG2a and IgA titers resulting from IN (intranasal) only regimen. Liposome+adjuvant produced a robust mucosal and systemic Th1 immune response, gut anti-LecA IgA (FIG. 8B).
Figure 8B:
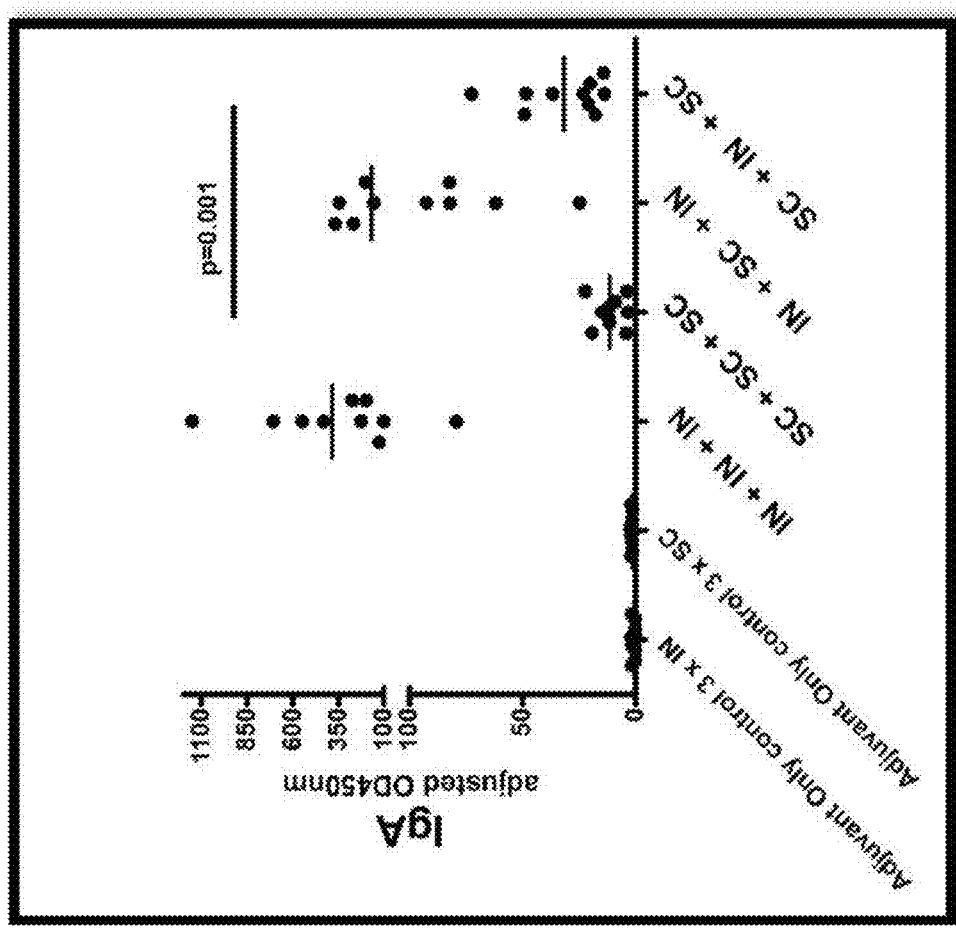

It was investigated whether the route of delivery for the immunization has effects on the immune responses. FIGS. 8A-B depict the effects of the route of delivery on immunization with highest IgG2a and IgA titers resulting from IN (intranasal) only regimen. Liposome+adjuvant produced a robust mucosal and systemic Th1 immune response, gut anti-LecA IgA (16B).

Figure 9A:
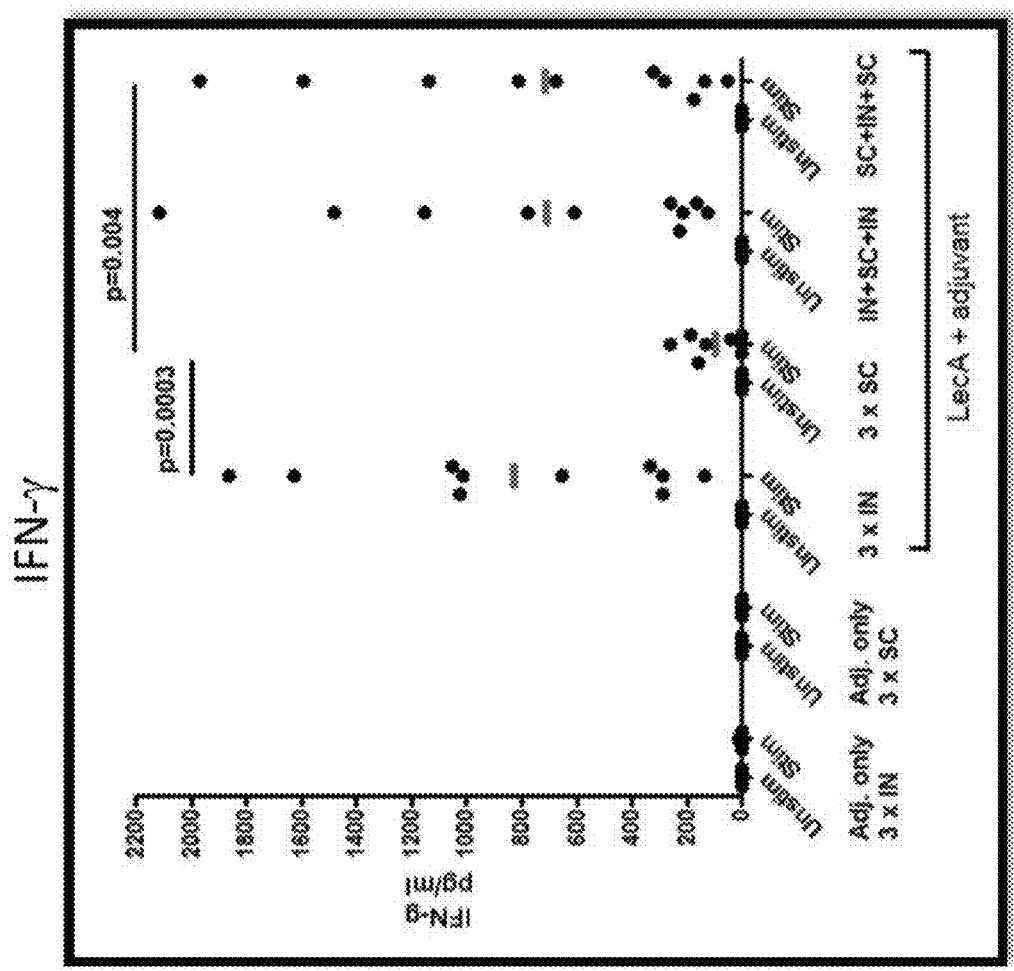
FIGS. 9A-B depict route of delivery effects on immunization. IN only regimen generated equivalent or greater IFN-γ and IL-17 titers compared to other regimens. Liposome+adjuvant produced a robust mucosal and systemic Th1 immune response, IFN-γ (FIG. 9A) and IL17 (FIG. 9B).
Figure 9B:
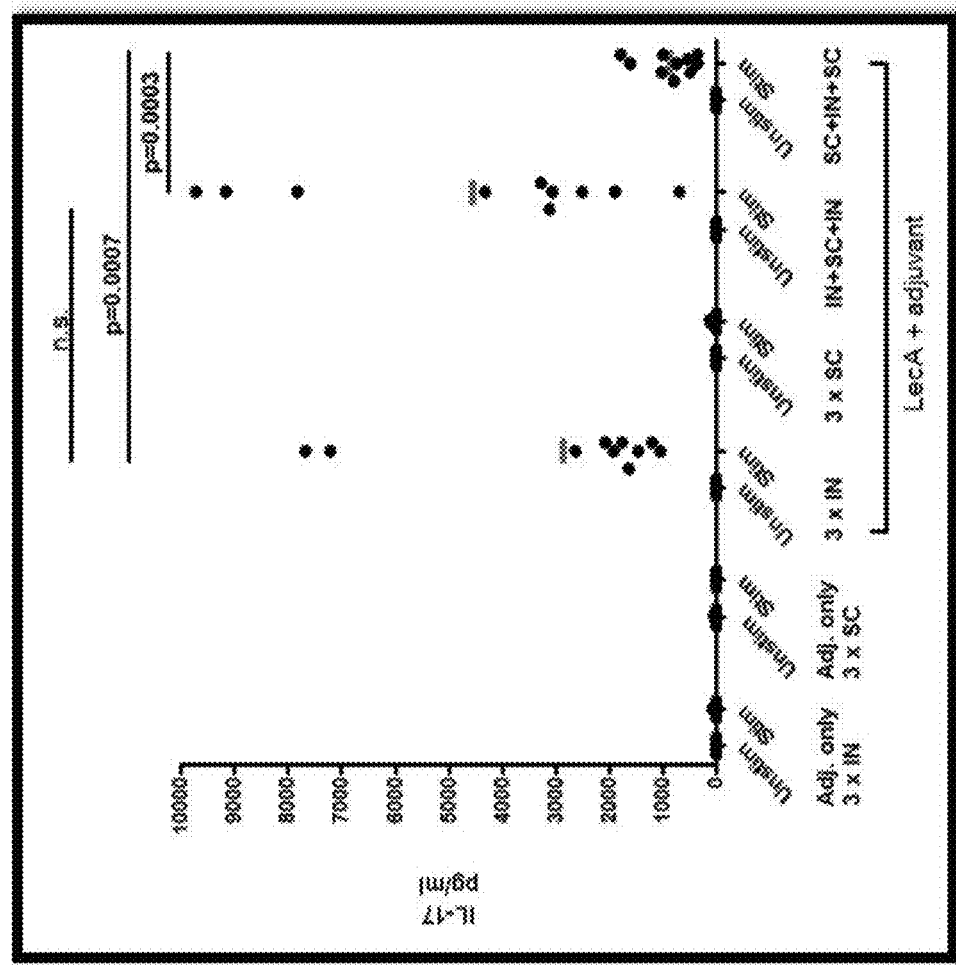

FIGS. 9A-9B further depict routes of delivery. An intranasal only regimen generated equivalent or greater IFN-γ, and IL-17 compared to other regimens. Mucosal only regimen of LecA+liposome+adjuvant produced a robust mucosal and systemic Th1 immune response, IFN-γ (9A-B, Table 4). It was not expected that intranasal delivery would generate an IgA (systemic response) response. This shows that mucosal delivery of GLA and 3M-052 formulated in the liposome with LecA generated systemic immunity. These results demonstrate that a non-mucosal admin of the composition, yields a robust systemic immune response as evidenced by the IgG2a/IgG1 ratios. Surprisingly administration of the composition intranasally at the mucosal surface locally generates not only a mucosal response in the nasal passages, but also the distal intestinal (fecal) mucosal response.

TABLE 4

Intranasal only regimen of LecA + liposome + adjuvant produced a robust mucosal and systemic Th1 immune response

| Regimen | IgG2a/IgG1 Ratio |
|---|---|
| IN + IN + IN | 2.22 |
| SC + SC + SC | 0.53 |
| IN + SC + IN | 1.49 |
| SC + IN + SC | 0.46 |

Discussion of Results

An important outcome of this study was the identification of a nanoliposome adjuvant containing synthetic TLR agonists that was capable of eliciting a systemic as well as mucosal immune response. The liposome based adjuvant system containing TLR4 (GLA) and TLR7/8 (3M-052) agonists generated a balanced humoral and a strong cytokine response. GLA is a synthetic TLR4 ligand that is formulated in lipid-based platforms employed in various Phase 1 and 2 clinical trials. 3M-052 is a synthetic TLR7/8 ligand in advanced preclinical development (Fox et al. Immunopotentiators in Modern Vaccines, $2^{nd}$ ed, in press; Smirnov et al. Vaccine 2011, 29:5434; Zhao et al. J Immunother Cancer 2014, 2:12; Singh et al. J Immunol 2014, 193:4722). A liposomal formulation of GLA and 3M-052 was suitable for a mixed mucosal/parenteral immunization regimen and elicited a strong mucosal IgA response as well. Immunized mice challenged with *E. histolytica* showed a substantial reduction in the antigen load. The GLA 3M-052 nanoliposome formulation was compatible with the use of all trans retinoic acid as a co-adjuvant and such a regimen further increased the protection efficacy and mucosal IgA levels.

Example 2: Formulation and Testing of 3M-052 Adjuvants for Influenza Vaccines

Materials and Methods

Formulation of Materials and Manufacture 3M-052 was synthesized in-house by the 3M Company. R848 was supplied by 3M or purchased from Axxora Life Sciences Inc. (San Diego, CA). Synthetic 1,2-dipalmitoyl-sn-glycero-3-phosphocholine (DPPC), 1,2-dimyristoyl-sn-glycero-3-phosphocholine (DMPC), 1,2-dioleoyl-sn-glycero-3-phosphocholine (DOPC), 1,2-dihexadecanoyl-sn-glycero-3-phospho-(1'-rac-glycerol) (DPPG), 1,2-dipalmitoyl-3-trimethylammonium-propane (DPTAP), 1,2-dipalmitoyl-sn-glycero-3-phosphoethanolamine-N-[methoxy(polyethylene glycol)-750] (DPPE-PEG750), and egg phosphatidylcholine (PC) were purchased from Avanti Polar Lipids Inc (Alabaster, AL) or Lipoid LLC (Newark, NJ). Squalene was obtained from Sigma (St. Louis, MO). Cholesterol, ammonium phosphate monobasic, and ammonium phosphate dibasic were purchased from J. T. Baker (San Francisco, CA). Poloxamer 188 and glycerol were purchased from Spectrum Chemical (Gardena, CA). Phosphate buffered saline 1×(PBS) at pH 7.2 was purchased from Invitrogen (Grand Island, NY).

Small batches (≤20 mL) of PEGylated liposome formulations were manufactured by combining DPPC, cholesterol, and DPPE-PEG750 with various amounts of 3M-052 in organic solvent (chloroform or chloroform/methanol/water mixture). The organic solvent was then evaporated using a Genevac EZ-2. The lipid film was rehydrated in PBS (pH 7.2) or 25 mM ammonium phosphate buffer (pH 5.7) and sonicated in a Crest powersonic CP230D (Trenton, NJ) sonicating water bath at ~60° C. for ~2-3 hrs or until the formulation was translucent with no large visible particles. The same procedure was followed for neutral liposomes (DOPC, cholesterol), anionic liposomes (DPPC, cholesterol, DPPG), and cationic liposomes (DPPC, cholesterol, DPTAP). The liposome component weight ratios were as follows: PEGylated (18:5.5:3, DPPC:chol:DPPE-PEG750), neutral (20:5, DOPC:chol), anionic (18:5:2, DPPC:chol:DPPG), cationic (18:5:2, DPPC:chol:DPTAP). Larger batches (100 mL) of PEGylated liposomes were manufactured as above but with shorter sonication time followed by high shear homogenization (Microfluidizer M110P) for 12 continuous passes at 30,000 psi.

Liposomes containing R848 were prepared by manufacturing a concentrated PEGylated liposome composition as described above except that the liposomes were initially hydrated with 75 mM ammonium sulfate solution. Following sonication at 60° C.~1 h, a PD-10 column (GE Healthcare) was employed to exchange the external buffer of the liposomes to 0.9% saline. The liposomes, now containing saline in their external buffer and ammonium sulfate in their interior, were mixed with a saline solution containing R848 and incubated for 1 h at 60° C. Finally, the liposomes were passed through another PD-10 column to remove unencapsulated R848.

Oil-in-water stable emulsions (SE) were manufactured by dissolving 3M-052 into chloroform with DMPC or egg PC. The chloroform was then removed using a rotary evaporator. Squalene was then added to the dried lipid film and the glass container was placed in a 60° C. sonicating water bath for ~1 h. This mixture is referred to as the oil phase. Alternatively, the oil phase was prepared by dispersing 3M-052 directly into squalene and DMPC (no egg PC or chloroform). An aqueous phase was then added to the oil phase to obtain final concentrations of 25 mM ammonium phosphate buffer, 0.037% (w/w) poloxamer 188, and 1.8% (v/v) glycerol (isotonic agent), 4% v/v squalene, 7.6 mg/ml DMPC or egg PC, and various amounts of 3M-052. Some emulsions also contained 0.02% v/v α-tocopherol. The crude emulsion was created by sonicating the mixture in the 60° C. water bath for another 10-15 minutes. The final emulsion was prepared by processing the crude emulsion through a high shear homogenizer (Microfluidizer M110P) for ~12 continuous passes at 30,000 psi.

Emulsions were prepared with R848 by manufacturing a concentrated emulsion as described above and mixing with dry powder R848 or with a solution of R848 in ammonium phosphate buffer. Emulsions and liposomes were filtered through a 0.2 μm membrane prior to the in vivo experiments described below.

Formulation Characterization

Concentrations of 3M-052 and R848 were estimated by first diluting each formulation 20-fold into a 98% ethanol/2% HCl solution in a cuvette. The samples were analyzed on a Hitachi U-3900H spectrophotometer (Tokyo, Japan) for absorbance at ~322 nm. Particle size was evaluated using a Malvern Instruments (Worcestershire, UK) Zetasizer Nano- S, —ZS, or -APS. Formulations were diluted 100-fold into ultrapure water in a 1.5 ml polystyrene disposable cuvette. For each formulation, three separate cuvettes were prepared. All size measurements were then made three times for each cuvette. Zeta potentials were measured using the Malvern Zetasizer Nano-ZS. For each formulation, 50 µl were combined with 950 µl ultrapure water in a disposable capillary cell (Malvern Instruments, DTS1070). Nine measurements were collected from each prepared sample (one sample per formulation).

Virus Stocks and Vaccines

Vaccine antigens used in this study were all derived from the A/Vietnam/1203/04 (VN1203) influenza virus. Recombinant HA protein (rHA) used in murine immunogenicity and challenge studies was obtained from Protein Sciences Corp. For ferret immunization and challenge studies, a clinical grade split VN1203 vaccine was obtained from Sanofi Pasteur.

Virus stocks for murine and ferret challenge studies were generated by inoculation of 10-day old embryonated chicken eggs with H5N1 stocks as indicated. Clarified allantoic fluid was filtered, and stored at −80° C. until use. Viral titers were determined by plaque assay on MDCK cells (ATCC #CCL-34) using standard assays and as described.

Ferret Whole Blood Stimulation Assay

Whole blood collected from male Fitch ferrets was collected and incubated with TLR agonist compounds including Imiquimod (TLR7), the TLR7/8 agonist CL057 (Invivogen), and the synthetic TLR4 agonist GLA. Following incubation, RNA was collected from both stimulated and saline controls using an RNA whole blood extraction kit (Qiagen). Levels of RNA for TLR7, TLR8, IL-1β, and IL-8 were determined by real time PCR. Expression level changes were graphed as fold change in RNA levels relative to saline stimulated blood samples.

Murine Challenge Studies

For murine challenge studies groups of 6-8 week old female C57Bl/6 mice were immunized with recombinant H5N1 HA protein (VN1203 strain, Protein Sciences Corp.) combined with adjuvant as indicated. All immunizations were via the intra-muscular route in a total volume of 100 μL split evenly between both legs. Twenty one days following immunization, mice were challenged with $1\times10^6$ PFU of A/VN/1203/05 (H5N1 Clade 1). Beginning one day post-challenge, all animals were monitored for weight loss and observed for signs of severe infection. Animals found to have lost >25% of day 0 weight were euthanized.

Ferret Challenge Studies

Male Fitch ferrets (*Mustela putoris fero*, Triple F Farms, Sayre P A) were used for all immunization and challenge studies. Immunization of ferrets was carried out by injection of 250 μL into the quadriceps muscle. All animals received 0.5 μg of a split A/Vietnam/1203/04 H5N1 vaccine (Sanofi Pasteur) sourced from the national pandemic stockpile. Serum samples to determine antibody titers were collected 21 days post-immunization.

Challenge was initiated by instillation of $1\times10^5$-$5\times10^5$ PFU of virus into the lung in a volume of 50 μL (25 μL/nare). Following infection, animals were observed and weighed daily to monitor virus induced morbidity. Any animal losing 25% of pre-challenge weight was euthanized.

Plaque Assay

Virus titers were obtained by plaque assay in Madin-Darby canine kidney (MDCK) cells. Briefly, cells were seeded 24 hours prior to assay initiation into 6-well dishes at $1\times10^6$ cells/well in Dulbecco's modified Eagle's medium (DMEM) supplemented with 10% fetal bovine serum (FBS) and penicillin/streptomycin. At assay initiation, confluent MDCK monolayers were washed three times with DMEM to remove FBS. Serially diluted nasal wash samples were added to monolayers in a 100 μL volume and incubated at 37° C. for 60 minutes. Following incubation, monolayers were overlaid with 2 mL of 0.8% Agarose (SeaKem) in 1×L−15 medium (Lonza). Following 48-72 hours of incubation, plaques were quantified following crystal violet (BD) staining.

Hemagglutination Inhibition (HAI) Assay

Hemagglutinin Inhibition assays were conducted according to the WHO protocol. (52) Formalin inactivated H5N1 antigens were obtained from the National Institute for Biological Standards and Control (NIBSC). All cells were assayed using washed 1% Horse red blood cells (RBC) (Lampire).

Microneutralization Assay

Neutralizing antibody titers were determined using pseudotyped lentivirus particles. Briefly, pseudotype particles are generated by co-transfection of 293T cells with plasmids expressing H5N1 and HA, and 3 lentivirus packaging plasmids; pDR8.74 (55), pRSV-Rev, and HR'-CMV-Luc, which is packaged into the viral particles and encodes a luciferase transgene under the control of the CMV immediately early promoter. Virus stocks were titered in black flat-bottom 96 well plates (Corning) seeded 24 hour prior with $5\times10^3$ MDCK cells/well in Dulbecco's modified Eagle's medium (DMEM)+10% fetal bovine serum (FBS). Prior to virus titration, cells were washed 3 times with 200 μL DMEM to remove DMEM, and overlaid with serially diluted virus stocks. Following 72 hour incubation to allow transgene expression, levels of luciferase in transduced cells were determined using BrightGlo luciferase (Promega), according to manufacturer's instructions.

For neutralization analysis, serially diluted post-immunization serum was mixed at a 1:1 ratio with diluted virus stocks containing $1\times10^4$ relative luciferase units (RLU). Virus serum mixtures were incubated at 37° C. for 1 hour, and added to plates containing washed MDCK cells as above. Neutralization titers were determined following assessment of luciferase expression level in all transduced cells. $IC_{90}$ antibody titer is defined as the highest dilution of serum observed to reduce luciferase levels by 10-fold relative to vector transduced control cells.

HA Arrays

HA Arrays containing influenza HA proteins have been previously described (56). The arrays used in this study are second generation, and contain 278 HA proteins from a variety of influenza strains (Sinobiological). For post-vaccination immune analysis, arrays were initially blocked with PBS+1% Fetal Bovine Serum+0.1% Tween-20, washed three times with Protein Array Wash Buffer (ArrayIt), and incubated with 300 μL of a 1:100 dilution of post-immunization mouse serum for 1 hour with shaking. Following primary incubation, arrays were washed 5 times with wash buffer, and incubated with fluorophore conjugated secondary antibodies for IgG2c (Jackson Immunoresearch, Part #: 115-495-208) and IgG1 (Life Technologies, Part #: A21123) at a 1:2000 dilution. Following a 30 minute incubation at room temperature, arrays were rinsed with Rinse Buffer (Arrayit), and analyzed using a Molecular Dynamics 400B array scanner. Post-acquisition analysis was done using Tableau data analysis software.

ELISA

HA-specific endpoint titers for IgG, IgG1 and IgG2c were determined seven days and twenty-one days post immunization. High binding polystyrene 384 well plates were coated with recombinant VN1203 HA (Protein Sciences Corp.) (2 µg/ml) in 0.1 M bicarbonate coating buffer for 2.5 hours at room temperature. Plates were washed three times with 0.1% PBS-Tween 20 pre and post a two hour blocking incubation with 0.05% PBS-Tween 20+1% BSA at room temperature. Mouse sera was serially diluted in 0.05% PBS-Tween 20+0.1% BSA using the Nanonscreen NSX-1536 and incubated overnight at 4° C. and washed five times. Plates were incubated for 1 hour on the shaker with anti-mouse IgGT, IgG1 or IgG2c-HRP (Southern Biotechnologies). Following five washes, plates were developed on the Nanoscreen robot using SureBlue tetramethylbenzidine substrate (Kirkegaard & Perry Laboratories). The enzymatic reaction was stopped with 1 N H2SO4 using the Multipette Sagian robot. Plates were read at 450-570 nm using the Synergy ELISA plate reader (Biotek) and Gen5 software.

Intracellular Cytokine Staining

In order to quantify vaccine specific T cell responses, splenocytes were isolated from five mice per group following vaccination. Red blood cells were lysed using Red Blood Cell Lysis Buffer (eBioscience) and resuspended in cRPMI 1640(10% FBS, 1% Penicillin/Streptomycin; 0.1% 2-Mercaptoethanol). Cells were plated at $10^7$ cells/well in 96-well plates and were stimulated for 2 hours with media or rHA Antigen (10 µg/mL) at 37° C. 1:50 GolgiPlug (BD Biosciences) was added and the cells were incubated for an additional 8 hours at 37° C. Cells were washed and surface stained with fluorochrome labeled antibodies at 1:100 in 1% BSA-PBS to CD4 (clone RM4-5), CD8 (clone 53-6. 7), CD44 (clone IM7) and B220 (RA3-6B2) (BioLegend and eBioscience) in the presence of anti-CD16/32 (clone 93) for 15 minutes in the dark at room temperature. Cells were fixed and permeabilized with Cytofix/Cytoperm (BD Biosciences) for 30 minutes at room temperature in the dark. Cells were washed with Perm/Wash (BD Biosciences) and stained with fluorochrome labeled antibodies to detect intracellular cytokines as follows: IFN-γ (clone XMG-1.2), IL-2 (JES6-5H4), TNF (MP6-XT22), IL-5 (clone: TRFK5) and IL-10 (clone: JES5-16E3) (BioLegend and eBioscience) Staining was carried out for 15 minutes at room temperature in the dark. Cells were washed, resuspended in 1% BSA-PBS and filtered using a 30-40 µm PP/PE 96 filter plate (Pall Corp). Up to $10^6$ events were collected on a four laser LSR Fortessa flow cytometer (BD Biosciences). Data were analyzed with FlowJo (Treestar).

Results

DPPC-based liposomes modified with anionic, cationic, or PEGylated phospholipids, and a neutral DOPC-based liposome were manufactured by the thin film technique followed by sonication. Liposomes were manufactured at a high 3M-052 concentration of 1 mg/ml in order to highlight any tendency for incompatibility with the various liposome compositions. After two separate batches for each liposome, the PEGylated liposome and the DOPC liposome demonstrated translucent appearance and the smallest particle size and polydispersity following sonication (Table 5).

TABLE 5

Formulation properties of liposome and emulsion formulations of 3M-052

| Formulation Type* | Composition | Batch #1 Size (Z-Ave, nm), PdI, and Appearance | Batch #2 Size (Z-ave, nm), PdI, and Appearance |
|---|---|---|---|
| Anionic Liposome | DPPC, DPPG, cholesterol | 155.8, 0.398, opaque/milky | 155.9, 0.716, opaque/milky |
| Cationic Liposome | DPPC, DPTAP, cholesterol | 145.6, 0.539, translucent | 210.7, 0.560, translucent |
| PEGylated Liposome | DPPC, DPPE-PEG750, cholesterol | 143.1, 0.284, translucent | 90.9, 0.185, translucent |
| Neutral Liposome | DOPC, cholesterol | 123.5, 0.354, translucent | 44.0, 0.146, translucent |
| Oil-in-water emulsion | squalene, DMPC or egg PC, poloxamer 188, glycerol | 91.2, 0.056, opaque/milky | 83.9, 0.048, opaque/milky |

*Liposomes and emulsions were manufactured to contain 1 mg/ml 3M-052 or 0.04 mg/ml 3M-052, respectively The PEGylated liposome was selected for further stability and in vivo evaluation. The PEGylated liposomes were negatively charged (Table 6), most likely due to the anionic phosphate group of DPPE-PEG750.

TABLE 6

Zeta potentials of representative liposome and emulsion formulations containing 3M-052

| Formulation | Estimated 3M-052 Concentration (mg/ml)* | Zeta Potential (mV) |
|---|---|---|
| PEGylated Liposome | — | −37.1 ± 4.8 |
| PEGylated Liposome | 0.04 | −27.1 ± 1.1 |
| Oil-in-water emulsion | — | −4.2 ± 0.6 |
| Oil-in-water emulsion | 0.04 | −8.6 ± 1.0 |

*3M-052 content was not measured for these batches but was estimated to be 0.04 mg/ml based on subsequent batches manufactured using the same process.

The liposomes demonstrated little or no change in particle size for at least 6 months at 5° C. (FIGS. 10A-10B). In general, no loss of 3M-052 during manufacture was evident. Squalene-based oil-in-water emulsion (SE) formulations of 3M-052 were manufactured by microfluidization, generating <100 nm size droplets with low polydispersity and long-term particle size stability (FIGS. 10A-10B). Emulsion zeta potential values were slightly negative (Table 6). Surprisingly, emulsions manufactured with egg PC instead of DPMC resulted in higher recovery of 3M-052 after processing. Moreover, adding an initial mixing step of combining 3M-052 with egg PC in chloroform further increased recovery of 3M-052 compared to sonication of the dry powder into squalene/egg PC without chloroform. Thus, changes in emulsion composition and processing procedure had significant effects on 3M-052 incorporation in the final formulation. See Table 7 below

TABLE 7

3M-052 recovery following emulsion manufacture

| Emulsifier | Pre-mixed in CHCl$_3$ (Y/N) | Target 3M-052 Concentration (mg/ml) | Measured 3M-052 Concentration Pre-filtration (mg/ml) | Measured 3M-052 Concentration Post-Filtration (mg/ml) | 3M-052 Recovery |
|---|---|---|---|---|---|
| DMPC | N | 0.12 | | 0.01 | 8% |
| DMPC | N | 0.12 | | <0.01 | <8% |
| DMPC | N | 0.04 | | 0.01 | 25% |
| DMPC | N | 0.04 | | <0.01 | <25% |
| DMPC | Y | 0.12 | 0.09 | 0.04 | 33% |
| Egg PC | N | 0.12 | 0.08 | 0.05 | 42% |
| Egg PC | Y | 0.12 | 0.12 | 0.12 | 100% |
| Egg PC | Y | 0.08 | 0.08 | 0.08 | 100% |
| Egg PC | Y | 0.8 | 0.76 | 0.32 | 40% |

Formulated 3M-052 Combined with H5N1 HA Protects Mice From Lethal H5N1 Challenge Following A Single Immunization Following demonstration of the stability of 3M-052 adjuvant formulations (FIGS. 10A and B), the ability of this TLR agonist to enhance HA specific vaccine responses was investigated. 3M-052 formulated in either PEGylated liposomes or in a squalene oil-in-water emulsion (SE) was admixed with a recombinant influenza HA H5N1 protein (A/Vietnam/1203/04 strain [VN1203], Protein Sciences Corp., Meridien CT) and used to immunize groups of C57Bl/6 mice (N=20/group) via the intramuscular route. Twenty one days following a single immunization, all mice were challenged intranasally with 1000 LD50 of VN1203. Ten animals were followed for 14 days to determine virus induced morbidity, measured by weight loss, as well as mortality. In a liposomal adjuvant formulation, 3M-052 prevented virus induced morbidity; 100% of animals receiving rH5+3M-052-Liposome survived compared with 50% of animals receiving rH5 or rH5 combined with liposomes alone (FIG. 11A). Mice immunized with rH5+3M-052-liposomes showed no weight loss, whereas animals receiving rH5 with or without liposomes lost weight for 11 days following challenge (FIG. 11B). Animals receiving emulsion based formulations showed consistent survival both with and without 3M-052 (FIG. 11A), consistent with the known efficacy of emulsions as influenza adjuvants. However, animals receiving emulsions combined with TLR 7/8 agonists showed reduced weight loss over the acute infection period compared with animals receiving rH5+SE (FIG. 11C).

Figure 11D:
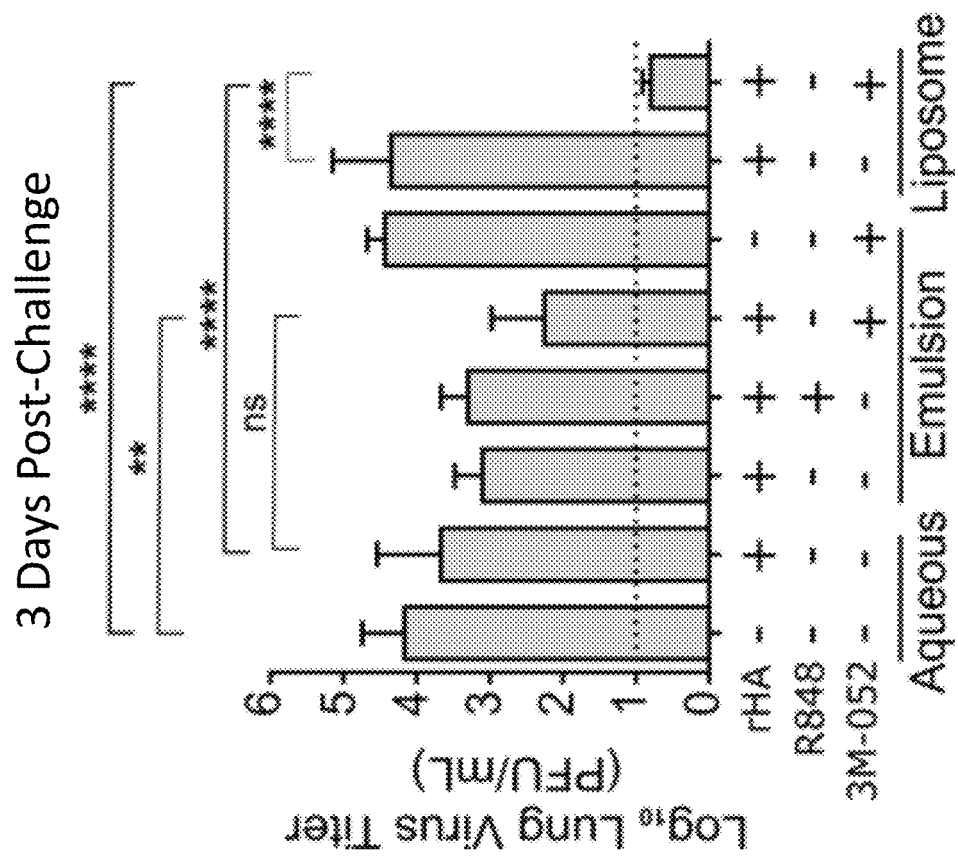
Figure 11E:
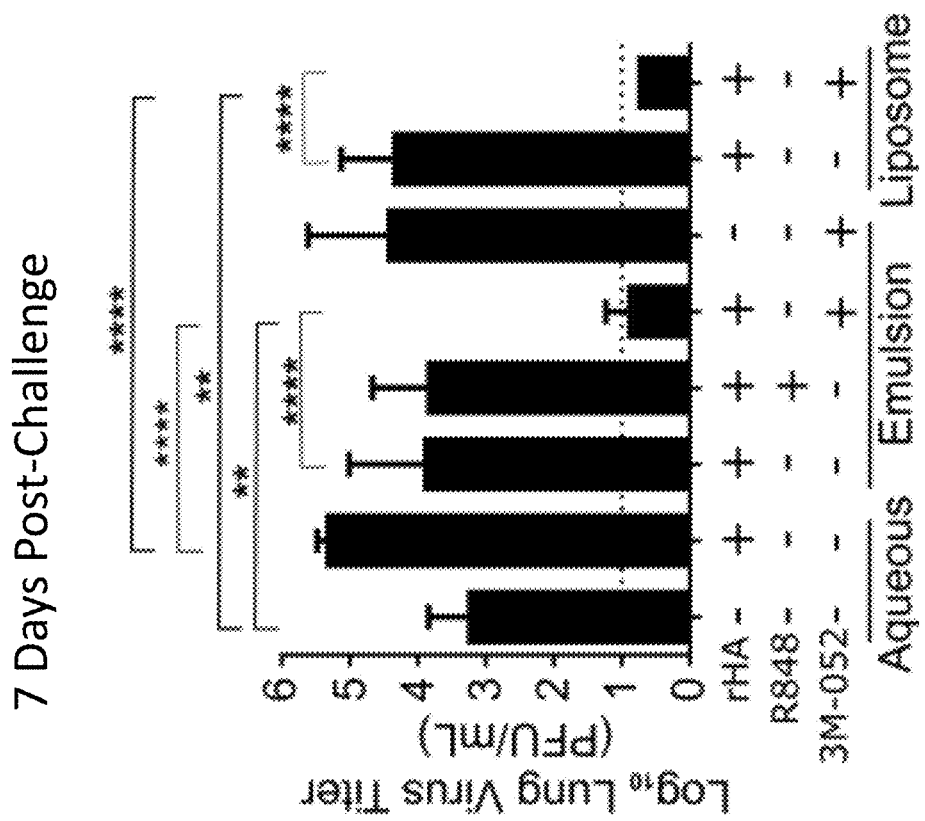
Figures 11F, 11G:
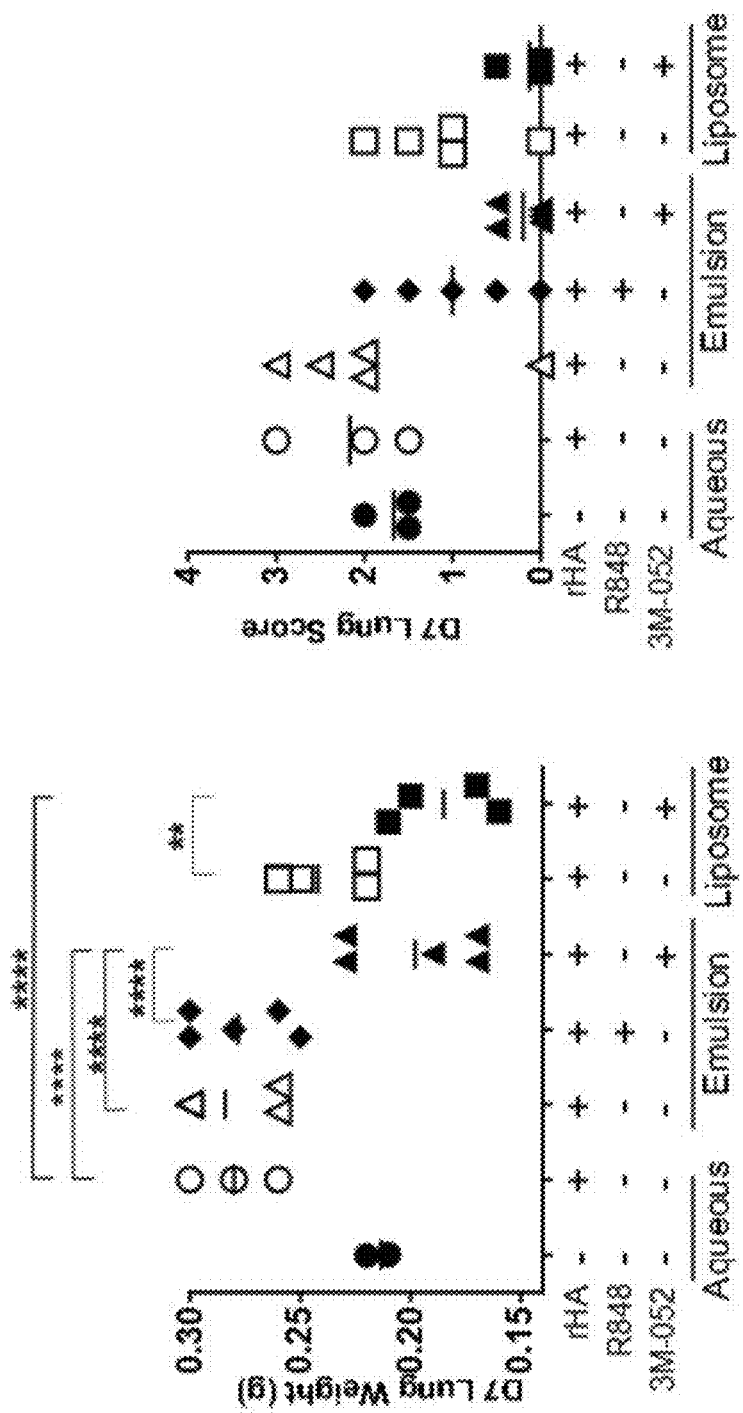
Figure 11H:
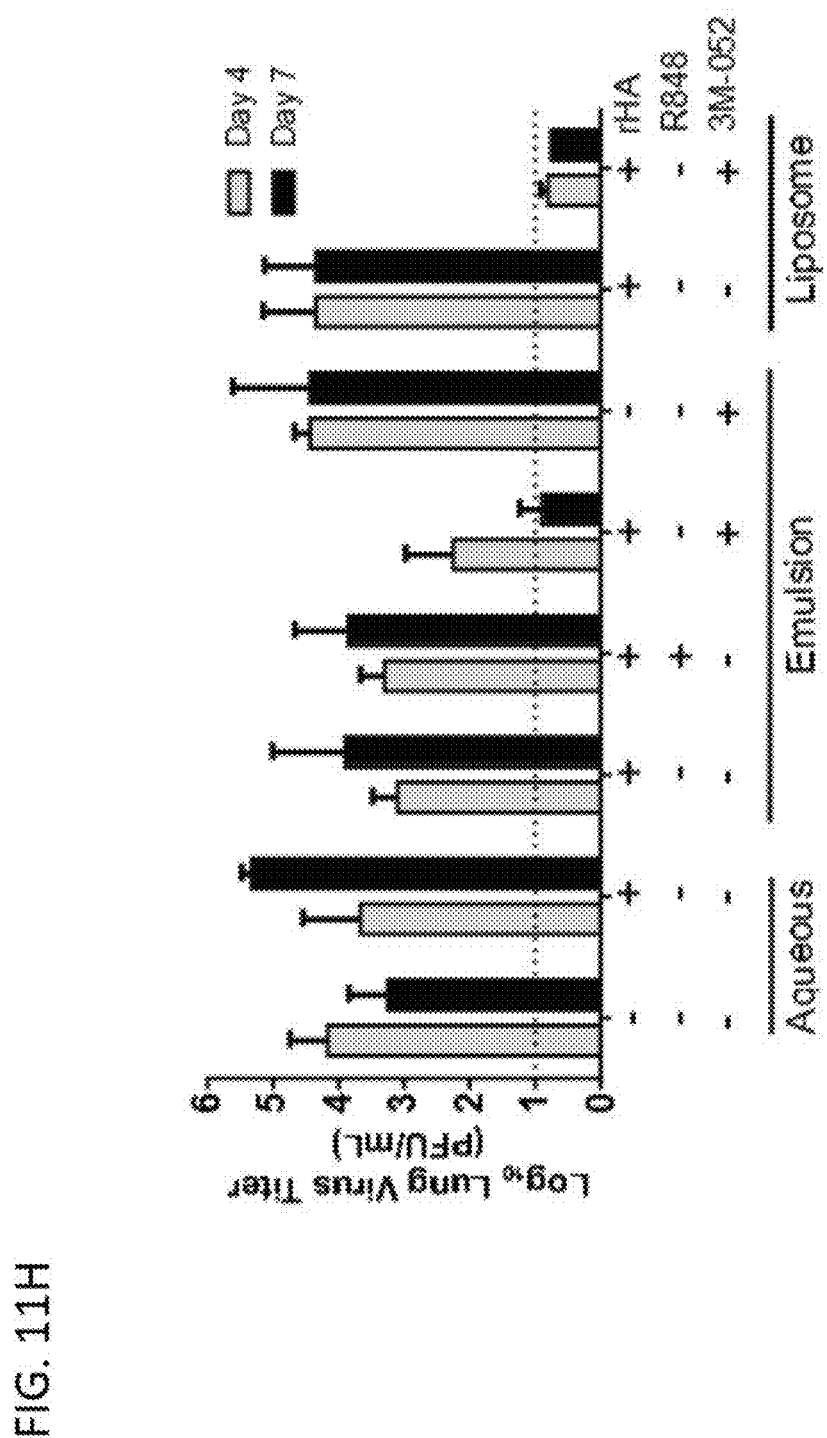

In addition to the animals monitored for survival, 5 animals/groups were euthanized at 4 and 7 days post-challenge to measure/observe influenza induced pathology in the lung and to determine lung viral titers. At 4 days post-challenge, animals immunized with rH5+3M-052 adjuvant formulations had significantly reduced lung viral titers relative to non-immunized controls. Animals immunized with rH5+3M-052-liposomes had no detectable virus titer at this timepoint (FIG. 11D). At day 7, animals receiving 3M-052 based adjuvant formulations had minimal viral titers relative to rH5 alone. For both liposomes and SE based formulations, addition of 3M-052 resulted in significantly reduced titer relative to the same formulation without TLR (FIG. 11E). In addition to reduced viral titers, animals immunized with rH5+3M-052 adjuvant formulations showed significantly lower lung weight (FIG. 11F) and reduced lung pathology scores (FIG. 11G). Taken together, these results demonstrate the ability of 3M-052 to protect mice even from clinical sequelae of lethal avian influenza challenge. FIG. 11H shows the lung virus titer.

3M-052 Adjuvant Formulations Induce a Th1 CD4 T-Cell Response in Mice

To investigate correlates of protection for the 3M-052-containing adjuvant formulations, CD4 T-cell responses induced following immunization with rH5 in combination with adjuvants was examined. Following a single immunization, cytokine production from CD4+ T cells was examined. Low, but detectable, levels of Th1 cytokine positive cells (IFNγ/TNFα/IL-2) could be demonstrated in animals immunized with 3M-052 adjuvant formulations (FIGS. 12A-C). Canonical Th1 CD+ T cells could be observed in all adjuvant formulations shown to be protective in animals. Consistent with previous work, these data demonstrate the ability of 3M-052 to induce a Th1 biased cellular response in mice following vaccination with low levels of antigen.

3M-052 Adjuvant Formulations Induce a Broadened Cross Subtype Antibody Response to H5N1 HA An induction of Th1 CD4 T cells (IFNγ$^+$TNFa$^+$IL-2$^+$) following immunization with formulated 3M-052 adjuvants was observed (FIG. 12). Using a second generation high density HA protein array, the ability of 3M-052 to broaden the antibody response induced by a Clade 1 rH5 antigen was investigated. The HA array used in this study contains 278 individual HA proteins, including at least one representative from HA subtypes 1-16. The ability of both IgG1 and IgG2c antibodies to bind to HA proteins from different subtypes was investigated. Addition of adjuvants increased the level of antibody induced following a boost immunization. The SE and Liposome adjuvants showed increased binding to H5 subtype proteins, and were predominated by IgG1 responses. Addition of 3M-052 to either formulation resulted in significant broadening of the antibody response, with binding to a wide range of HA subtypes, as well induction of cross-reactive IgG2c antibodies. (Data not shown)

Examination of the H5 strains on the array clearly demonstrated a cross-clade binding response following immunization with 3M-052 formulations. Both 3M-052-Liposome and 3M-052-SE immunized animals showed increased levels of IgG2c antibody that bound to proteins from multiple H5N1 virus clades. In contrast IgG1 levels were not dependent on the presence of 3M-052. In order to verify the findings from the HA arrays, the antibody endpoint titer in post-immunization mouse serum by ELISA using VN1203 HA as a coating antigen was determined. The results observed by serum ELISA mirrored those observed on the HA array. (Data not shown)

TLR 7/8 Agonists Enhance Receptor and Cytokine mRNA in Ferret Whole Blood

In order to confirm that imidazoquinolines are capable of stimulating cognate TLR receptors in ferrets, a whole blood stimulation assay was carried out. Whole blood from male Fitch ferrets was collected and stimulated with either imidazoquinolines or with the synthetic TLR4 agonist Glucopyranosyl Lipid A (GLA). The ability of agonist molecules to stimulate both cytokines and TLR receptor mRNA was examined using real time PCR. Stimulation of whole blood with both 100 μM R848 (in other species a known TLR7/8 agonist, 3M) and 100 μM CL075 (in other species a known TLR8 Agonist, Invivogen) resulted in significant increases in IL-1B, IL-8, TLR7 and TLR8 mRNA. This result demonstrates the ability of imidazoquinolines to stimulate ferret receptors, and suggests that ferrets have both active TLR7 and TLR8 which may play a role in this model of influenza disease.

Figure 13A:
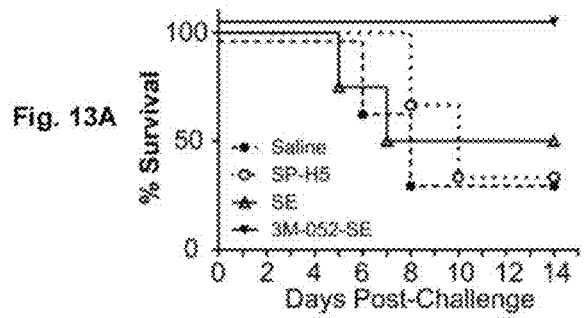
FIGS. 13A-H depicts protection of ferrets from homologous H5N1 challenge following a single immunization. Male Fitch ferrets were immunized once with a split H5N1 vaccine (H5N1, Sanofi Pasteur) in combination with formulated 3M-052 adjuvants, and challenged 21 days post immunization with $10^6$ PFU of A/VN/1203. Animals were monitored for up to 14 days for survival (FIGS. A,E) weight loss (FIGS. B,F) and clinical scores (FIGS. C,G). In addition, nasal washes were collected to assess virus titer (FIGS. D,H). Both 3M-052-SE and 3M-052-Liposomal adjuvant formulations show potent single shot protection in this model, characterized by more rapid viral clearance from nasal washes, reduced weight loss and clinical scores, and 100% survival.
Figure 13E:
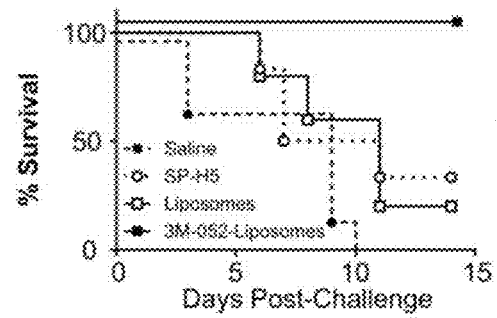
Figure 13B:
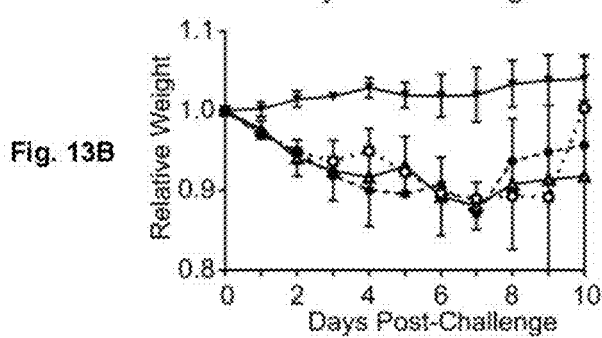
Figure 13F:
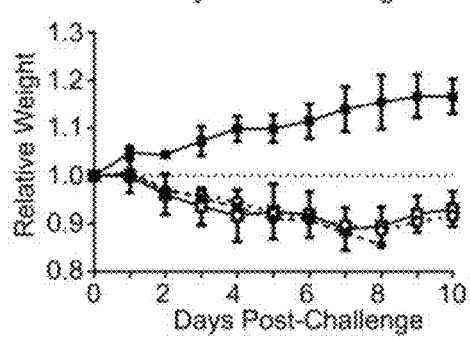
Figure 13C:
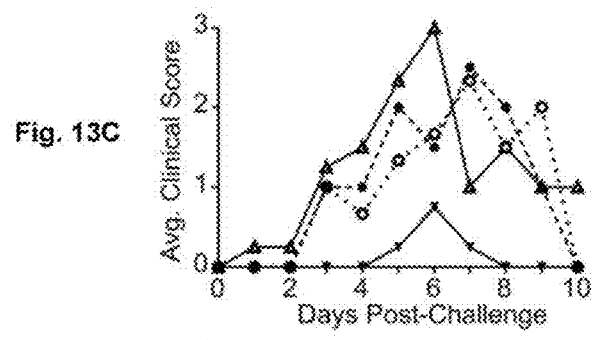
Figure 13G:
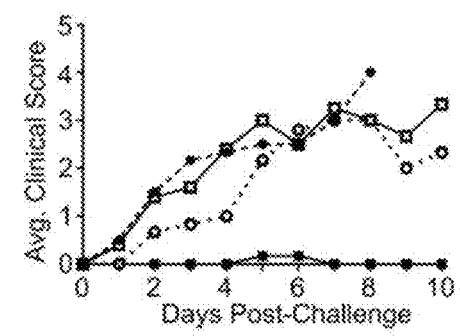
Figure 13D:
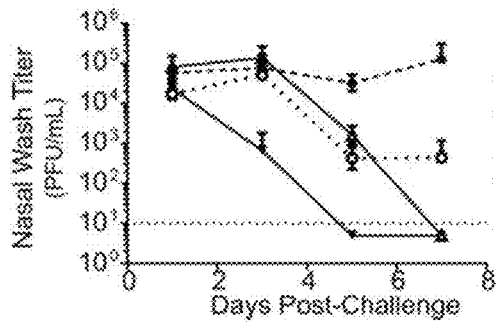
Figure 13H:
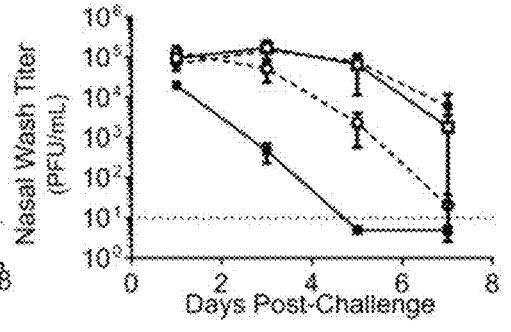

Formulated 3M-052 Adjuvants Enhance (Combined with H5N1 Antigens) Protection Against H5N1 Challenge in Ferrets After a Single Immunization Given promising results in mice, and verification that imidazoquinolines could stimulate ferret TLR, the ability of 3M-052 containing adjuvants to protect ferrets form lethal H5N1 challenge following a single immunization was examined. For these studies, neutral liposome and SE adjuvants with and without 3M-052 were combined with an H5N1 split virus vaccine (Sanofi) derived from VN1203 (SP-H5). This antigen was chosen because it is currently included in the national pandemic stockpile for the United States, and has been tested clinically in previous studies. Briefly, following a dose ranging study with H5N1 antigen alone (Data not shown), groups of 4-6 ferrets were immunized via the intramuscular route with 0.5 µg of SP-H5 admixed with adjuvants as indicated (FIG. 13). Twenty-one days post-immunization, ferrets were challenged intranasally with $10^6$ PFU of A/VN/1203/04, and followed for 14 days for weight loss, clinical scores, and survival. In addition, nasal washes were collected on alternate days beginning one days post-challenge. In one study, 3M-052/SE completely protected animals from challenge, compared with animals immunized with SP-H5+SE (FIG. 13A). 3M-052/SE also reduced virus-induced morbidity compared to SE alone; animals immunized with SP-H5+3M-052/SE lost no weight following challenge (FIG. 13B), and had only minimal clinical scores throughout the infection (FIG. 13C). Similar results were observed in a second experiment following immunization of animals with liposomal adjuvant formulations. 3M-052-Liposomes protected 100% of animals from challenge (FIG. 13E). Similar to SE based formulations, animals immunized with SP-H5+3M-052 liposomes lost no weight (FIG. 13F), and had negligible clinical scores (FIG. 13G). Perhaps most importantly, examination of lung viral titers shows that in both SE and Liposomal formulations, 3M-052 is capable of reducing virus shedding in nasal washes; animals immunized with 3M-052/SE (FIG. 13D) or 3M-052/Liposomes (FIG. 13H), showed significant reductions as soon as 3 days post-challenge compared to other adjuvants or control animals. In both cases, virus was cleared to undetectable levels by day 5 in all animals receiving 3M-052 adjuvants.

3M-052 Adjuvant Formulations Induce a Cross-Clade Neutralizing Antibody Response in Ferrets Based on the broad HA-specific antibody response that observed in mice and the robust protection we observed against homologous virus in ferrets, the neutralizing antibody titers induced following immunization with different adjuvant formulations using a H5N1 HA pseudotyped lentivirus vector packaging a Luciferase transgene was directly examined. Briefly, serially diluted serum samples were incubated with lentiviral particles containing H5N1 HA and NA proteins on their surface. Serum-virus mixtures were incubated on confluent monolayers of MDCK cells. Following incubation to allow expression of the luciferase transgene packaged into the virus, neutralization potential of serum samples was determined by quantification of luciferase gene expression. Consistent with increased survival observed in these studies, 3M-052/SE and 3M-052/Liposomes adjuvants increased $IC_{90}$ neutralization titers in serum 21 days following a single injection. (FIGS. 14A, D). In addition, both formulations significantly increased neutralization titers to Clade 2 viruses; increased $IC_{90}$ titers to A/Indo/5/05 [Clade 2.1] and A/Whooper swan/Mongolia/244/05 [Clade 2.2] were observed (FIGS. 14B-F). This finding is consistent with the ability of formulated 3M-052 to induce broad functional neutralizing antibody titers to drifted influenza strains.

3M-052-SE Induces a Cross-Clade Protective Response

Figures 15A, 15B:
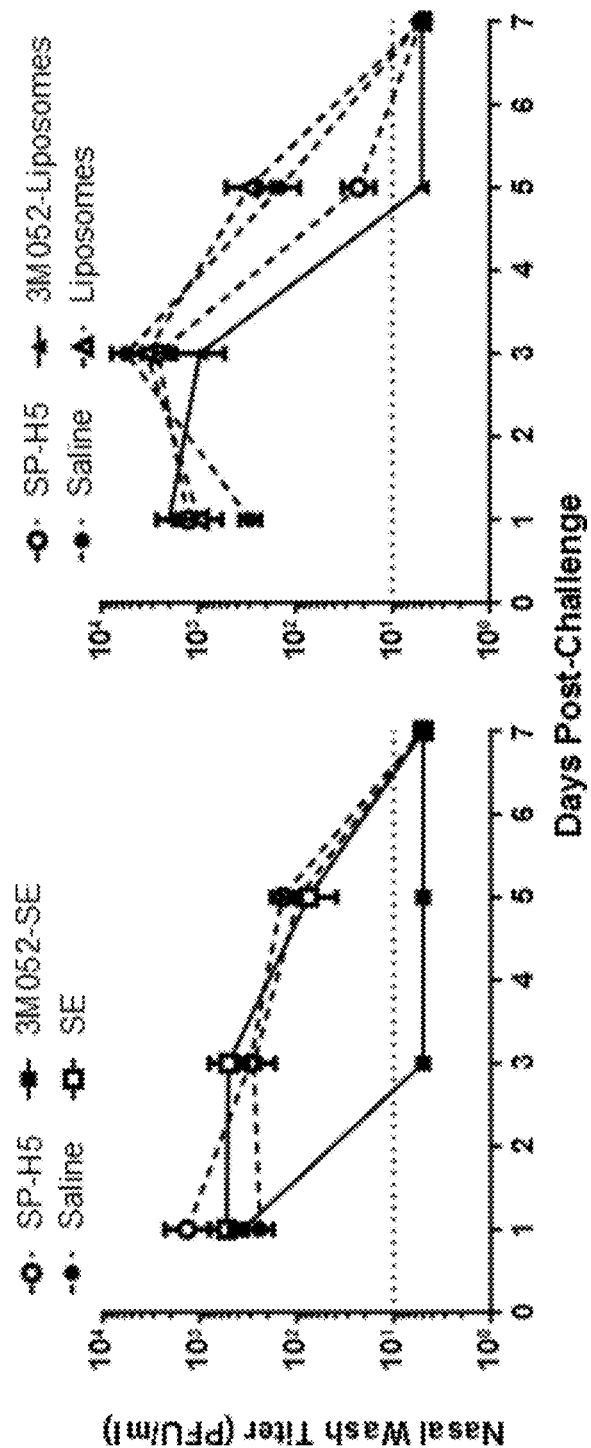
FIGS. 15A-B depict the protection of ferrets from heterologous H5N1 challenge following a single immunization. Male Fitch ferrets were immunized once with a split H5N1 vaccine (H5N1, Sanofi Pasteur) in combination with formulated 3M-052 adjuvants, and challenged 21 days post immunization with $10^6$ PFU of A/Whooper Swan/Mongolia/244/05. Nasal washes were collected to assess virus titer. 3M-052-SE adjuvants induced a more rapid clearance of virus, with undetectable titers at day 5. 3M-052-Liposomal adjuvant formulations show titer through day 3, with clearance by day 5.

Given the neutralizing titers that were observed to A/Whooper swan/Mongolia/244/05 following immunization with VN1203 antigens, the ability of formulated 3M-052 to reduce virus replication in the lung following vaccination with VN1203 antigen was investigated. As in the previous studies, ferrets were immunized once with SP-H5 combined with formulated 3M-052, and challenged 21 days later with $5 \times 10^5$ PFU of virus. Animals receiving 3M-052/liposomes showed a modest decrease in virus shedding over time; animals receiving 3M-052/Liposomes had no detectable virus at 5 days post-challenge, while other animals receiving liposomes or antigen alone had detectable virus at this time (FIG. 15B). In contrast, animals receiving 3M-052-SE rapidly cleared the virus, with no detectable plaques from 3 days post challenge, while those receiving SP-H5+SE showed detectable virus titers through day 5 (FIG. 15A).

Discussion of Results

The results presented here demonstrate protection in mice and ferrets following high dose (1000 $LD_{50}$) challenge with H5N1 viruses when animals are immunized with the formulated TLR7/8 agonist 3M-052. 3M-052 is incorporated into either formulation, and these formulations are stable for extended periods. A novel PEGylated liposome formulation of 3M-052 was observed to increase survival and decrease lung virus titer when combined with a low dose (100 ng) of a recombinant HA based antigen. In addition, a formulation which incorporates 3M-052 and DMPC or egg PC into a squalene oil-in-water emulsion was tested, and has shown increased survival and reduced lung titer with this formulation in combination with rHA. Induction of Th1 CD4+ T cells in animals immunized with 3M-052 was observed. Consistent with a Th1 CD4+ T-cell induction, an increase of IgG2c antibodies in 3M-052 immunized animals was observed. The ability of 3M-052 containing adjuvant formulations to induce protection against both homologous and heterologous virus strains, as well as the extended stability of formulated 3M-052 adjuvants indicates that these formulations are suitable for stockpiling. Furthermore, the compatibility of these adjuvants with the pre-pandemic vaccine antigens currently included in the national stockpile is demonstrated, and show that a combination vaccine is capable of protecting ferrets against both strain-matched and drifted isolates.

Example 3: PEGylated Liposome Versatility

To test the versatility of the PEGylated liposome formulation, additional lipids were added to the base formulation of cholesterol, non-PEGylated neutral lipid, and PEGylated lipid. The addition of one or more additional neutral lipid and one or more additional cationic lipid did not negatively affect the stability or efficacy of the resultant liposomal formulation (Data not shown).

What is claimed:
1. A composition comprising:
 an antigen; and
 a liposome comprising:
  a cholesterol;
  a non-PEGylated neutral lipid;
  a PEGylated lipid, wherein an average molecular weight of the PEG in the PEGylated lipid is about 2000 Daltons, wherein a lipid molar ratio of the non-PEGylated neutral lipid:cholesterol:PEGylated lipid is about 9.8:5.7:0.8 or about 18:5.5:3; and agonists comprising GLA and 3M-052, wherein there is at least about twice as much GLA as 3M-052 by weight and wherein the GLA comprises a synthetic GLA of formula:

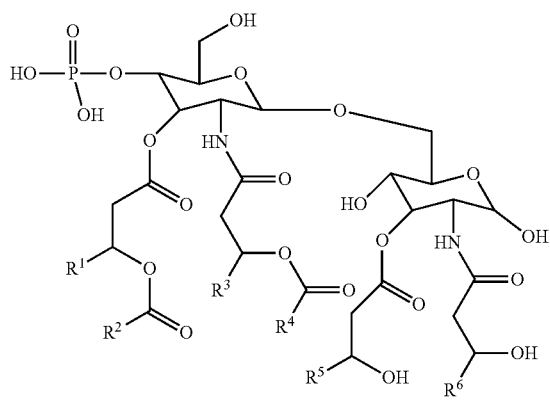

or a pharmaceutically acceptable salt thereof, wherein $R^1$, $R^3$, $R^5$, and $R^6$ are $C_{11}$-$C_{20}$ alkyl; and $R^2$ and $R^4$ are $C_{12}$-$C_{20}$ alkyl.

2. The composition of claim 1, wherein the lipid component of the PEGylated lipid is DSPE, DPPC, DOPC, DLPC, DMPC, DSPC, POPC, DPPE, or DMPE.

3. The composition of claim 1, wherein the lipid component of the PEGylated lipid comprises a $C_{14}$ alkyl chain, a $C_{16}$ alkyl chain, or a $C_{18}$ alkyl chain.

4. The composition of claim 1, wherein the non-PEGylated neutral lipid is DPPC, DOPC, DLPC, DMPC, DSPC, POPC, DPPE, or DMPE.

5. The composition of claim 1, wherein the non-PEGylated neutral lipid comprises a $C_{14}$ alkyl chain, a $C_{16}$ alkyl chain, or a $C_{18}$ alkyl chain.

6. The composition of claim 1, wherein $R^3$, $R^5$, and $R^6$ are $C_{11}$ alkyl; and $R^2$ and $R^4$ are $C_{13}$ alkyl.

7. The composition of claim 1, wherein the synthetic GLA has the formula:

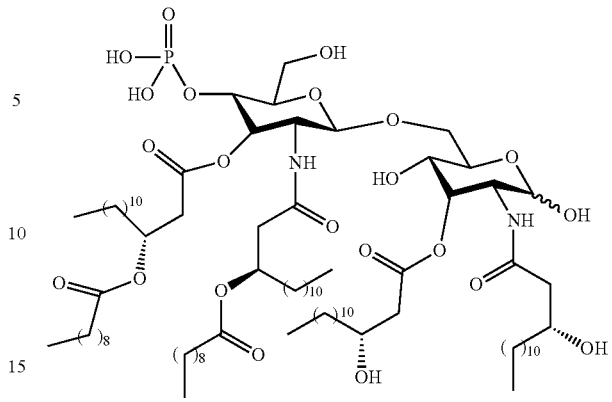

or a pharmaceutically acceptable salt thereof.

8. The composition of claim 1, wherein there is at about 2.5 times as much GLA as 3M-052 by weight.

9. The composition of claim 1, wherein the lipid molar ratio of the non-PEGylated neutral lipid:cholesterol:PEGylated lipid is about 9.8:5.7:0.8.

10. The composition of claim 1, wherein the lipid molar ratio of the non-PEGylated neutral lipid:cholesterol:PEGylated lipid is about 18:5.5:3.

11. The composition of claim 1, wherein the cholesterol is present at about 1-50 mol %, the non-PEGylated neutral lipid is present at about 45-98 mol %, and the PEGylated lipid is present at about 1-25 mol %.

12. The composition of claim 11, wherein the cholesterol is present at about 50 mol %, the non-PEGylated neutral lipid is present at about 45 mol %, and the PEGylated lipid is present at about 5 mol %.

13. The composition of claim 1, wherein a polydispersity index of the liposome is maintained at about 0.3 or less.

14. The composition of claim 1, wherein a size of the liposome is less than or about 450 nm.

15. The composition of claim 1, wherein the antigen comprises H5N1.

16. The composition of claim 1, wherein the antigen comprises LecA.

17. The composition of claim 1, further comprising an antioxidant.

18. The composition of claim 17, wherein the antioxidant comprises ascorbic acid, sodium bisulfite, or α-tocopherol.

* * * * *